(12) United States Patent
Elledge et al.

(10) Patent No.: US 11,821,110 B2
(45) Date of Patent: Nov. 21, 2023

(54) DETECTION OF AN ANTIBODY AGAINST A PATHOGEN

(71) Applicants: THE BRIGHAM AND WOMEN'S HOSPITAL, INC., Boston, MA (US); PRESIDENT AND FELLOWS OF HARVARD COLLEGE, Cambridge, MA (US)

(72) Inventors: Stephen J. Elledge, Brookline, MA (US); Harry B. Larman, San Diego, CA (US); Tomasz Kula, Brookline, MA (US); George Xu, Freemont, CA (US)

(73) Assignees: The Brigham and Women's Hospital, Inc., Boston, MA (US); President and Fellows of Harvard College, Cambridge, MA (US)

( * ) Notice: Subject to any disclaimer, the term of this patent is extended or adjusted under 35 U.S.C. 154(b) by 339 days.

(21) Appl. No.: 16/923,417

(22) Filed: Jul. 8, 2020

(65) Prior Publication Data
US 2020/0333356 A1 Oct. 22, 2020

Related U.S. Application Data

(62) Division of application No. 15/105,722, filed as application No. PCT/US2014/070902 on Dec. 17, 2014, now Pat. No. 10,768,181.

(60) Provisional application No. 61/917,104, filed on Dec. 17, 2013.

(51) Int. Cl.
| | |
|---|---|
| *C40B 40/02* | (2006.01) |
| *C40B 40/10* | (2006.01) |
| *G16B 25/00* | (2019.01) |
| *G01N 33/569* | (2006.01) |
| *G16B 25/20* | (2019.01) |

(Continued)

(52) U.S. Cl.
CPC .......... *C40B 40/10* (2013.01); *G01N 33/569* (2013.01); *G01N 33/56983* (2013.01); *G01N 33/56994* (2013.01); *G01N 33/6854* (2013.01); *G16B 25/00* (2019.02); *G16B 25/20* (2019.02); *C40B 30/04* (2013.01); *C40B 40/02* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 5,492,807 | A | 2/1996 | Santi |
| 2002/0197625 | A1 | 12/2002 | Hillman |
| 2003/0082524 | A1 | 5/2003 | Pincus |

(Continued)

FOREIGN PATENT DOCUMENTS

| | | |
|---|---|---|
| WO | 2011082381 A2 | 7/2011 |
| WO | 2013063366 A2 | 5/2013 |
| WO | 2015095355 A2 | 6/2015 |

OTHER PUBLICATIONS

Castel et al. "Phage display of combinatorial peptide libraries: application to antiviral research." Molecules 16(5):3499-3518 (2011).

(Continued)

*Primary Examiner* — Christian C Boesen
(74) *Attorney, Agent, or Firm* — Nixon Peabody LLP; David S. Resnick; Mark J. FitzGerald

(57) ABSTRACT

Provided herein are methods of detecting an antibody directed against a pathogen and uses thereof.

9 Claims, 39 Drawing Sheets

Specification includes a Sequence Listing.

(51) Int. Cl.
*G01N 33/68* (2006.01)
*C40B 30/04* (2006.01)

(56) References Cited

U.S. PATENT DOCUMENTS

2005/0123900 A1   6/2005   Dimitrov et al.
2013/0149336 A1   6/2013   Hjelle

OTHER PUBLICATIONS

Gnanasekar et al., "Novel phage display-based subtractive screening to identify vaccine candidates of Brugia malayi", Infect Immun 72(8) 4707-4715 (2004).

Larman et al., "Autoantigen discovery with a synthetic human peptidome", Nat Biotechnol 29(6) 535-541 (2011).

Larman et al., "Autoantigen discovery with a synthetic human peptidome", Nat Biotechnol 29(6) 535-541 and pp. 1-2 of online methods (2011).

Larman et al., "PhIP-Seq characterization of autoantibodies from patients with multiple sclerosis, type 1 diabetes and rheumatoid arthritis", J Autoimmun 43: 1-9 (2013).

Meyer et al., "Identification of immunogenic proteins and generation of antibodies against *Salmonella typhimurium* using phage display", BMC Biotechnol12: 29 (2012).

Meyer et al., "Illumina sequencing library preparation for highly multiplexed target capture and sequencing", Cold Spring Harb Procto 2010(6) (2010).

Vita et al., "The immune epitope database 2.0", Nucleic Acids Res 38(Database issue) D854-D862 (2010).

Xu et al. "Comprehensive serological profiling of human populations using a synthetic human virome" Science 348(6239): aaa0698 1-9 (2015).

Langmead et al. Ultrafast and memory-efficient alignment of short DNA sequences to the human genome Genome Biol, 1-10 (2009).

De Vlaminck et al., "Temporal response of the human virome to immunosuppression and antiviral therapy" Cell. 155 (2013), doi:10.1016/j.cell.2013.10.034.

EP 17744999.8 Search Report dated Jul. 12, 2019, 8 pgs.

| Virus | % |
|---|---|
| Epstein-Barr virus | 88.1 |
| Rhinovirus B | 75.2 |
| Human adenovirus C | 74.6 |
| Rhinovirus A | 73.9 |
| Respiratory syncytial virus | 68.0 |
| Influenza A virus | 58.4 |
| Human herpesvirus 6B | 57.1 |
| Herpes simplex virus 1 | 54.1 |
| Cytomegalovirus | 49.8 |
| Influenza B virus | 42.2 |
| Enterovirus C | 37.3 |
| Varicella zoster virus | 24.4 |
| Human adenovirus F | 22.1 |
| Human adenovirus B | 17.5 |
| Herpes simplex virus 2 | 16.5 |
| Human papillomaviruses | 9.9 |

SEQUENCE LISTING

```
<160> NUMBER OF SEQ ID NOS: 40

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Glu Ser Asp Ser Asp Ser Asp
1               5

<210> SEQ ID NO 2
<211> LENGTH: 56
<212> TYPE: PRT
```

<213> ORGANISM: Rhinovirus B

<400> SEQUENCE: 2

```
Gln Thr Asp Ala Leu Thr Glu Gly Leu Ser Asp Glu Leu Glu Glu Val
1               5                   10                  15

Ile Val Glu Lys Thr Lys Gln Thr Leu Ala Ser Val Ser Ser Gly Pro
            20                  25                  30

Lys His Thr Gln Ser Val Pro Ala Leu Thr Ala Asn Glu Thr Gly Ala
        35                  40                  45

Thr Leu Pro Thr Arg Pro Ser Asp
    50                  55
```

<210> SEQ ID NO 3
<211> LENGTH: 36
<212> TYPE: PRT
<213> ORGANISM: Human herpesvirus 5

<400> SEQUENCE: 3

```
Thr Ala Ser Gly Glu Glu Val Ala Val Leu Ser His His Asp Ser Leu
1               5                   10                  15

Glu Ser Arg Arg Leu Arg Glu Glu Glu Asp Asp Asp Asp Asp Glu Asp
            20                  25                  30

Phe Glu Asp Ala
        35
```

<210> SEQ ID NO 4
<211> LENGTH: 56
<212> TYPE: PRT
<213> ORGANISM: Enterovirus B

<400> SEQUENCE: 4

```
Ile Glu Gln Lys Gln Leu Leu Gln Gly Asp Val Glu Glu Ala Val Asn
1               5                   10                  15

Arg Ala Val Ala Arg Val Ala Asp Thr Leu Pro Thr Gly Pro Arg Asn
            20                  25                  30

Ser Glu Ser Ile Pro Ala Leu Thr Ala Ala Glu Thr Gly His Thr Ser
        35                  40                  45

Gln Val Val Pro Gly Asp Thr Met
    50                  55
```

<210> SEQ ID NO 5
<211> LENGTH: 30
<212> TYPE: PRT
<213> ORGANISM: Human herpesvirus 1

<400> SEQUENCE: 5

```
Arg Arg His Thr Gln Lys Ala Pro Lys Arg Ile Arg Leu Pro His Ile
1               5                   10                  15

Arg Glu Asp Asp Gln Pro Ser Ser His Gln Pro Leu Phe Tyr
            20                  25                  30
```

<210> SEQ ID NO 6
<211> LENGTH: 56
<212> TYPE: PRT
<213> ORGANISM: Human herpesvirus 4

<400> SEQUENCE: 6

```
Ser Pro Pro Arg Arg Pro Pro Pro Gly Arg Arg Pro Phe Phe His Pro
1               5                   10                  15

Val Ala Glu Ala Asp Tyr Phe Glu Tyr His Gln Glu Gly Gly Pro Asp
```

```
                    20                  25                  30

Gly Glu Pro Asp Met Pro Pro Gly Ala Ile Glu Gln Gly Pro Ala Asp
        35                  40                  45

Asp Pro Gly Glu Gly Pro Ser Thr
    50                  55

<210> SEQ ID NO 7
<211> LENGTH: 56
<212> TYPE: PRT
<213> ORGANISM: Human respiratory syncytial virus

<400> SEQUENCE: 7

Asn Lys Pro Ser Thr Lys Pro Arg Pro Lys Asn Pro Pro Lys Lys Pro
1               5                   10                  15

Lys Asp Asp Tyr His Phe Glu Val Phe Asn Phe Val Pro Cys Ser Ile
                20                  25                  30

Cys Gly Asn Asn Gln Leu Cys Lys Ser Ile Cys Lys Thr Ile Pro Ser
            35                  40                  45

Asn Lys Pro Lys Lys Lys Pro Thr
    50                  55

<210> SEQ ID NO 8
<211> LENGTH: 30
<212> TYPE: PRT
<213> ORGANISM: Human adenovirus C

<400> SEQUENCE: 8

Met Thr Gln Gly Arg Arg Gly Asn Val Tyr Trp Val Arg Asp Ser Val
1               5                   10                  15

Ser Gly Leu Arg Val Pro Val Arg Thr Arg Pro Pro Arg Asn
                20                  25                  30

<210> SEQ ID NO 9
<211> LENGTH: 56
<212> TYPE: PRT
<213> ORGANISM: Enterovirus C

<400> SEQUENCE: 9

Gln Gly Ala Leu Thr Leu Ser Leu Pro Lys Gln Gln Asp Ser Leu Pro
1               5                   10                  15

Asp Thr Lys Ala Ser Gly Pro Ala His Ser Lys Glu Val Pro Ala Leu
                20                  25                  30

Thr Ala Val Glu Thr Gly Ala Thr Asn Pro Leu Ala Pro Ser Asp Thr
            35                  40                  45

Val Gln Thr Arg His Val Val Gln
    50                  55

<210> SEQ ID NO 10
<211> LENGTH: 56
<212> TYPE: PRT
<213> ORGANISM: Human herpesvirus 3

<400> SEQUENCE: 10

Pro Asp Pro Ala Val Ala Pro Thr Ser Ala Ala Ser Arg Lys Pro Asp
1               5                   10                  15

Pro Ala Val Ala Pro Thr Ser Ala Ala Ser Arg Lys Pro Asp Pro Ala
                20                  25                  30

Val Ala Pro Thr Ser Ala Ala Thr Arg Lys Pro Asp Pro Ala Val Ala
            35                  40                  45
```

```
Pro Thr Ser Ala Ala Ser Arg Lys
    50                  55
```

<210> SEQ ID NO 11
<211> LENGTH: 56
<212> TYPE: PRT
<213> ORGANISM: Norwalk virus

<400> SEQUENCE: 11

```
Leu Ser Ser Met Ala Ile Thr Phe Lys Arg Ala Leu Gly Ala Arg Pro
1               5                   10                  15

Lys Gln Pro Pro Pro Arg Glu Ile Leu Gln Arg Pro Pro Arg Pro Pro
            20                  25                  30

Thr Pro Glu Leu Val Lys Lys Ile Pro Pro Pro Pro Asn Gly Glu
        35                  40                  45

Asp Glu Leu Val Val Ser Tyr Ser
    50                  55
```

<210> SEQ ID NO 12
<211> LENGTH: 56
<212> TYPE: PRT
<213> ORGANISM: Human immunodeficiency virus 1

<400> SEQUENCE: 12

```
Glu Arg Tyr Leu Lys Asp Gln Gln Leu Leu Gly Ile Trp Gly Cys Ser
1               5                   10                  15

Gly Lys Leu Ile Cys Thr Thr Ala Val Pro Trp Asn Ala Ser Trp Ser
            20                  25                  30

Asn Lys Ser Leu Glu Gln Ile Trp Asn Asn Met Thr Trp Met Glu Trp
        35                  40                  45

Asp Arg Glu Ile Asn Asn Tyr Thr
    50                  55
```

<210> SEQ ID NO 13
<211> LENGTH: 56
<212> TYPE: PRT
<213> ORGANISM: Influenza A virus

<400> SEQUENCE: 13

```
Leu Gly His His Ala Val Pro Asn Gly Thr Leu Val Lys Thr Ile Thr
1               5                   10                  15

Asn Asp Gln Ile Glu Val Thr Asn Ala Thr Glu Leu Val Gln Ser Ser
            20                  25                  30

Ser Thr Gly Arg Ile Cys Asp Ser Pro His Arg Ile Leu Asp Gly Lys
        35                  40                  45

Asn Cys Thr Leu Ile Asp Ala Leu
    50                  55
```

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aggaattccg ctgcgt                                                  16

<210> SEQ ID NO 15
<211> LENGTH: 16

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cagggaagag ctcgaa                                                    16

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aatgatacgg cgggaattcc gctgcgt                                        27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caagcagaag actcgagctc ttccctg                                        27

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acactctttc cctacacgac tccagtcagg tgtgatgctc                          40

<210> SEQ ID NO 19
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtgactggag ttcagacgtg tgctcttccg atccgagctt atcgtcgtca tcc           53

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aatgatacgg cgaccaccga gatctacact ctttccctac acgactccag t             51

<210> SEQ ID NO 21
<211> LENGTH: 52
<212> TYPE: DNA

```
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(31)
<223> OTHER INFORMATION: a, c, t, g, unknown or other

<400> SEQUENCE: 21
caagcagaag acggcatacg agatnnnnnn ngtgactgga gttcagacgt gt              52

<210> SEQ ID NO 22
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Lys Arg Thr Pro Pro Ala Pro Gln Asn Pro Gly Gly Ser Thr Gln Ala
1               5                   10                  15

Pro Gln Arg Val Val Gly Lys Ser His Ser Gly Ile Arg Met Pro Ala
            20                  25                  30

Lys Ser Arg Asn Arg
        35

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Trp Pro Gly Arg Thr Val Lys Asp Glu Phe Gly Gly Arg Leu Asp Pro
1               5                   10                  15

Pro Ala Ala Ser Arg Ser Arg Arg Glu Pro Arg Arg Ala Gly Arg
            20                  25                  30

Trp Gly Arg Gly
        35

<210> SEQ ID NO 24
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Leu Gly Arg Ser Arg Ala Thr Ala Thr Trp Pro Ala Ala Ser Arg
1               5                   10                  15

Ser Arg Ser Leu Ala Ala Arg Ser Leu Pro Arg Ser Pro Ala Arg Pro
            20                  25                  30

Gly Pro Asn Asp
        35

<210> SEQ ID NO 25
<211> LENGTH: 36
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 25

Ser Met Pro Ser Leu Met Thr Gly Arg Ser Ala Pro Pro Ser Pro Ala
1               5                   10                  15

Leu Ser Arg Ser His Pro Arg Thr Gly Ser Val Gln Thr Ser Pro Ser
            20                  25                  30

Ser Thr Pro Val
        35

<210> SEQ ID NO 26
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Leu Asp His Gly Ser Pro Ala Gln Glu Asn Pro Glu Ser Glu Lys Ser
1               5                   10                  15

Ser Pro Ala Val Ser Arg Ser Lys Thr Phe Thr Gly Arg Phe Lys Gln
            20                  25                  30

Gln Thr Pro Ser
        35

<210> SEQ ID NO 27
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Ser Arg Gln Ser Ser Ile Thr Phe Gln Gly Ser Arg Arg Gly
1               5                   10                  15

Phe Ser Thr Thr Ser Ala Ile Thr Pro Ala Ala Gly Arg Ser Arg Phe
            20                  25                  30

Ser Ser Val Ser
        35

<210> SEQ ID NO 28
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser Ala Ala Pro Glu Pro Arg Pro Ala Pro Gly Arg Ser Arg Ala Met
1               5                   10                  15

Gly Val Leu Met Ser Lys Arg Gln Thr Val Glu Gln Val Gln Lys Val
            20                  25                  30

Ser Leu Ala Val
        35

<210> SEQ ID NO 29
<211> LENGTH: 36
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 29

Thr Arg Ser Arg Ser His Ser Pro Ser Pro Ser Gln Ser Arg Ser Arg
1               5                   10                  15

Ser Arg Ser Arg Ser Gln Ser Pro Ser Pro Ala Arg Glu Lys
            20                  25                  30

Leu Thr Arg Pro
            35

<210> SEQ ID NO 30
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Ala His Ala Ser Leu Asn Pro Ala Leu Phe Ser Met Lys Met Glu
1               5                   10                  15

Leu Ala Gly Ser Asn Thr Thr Ala Ser Ser Pro Ala Arg Ala Arg Ser
            20                  25                  30

Arg Pro Leu Lys
            35

<210> SEQ ID NO 31
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser Gly Gly Pro Ser Ser Cys Gly Gly Ala Pro Ser Thr Ser Arg Ser
1               5                   10                  15

Arg Pro Ser Arg Ile Pro Gln Pro Val Arg His His Pro Pro Val Leu
            20                  25                  30

Val Ser Ser Ala
            35

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asn Pro Gly Cys His Pro Ser Pro Thr Pro Met Leu Ala Ser Gln Arg
1               5                   10                  15

His Cys Arg Asp Ser Ala Ala Val Cys Val His Val Thr Pro Ser Pro
            20                  25                  30

Ser Arg Ser Leu
            35

<210> SEQ ID NO 33
<211> LENGTH: 56
<212> TYPE: PRT
```

<213> ORGANISM: Human adenovirus C

<400> SEQUENCE: 33

His Ala Ile Arg Gly Asp Thr Phe Ala Thr Arg Ala Glu Glu Lys Arg
1               5                   10                  15

Ala Glu Ala Glu Ala Ala Glu Ala Ala Pro Ala Ala Gln Pro
            20                  25                  30

Glu Val Glu Lys Pro Gln Lys Lys Pro Val Ile Lys Pro Leu Thr Glu
        35                  40                  45

Asp Ser Lys Lys Arg Ser Tyr Asn
    50                  55

<210> SEQ ID NO 34
<211> LENGTH: 56
<212> TYPE: PRT
<213> ORGANISM: Influenza A virus

<400> SEQUENCE: 34

Leu Gly His His Ala Val Pro Asn Gly Thr Leu Val Lys Thr Ile Thr
1               5                   10                  15

Asn Asp Gln Ile Glu Val Thr Asn Ala Thr Glu Leu Val Gln Ser Ser
            20                  25                  30

Ser Thr Gly Arg Ile Cys Asp Ser Pro His Arg Ile Leu Asp Gly Lys
        35                  40                  45

Asn Cys Thr Leu Ile Asp Ala Leu
    50                  55

<210> SEQ ID NO 35
<211> LENGTH: 56
<212> TYPE: PRT
<213> ORGANISM: Respiratory syncytial virus

<400> SEQUENCE: 35

Ser Thr Thr Lys Gln Arg Gln Asn Lys Pro Gln Asn Lys Pro Asn Asn
1               5                   10                  15

Asp Phe His Phe Glu Val Phe Asn Phe Val Pro Cys Ser Ile Cys Ser
            20                  25                  30

Asn Asn Pro Thr Cys Trp Ala Ile Cys Lys Arg Ile Pro Asn Lys Lys
        35                  40                  45

Pro Gly Lys Lys Thr Thr Thr Lys
    50                  55

<210> SEQ ID NO 36
<211> LENGTH: 56
<212> TYPE: PRT
<213> ORGANISM: Enterovirus B

<400> SEQUENCE: 36

Gly Pro Ser Asn Ser Glu Ser Ile Pro Ala Leu Thr Ala Ala Glu Thr
1               5                   10                  15

Gly His Thr Ser Gln Val Val Pro Ser Asp Thr Ile Gln Thr Arg His
            20                  25                  30

Val Arg Asn Phe His Val Arg Ser Glu Ser Ser Val Glu Asn Phe Leu
        35                  40                  45

Ser Arg Ser Ala Cys Val Tyr Ile
    50                  55

<210> SEQ ID NO 37
<211> LENGTH: 56

```
<212> TYPE: PRT
<213> ORGANISM: Enterovirus B

<400> SEQUENCE: 37

Arg His Ser Val Gly Thr Thr Leu Glu Ala Leu Phe Gln Gly Pro Pro
1               5                   10                  15

Val Tyr Arg Glu Ile Lys Ile Ser Val Ala Pro Glu Thr Pro Pro Pro
                20                  25                  30

Pro Ala Ile Ala Asp Leu Leu Lys Ser Val Asp Ser Glu Ala Val Arg
            35                  40                  45

Glu Tyr Cys Lys Glu Lys Gly Trp
    50                  55

<210> SEQ ID NO 38
<211> LENGTH: 56
<212> TYPE: PRT
<213> ORGANISM: Rhinovirus A

<400> SEQUENCE: 38

Lys Gln Thr Gly Pro Ile Thr Gln Asn Pro Val Glu Arg Tyr Val Asp
1               5                   10                  15

Glu Val Leu Asn Glu Val Leu Val Pro Asn Ile Asn Gln Ser His
                20                  25                  30

Pro Thr Thr Ser Asn Ala Ala Pro Val Leu Asp Ala Ala Glu Thr Gly
            35                  40                  45

His Thr Asn Lys Ile Gln Pro Glu
    50                  55

<210> SEQ ID NO 39
<211> LENGTH: 56
<212> TYPE: PRT
<213> ORGANISM: Epstein-Barr virus

<400> SEQUENCE: 39

Ser Pro Pro Arg Arg Pro Pro Gly Arg Arg Pro Phe Phe His Pro
1               5                   10                  15

Val Ala Glu Ala Asp Tyr Phe Glu Tyr His Gln Glu Gly Gly Pro Asp
                20                  25                  30

Gly Glu Pro Asp Met Pro Pro Gly Ala Ile Glu Gln Gly Pro Ala Asp
            35                  40                  45

Asp Pro Gly Glu Gly Pro Ser Thr
    50                  55

<210> SEQ ID NO 40
<211> LENGTH: 53
<212> TYPE: PRT
<213> ORGANISM: Human adenovirus C

<400> SEQUENCE: 40

Val Pro Gly Pro Arg Pro Pro Thr Arg Arg Gln Arg His Asp Arg Gln
1               5                   10                  15

Arg Gly Leu Val Trp Glu Asp Asp Ser Ala Asp Asp Ser Ser Val
                20                  25                  30

Leu Asp Leu Gly Gly Ser Gly Asn Pro Phe Ala His Leu Arg Pro Arg
            35                  40                  45

Leu Gly Arg Met Phe
    50
```

DETECTION OF AN ANTIBODY AGAINST A PATHOGEN

CROSS-REFERENCE TO RELATED APPLICATIONS

This application is a Divisional of U.S. patent application Ser. No. 15/105,722, filed Jun. 17, 2016, which is a 35 U.S.C. § 371 National Phase Entry Application of International Patent Application No. PCT/US2014/070902 filed Dec. 17, 2014, which designates the U.S. and which claims benefit under 35 U.S.C. § 119(e) of U.S. Provisional Application No. 61/917,104 filed Dec. 17, 2013, the contents of each of which are incorporated herein by reference in their entirety.

SEQUENCE LISTING

The instant application contains a Sequence Listing, which has been submitted electronically in ASCII format and is hereby incorporated by reference in its entirety. Said ASCII copy, created on Jul. 7, 2020, is named 20150220_Sequence_Listing_TXT_043214-079311-PCT.txt and is 17,862 bytes in size.

BACKGROUND

Vertebrate immune systems have evolved sophisticated genetic mechanisms to generate T-cell receptor and antibody repertoires, which are combinatorial libraries of affinity molecules capable of distinguishing between self and non-self. In higher mammals, a delicate balance is struck between metabolism, immune defense against pathogens and autoimmunity, wherein disturbances can result in disease and dysfunction. Amongst such pathogens are viruses. A host's antibody response is crucial for preventing viral infection, or resolution of infection, as antibodies are produced against many epitopes on multiple virus proteins upon viral contact. However, these processes can go awry when, for example, antibodies recognizing viral peptides cross-react with human antigens and contribute to autoimmune disease.

Antibodies bind protein antigens by a variety of mechanisms and knowledge of the processes governing these interactions is improving. For instance, it is now understood that antibody binding surfaces on natively folded proteins tend to be dominated by 'discontinuous' epitopes, which are patches of ~4 to 14 amino acid side chains formed by two or more noncontiguous peptides brought into proximity during protein folding. If a protein is divided into its constituent peptides, antibody affinity can decrease due to the loss of contacts contributed by noncontiguous residues, and the increased entropic costs of binding a free peptide as opposed to the natively constrained peptide. On the other hand, antibodies targeting normally inaccessible epitopes can be generated, such as those that recognize proteolytic cleavage products, misfolded proteins or protein aggregates. In circumstances such as these, full-length, folded proteins may be less sensitive using antigen detection techniques than with shorter peptides. Thus, the degree to which individual peptides interact with a given antibody is difficult to predict, and is expected to vary widely not only amongst different peptides, but also within same or similar peptides introduced into different individuals. In the specific instance of viral antigens, wide-scale, parallel detection is particularly challenging, given highly adaptive evolutionary nature of viruses and comparatively small antigenic signature.

Unfortunately, traditional phage display systems, lack sufficient sensitivity and accuracy to account for such potential antigenic variations. For example, existing techniques for identifying autoantibody targets have relied largely on the expression of fragmented cDNA libraries, such as polypeptides fused to the capsid proteins of bacteriophage. Notable technical limitations of this method include the small fraction of clones expressing coding sequences in the correct reading frame (with a lower bound of 6%), and system bias due to the highly skewed representation of differentially expressed cDNAs.

SUMMARY

Described herein is a proteomic technology applying a phage library that can uniformly express peptide libraries, such as the substantially complete human peptidome, or synthetic representations of a substantially complete set of viral peptides known to infect humans. By combining T7-Pep phage library with high-throughput DNA sequencing, the described systems and methods allow for a wide variety of high-throughput proteomic investigations, with unprecedented speed, precision, and accuracy. For example, the inventors successfully established a complete set of viral peptides containing 79,407 peptide sequences derived from 788 unique viruses, encompassing over 201 species, 67 genera, and 29 families of viruses. This comprehensive library allows simultaneous detection of antiviral antibody response in a subject for both prior and ongoing exposure against virtually all of known viruses capable of infecting humans. Such systems and methods allow a systematic approach for detection of virus infection, mapping of antiviral antibody epitopes, identification of cross-reactive autoimmune epitopes, among a variety of other diagnostic, clinical and technical uses. Thus, provided herein are phage libraries and methods for use including, but not limited to, methods for detecting an antibody against a virus, methods for identifying a viral cause of disease, and methods for improving vaccine design.

One aspect provided herein relates to a method for detecting an antibody against a pathogen in a subject, the method comprising: (a) contacting a reaction sample comprising a display library with a biological sample comprising antibodies, wherein the display library comprises a plurality of peptides derived from a plurality of pathogens, and (b) detecting a peptide bound to at least one antibody, thereby detecting an antibody capable of binding the peptide.

In one embodiment of this aspect and all other aspects described herein, the plurality of pathogens is a plurality of viruses, bacteria or fungi.

In another embodiment of this aspect and all other aspects described herein, the display library is a phage display library.

In another embodiment of this aspect and all other aspects described herein, the antibodies in the reaction sample are immobilized.

In another embodiment of this aspect and all other aspects described herein, the antibodies are immobilized to a solid support adapted for binding IgM, IgA, or IgG subclasses.

In another embodiment of this aspect and all other aspects described herein, the antibodies are immobilized by contacting the display library and antibodies from the biological sample with Protein A and/or Protein G.

In another embodiment of this aspect and all other aspects described herein, the Protein A and/or Protein G are immobilized to a solid support.

In another embodiment of this aspect and all other aspects described herein, the method further comprises removing unbound antibody and peptides of the display library.

In another embodiment of this aspect and all other aspects described herein, the plurality of peptides are each less than 100, 200, 300, 500, 500, 600, 700, 800, or 900 amino acids long.

In another embodiment of this aspect and all other aspects described herein, the plurality of peptides are each less than 75 amino acids long.

In another embodiment of this aspect and all other aspects described herein, each peptide of the plurality of peptides comprises a common adapter region appended to the end of the nucleic acid sequence encoding the peptide.

In another embodiment of this aspect and all other aspects described herein, the detection of the at least one peptide comprises a step of lysing the phage and amplifying the DNA.

In another embodiment of this aspect and all other aspects described herein, at least two antibodies are detected. In another embodiment of this aspect and all other aspects described herein, at least two peptides are detected.

In another embodiment of this aspect and all other aspects described herein, the at least two antibodies are detected simultaneously. In another embodiment of this aspect and all other aspects described herein, the at least two peptides are detected simultaneously.

In another embodiment of this aspect and all other aspects described herein, antibodies from the biological samples are immobilized.

Another aspect provided herein relates to a method for identifying a pathogenic component in a disease, the method comprising: (a) obtaining a biological sample from a plurality of subjects having a common disease, wherein the common disease is suspected of having a pathogenic component, (b) separately contacting each sample of a plurality of reaction samples with each biological sample under conditions that allow formation of at least one antibody-peptide complex, wherein the reaction samples each comprise a display library comprising a plurality of peptides derived from a plurality of pathogens, (c) isolating the at least one antibody-peptide complex formed in each reaction sample from unbound phage, (d) correlating at least one peptide in the at least one antibody-peptide complex in each reaction sample to the pathogen from which it is derived, and (e) identifying a pathogen that is significantly enriched in the plurality of subjects with disease compared to subjects without the disease.

In one embodiment of this aspect and all other aspects described herein, the plurality of pathogens is a plurality of viruses, bacteria or fungi.

In another embodiment of this aspect and all other aspects described herein, the display library is a phage display library.

In another embodiment of this aspect and all other aspects described herein, the antibodies in the reaction sample are immobilized.

In another embodiment of this aspect and all other aspects described herein, the antibodies are immobilized to a solid support adapted for binding IgM, IgA, or IgG subclasses.

In another embodiment of this aspect and all other aspects described herein, the antibodies are immobilized by contacting the display library and antibodies from the biological sample with Protein A and/or Protein G.

In another embodiment of this aspect and all other aspects described herein, the Protein A and/or Protein G are immobilized to a solid support.

In another embodiment of this aspect and all other aspects described herein, the plurality of peptides are each less than 100, 200, 300, 400, 500, 600, 700, 800 or 900 amino acids long.

In another embodiment of this aspect and all other aspects described herein, the plurality of peptides are each less than 75 amino acids long.

In another embodiment of this aspect and all other aspects described herein, each peptide of the plurality of peptides comprises a common adapter region appended to the end of the nucleic acid sequence encoding the peptide.

In another embodiment of this aspect and all other aspects described herein, correlating the at least one peptide comprises a step of lysing the phage and amplifying the DNA.

In another embodiment of this aspect and all other aspects described herein, at least two peptides are detected.

In another embodiment of this aspect and all other aspects described herein, the at least two peptides are detected simultaneously.

In another embodiment of this aspect and all other aspects described herein, the common disease comprises disease selected from the group consisting of: Kawasaki Disease, Bell's Palsy, Meniere's Disease, Type I diabetes, juvenile idiopathic arthritis, Chronic Fatigue Syndrome, Gulf War Illness, Myasthenia Gravis, and IgG4 disease.

In another embodiment of this aspect and all other aspects described herein, the method further comprises identifying the epitope to which the antibody binds.

In another embodiment of this aspect and all other aspects described herein, the method further comprises determining whether the antibody cross-reacts with an autoimmune antigen in the subject.

Another aspect provided herein relates to a method for improving vaccine design, the method comprising: (a) obtaining a biological sample from a plurality of subjects exposed to a pathogen, (b) separately contacting each sample of a plurality of reaction samples with each biological sample under conditions that allow formation of at least one antibody-peptide complex, wherein the reaction samples each comprise a display library comprising a plurality of peptides derived from a plurality of pathogens, (c) isolating the at least one antibody-peptide complex formed in each reaction sample from unbound phage, (d) correlating at least one peptide in the at least one antibody-peptide complex in each reaction sample to the pathogen from which it is derived, and (e) identifying an antigenic peptide that is significantly enriched in the plurality of subjects exposed to the pathogen as compared to subjects that have not been exposed to the pathogen for use in designing an improved vaccine.

In one embodiment of this aspect and all other aspects described herein, the plurality of pathogens is a plurality of viruses, bacteria or fungi.

In another embodiment of this aspect and all other aspects described herein, the display library is a phage display library.

In another embodiment of this aspect and all other aspects described herein, the antibodies in the reaction sample are immobilized.

In another embodiment of this aspect and all other aspects described herein, the antibodies are immobilized to a solid support adapted for binding IgM, IgA, or IgG subclasses.

In another embodiment of this aspect and all other aspects described herein, the antibodies are immobilized by contacting the display library and antibodies from the biological sample with Protein A and/or Protein G.

In another embodiment of this aspect and all other aspects described herein, the Protein A and/or Protein G are immobilized to a solid support.

In another embodiment of this aspect and all other aspects described herein, the plurality of peptides are each less than 100 amino acids long.

In another embodiment of this aspect and all other aspects described herein, the plurality of peptides are each less than 75 amino acids long.

In another embodiment of this aspect and all other aspects described herein, each peptide of the plurality of peptides comprises a common adapter region appended to the end of the nucleic acid sequence encoding the peptide.

In another embodiment of this aspect and all other aspects described herein, the detection of the antigenic peptide comprises a step of lysing the phage and amplifying the DNA.

In another embodiment of this aspect and all other aspects described herein, at least two antibodies are detected.

In another embodiment of this aspect and all other aspects described herein, the at least two antibodies are detected simultaneously.

Also provided herein, in another aspect, is a phage library displaying a plurality of viral peptides, wherein the plurality of viral peptides represent a set of peptides from viruses known to infect humans.

In one embodiment of this aspect and all other aspects described herein, the phage library comprises a plurality of viral peptides from at least 3 viruses known to infect humans.

In another embodiment of this aspect and all other aspects described herein, the phage library comprises a plurality of viral peptides from at least 10 viruses known to infect humans.

In another embodiment of this aspect and all other aspects described herein, the phage library comprises a plurality of viral peptides from at least 20 viruses known to infect humans.

In another embodiment of this aspect and all other aspects described herein, the phage library comprises at least 10 peptide sequences.

In another embodiment of this aspect and all other aspects described herein, the phage library comprises at least 20 peptide sequences.

In another embodiment of this aspect and all other aspects described herein, the plurality of peptides are each less than 100 amino acids long.

In another embodiment of this aspect and all other aspects described herein, the plurality of peptides are each less than 75 amino acids long.

In another embodiment of this aspect and all other aspects described herein, each peptide of the plurality of peptides comprises a common adapter region appended to the end of the nucleic acid sequence encoding the peptide.

In another embodiment of this aspect and all other aspects described herein, the plurality of peptides are immunodominant epitopes.

BRIEF DESCRIPTION OF FIGURES

(FIG. 4A) Antibody profile of randomly chosen group of donors to show typical assay results. Each row is a virus, each column is a sample. The label above each chart indicates whether the donors are over 10 years of age or at most 10 years of age. The intensity of each cell indicates the number of peptides from the virus that were significantly enriched by antibodies in the sample. (FIG. 4B) Overlap between enriched peptides detected by VirScan and human B cell epitopes from viruses in IEDB. The entire pink circle represents the 1,715 groups of non-redundant IEDB epitopes that are also present in the VirScan library (out of 1,877 clusters total). The overlap region represents the number of groups with an epitope that is also contained in an enriched peptide detected by VirScan. The purple only region represents the number of non-redundant enriched peptides detected by VirScan that do not contain an IEDB epitope. Data are shown for peptides enriched in at least one and at least two samples. (FIG. 4C) Overlap between enriched peptides detected by VirScan and human B cell epitopes in IEDB from common human viruses. The regions represent the same values as in (FIG. 4B) except only epitopes corresponding to the indicated virus are considered, and only peptides from that virus that were enriched in at least two samples were considered. (FIG. 4D) Distribution of number of viruses detected in each sample. The histogram depicts the frequency of samples binned by the number of virus species detected by VirScan. The mean and median of the distribution are both approximately 11 virus species. (FIG. 4E) Frequently observed virus exposures. The "%" column indicates the percentage of samples that were positive for the virus by VirScan. Known HIV and HCV positive samples were excluded when performing this analysis.

(FIG. 11A) Bar graph of the fractional abundance of each amino acid in the entire virome peptide library or peptides enriched in at least 2 samples. (FIG. 11B) Bar graph of the fractional abundance of each amino acid in peptides enriched in at least 2 samples subtracted by the abundance in the entire library.

Figure 18A:
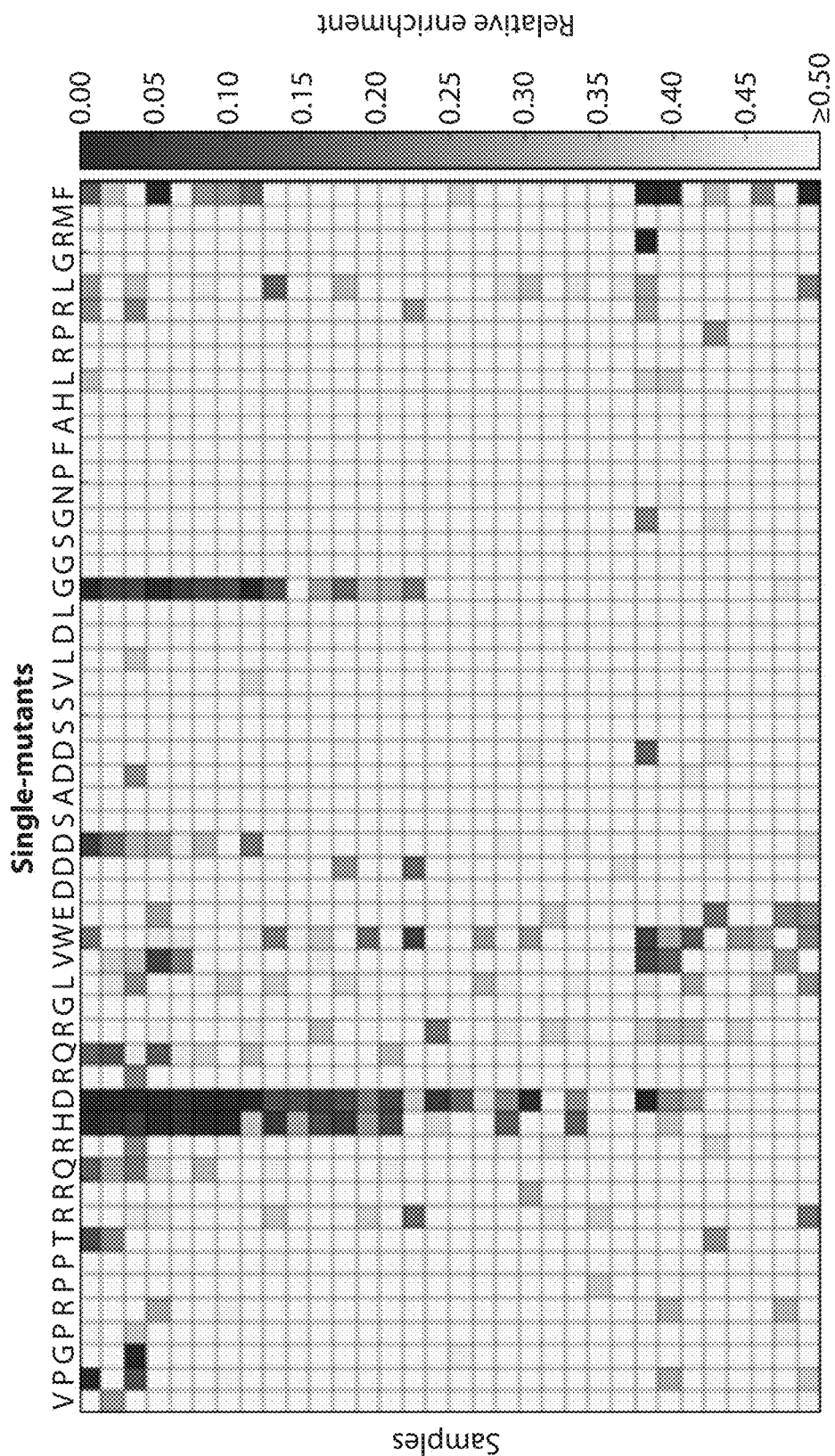
Figure 18B:
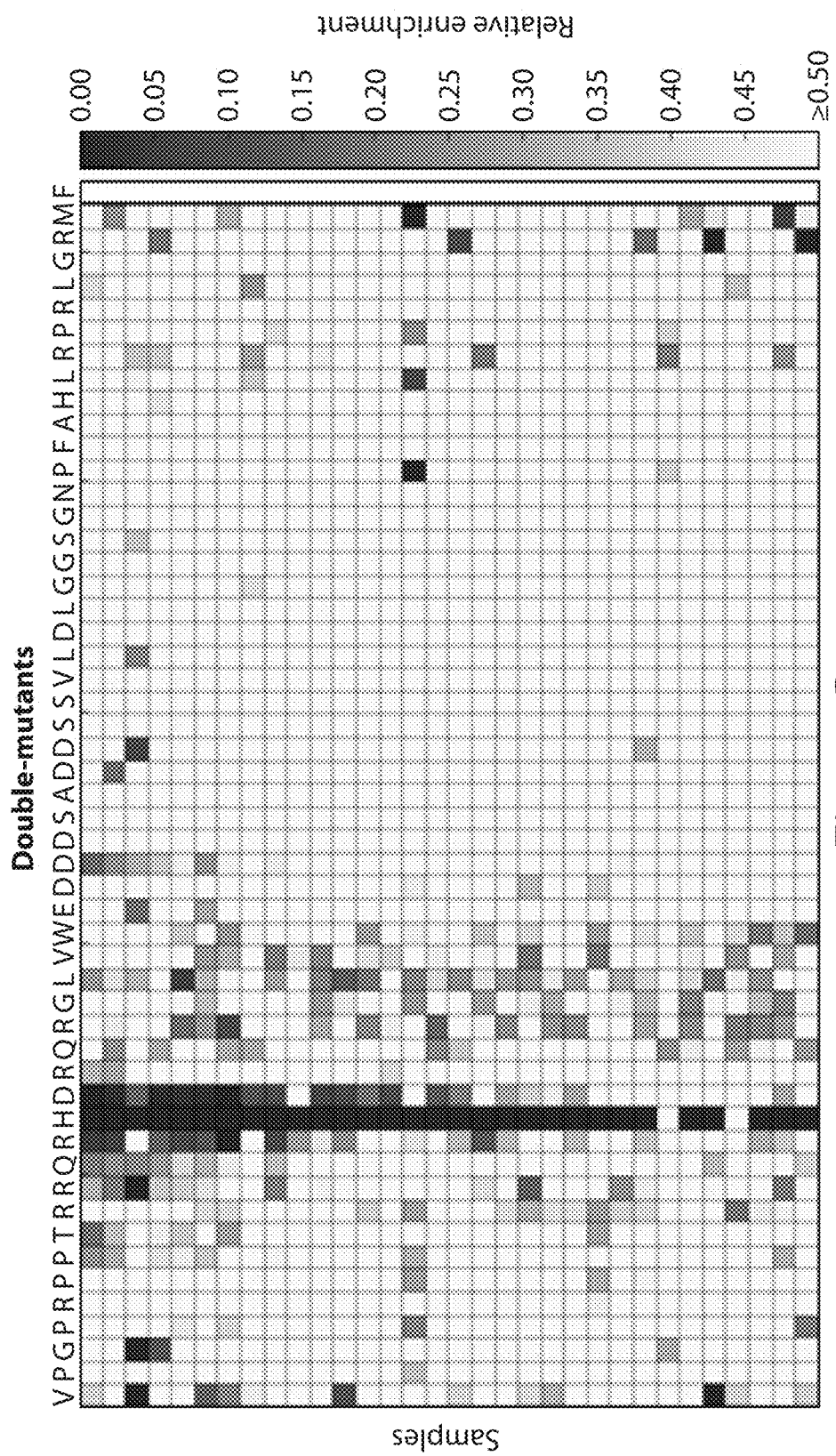
Figure 18C:
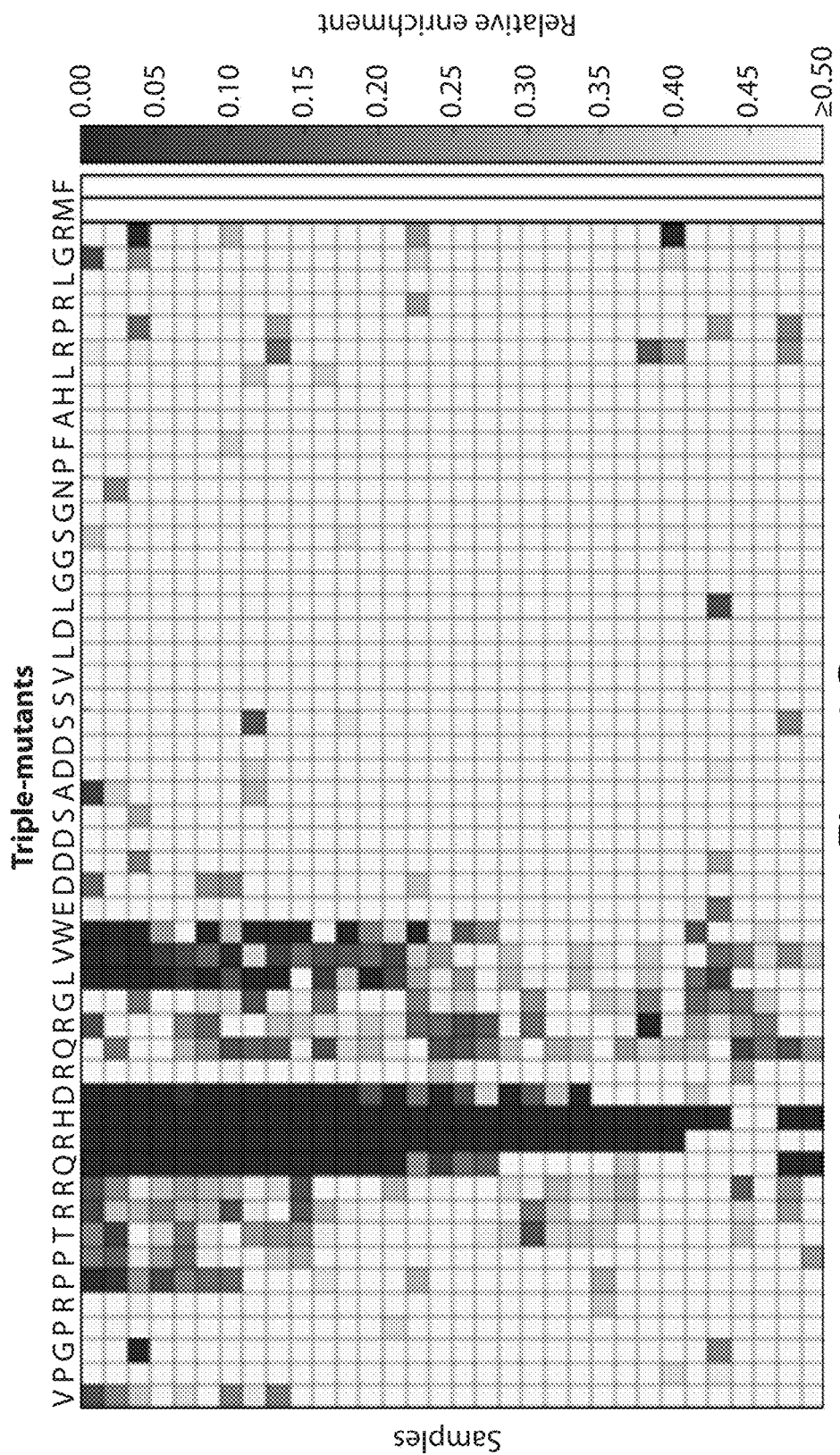

sample. Each column denotes the first mutated position for (FIG. 18A) single- (SEQ ID NO: 40), (FIG. 18B) double- (SEQ ID NO: 40), and (FIG. 18C) triple-alanine (SEQ ID NO: 40) mutant peptides. The intensity of each cell indicates the enrichment of the mutant peptide relative to the wild-type. For double-mutants, the last position is blank. The same is true for the last two positions for triple-mutants. Data shown are the mean of two replicates.

Figure 19A:
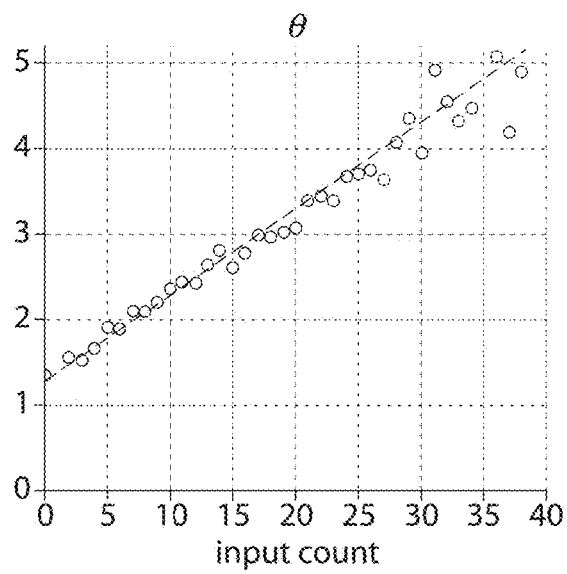
Figure 19B:
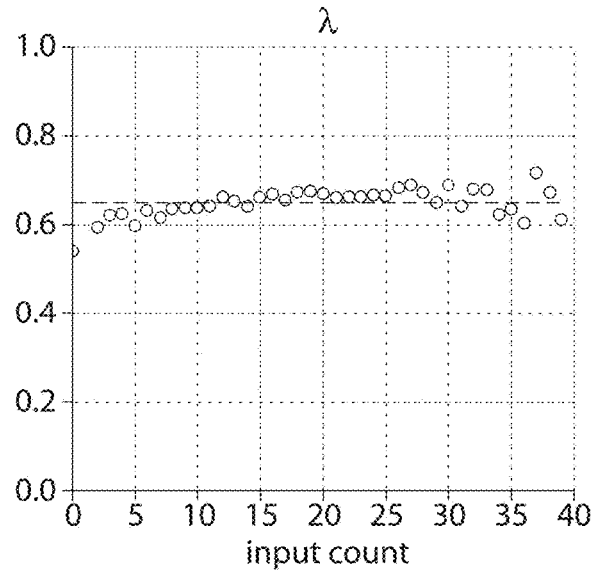
Figure 19C:
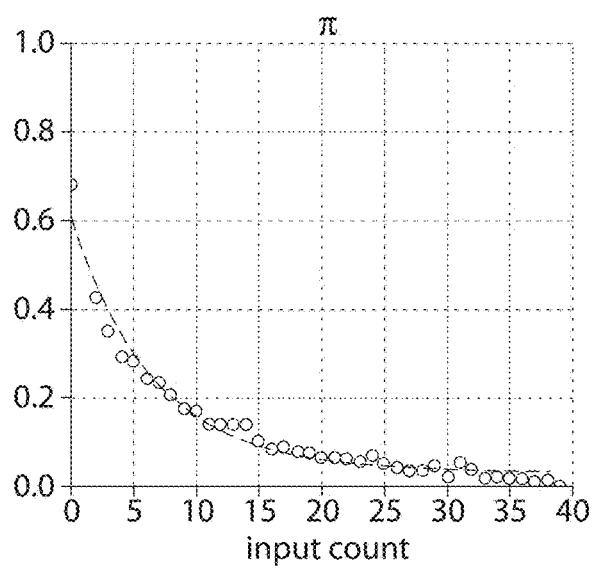

FIGS. 19A-19C Zero inflated generalized poisson (ZIGP) parameters regressed on input count. Each scatter plot depicts the maximum likelihood estimates for the ZIGP parameters as a function of the input count (horizontal axis). Dashed lines are least-squares linear regressions for $\theta$ and $\lambda$, and least-squares exponential regression for $\pi$.

DETAILED DESCRIPTION

The inventors have previously deployed programmable microarrays to synthesize oligonucleotides encoding wide sets of peptides, such as the complete human peptidome, coupled with high throughput sequencing to analyze the results after selection. Larman, H. Benjamin, et al. "Autoantigen discovery with a synthetic human peptidome." *Nature Biotechnology* 29: 535-541 (2011). Described herein is a specific implementation of that approach wherein synthetic representations of a complete set of viral peptides can be generated, such as a set of viral peptides derived from viruses known to infect humans.

One aspect of the present technology is that unlike existing phage display techniques which rely on cDNA, programmable microarrays enable construction of a starting library that is uniformly distributed. The synthetic programmable microarray approach eliminates skewed initial distributions in cDNA libraries resulting from incorrect reading frame or differential gene expression obstacles, which ultimately hamper accurate detection of peptide enrichment. Further, when coupled with high throughput sequencing for selection, the programmable microarray approach compares favorably to traditional Sanger sequencing or microarray hybridization techniques, as high throughput phage immunoprecipitation sequencing (PhIP-Seq) allows sensitive detection for a larger number of library members and with a wider dynamic range.

A key aspect of the present invention is extending the programmable microarray technique to include peptides from the protein sequences of viruses, including those that infect humans. Viruses play an important role in the pathogenesis of various human diseases and antiviral antibody responses can be very strong, essentially providing a persistent, but subtle antibody host signature for detection. Upon viral or other pathogenic exposure, host generated antibodies can neutralize viral particles and stop infection by interfering with virion binding to receptors, blocking uptake into cells, preventing uncoating of the genomes in endosomes, or causing aggregation of virus particles. In some instances, enveloped viruses are lysed when antiviral antibodies and serum complement disrupt membranes. In other instances, non-neutralizing antibodies that bind specifically to virus particles, but do not neutralize infectivity may actually enhance infectivity due to antibodies that interact with receptors on macrophages, resulting in virus-antibody complex being brought into the cell by endocytosis. Viral replication then proceeds, as the antibody does not block infectivity, and this pathway may allow entry into cells which normally do not bear specific virus receptors. Moreover, in some situations, host generated antibodies recognizing viral peptides can cross-react with human self-antigens, contributing to the establishment and progression of autoimmune disease. Each of these mechanisms plays a vital role in accounting for the potentiality of disease and/or dysfunction caused by viral exposure.

While the disclosure specifically recites phage display libraries, it is specifically contemplated herein that other display libraries can be used with the methods and assays described herein including, but not limited to, a yeast display library, a bacterial display library, a retroviral display library, a ribosome display library or an mRNA display library. It is within the skills of one of ordinary skill in the art to apply the methods and assays exemplified herein using a phage display library to the use of a different type of display library.

Definitions

As used herein, the term "display library" refers to a library comprising a plurality of peptides derived from a plurality of pathogens that are displayed on the surface of a virus or cell e.g., bacteriophage, yeast, or bacteria. Methods for using such phage, yeast or bacterial display libraries are well known to those of skill in the art.

As used herein, the term "common disease" refers to a subset of subjects having the same or substantially similar diseases; that is, the subjects have the same disease "in common."

As used herein, the term "antibody-peptide complex" refers to a complex formed when an antibody recognizes an epitope on a peptide and binds to the epitope under low or normal stringent conditions. It will be appreciated that an antibody-peptide complex can dissociate under high stringent conditions, such as low or high pH, or high temperatures.

As used herein, the term "to the pathogen from which it is derived" refers to a step of correlating or mapping at least one peptide in an antibody-peptide complex to a sequence in the known sequences of the viruses, thereby identifying the pathogen that comprises the peptide sequence.

As used herein, the term "enriched" indicates that peptides from a given pathogen are represented at a higher proportion in a population of subjects having a common disease or exposed to a pathogen as compared to the general population or a population lacking the common disease or pathogen exposure. In some embodiments, the peptides from a given pathogen in the population of subjects having a common disease are enriched by at least 10% as compared to the general population. In other embodiments, the peptides for a given pathogen are enriched by at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 25-fold, at least 50-fold, at least 100-fold, at least 1000-fold, or more, compared to the general population.

As used herein the term "oligonucleotide primers" refers to nucleic acid sequences that are 5 to 100 nucleotides in length, preferably from 17 to 45 nucleotides, although primers of different length are of use. Primers for synthesizing cDNAs are preferably 10-45 nucleotides, while primers for amplification are preferably about 17-25 nucleotides. Primers useful in the methods described herein are also designed to have a particular melting temperature (Tm) by the method of melting temperature estimation. Commercial programs, including OLIGO™, Primer Design and programs available on the internet, including PRIMER3 and OLIGO CALCULATOR can be used to calculate a Tm of a polynucleotide sequence useful according to the methods and assays described herein. Preferably, the Tm of an amplification primer useful according to the invention, as calculated for example by OLIGO CALCULATOR, is preferably between about 45 and 65° C. In other embodiments, the Tm of the amplification primer is between about 50 and 60° C.

As used herein, the term "sample" refers to a biological material which is isolated from its natural environment and contains at least one antibody. A sample according to the methods described herein, may consist of purified or isolated antibody, or it may comprise a biological sample such as a tissue sample, a biological fluid sample, or a cell sample comprising an antibody. A biological fluid includes, but is not limited to, blood, plasma, sputum, urine, cerebrospinal fluid, lavages, and leukophoresis samples, for example.

As used herein the term "adapter sequence" refers to a nucleic acid sequence appended to a nucleic acid sequence encoding a phage-displayed peptide. In one embodiment, the identical adaptor sequence is appended to the end of each phage-displayed peptide in the phage display library; that is, the adaptor sequence is a common sequence on each nucleic acid of the plurality of nucleic acids encoding a peptide in the phage display library. In one embodiment, the adaptor sequence is of sufficient length to permit annealing of a common PCR primer. For example, adaptor sequences useful with the methods described herein are preferably heterologous or artificial nucleotide sequences of at least 15, and preferably 20 to 30 nucleotides in length. An adaptor sequence as described herein can be, but is not necessarily random.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

Pathogens

Provided herein are phage display libraries that comprise a plurality of peptides derived from one or more pathogens.

As used herein the term "pathogen" refers to an organism, including a microorganism, which causes disease in another organism (e.g., animals and plants) by directly infecting the other organism, or by producing agents that causes disease in another organism (e.g., bacteria that produce pathogenic toxins and the like). As used herein, pathogens include, but are not limited to bacteria, protozoa, fungi, nematodes, viroids and viruses, or any combination thereof, wherein each pathogen is capable, either by itself or in concert with another pathogen, of eliciting disease in vertebrates including but not limited to mammals, and including but not limited to humans. As used herein, the term "pathogen" also encompasses microorganisms which may not ordinarily be pathogenic in a non-immunocompromised host. Specific nonlimiting examples of viral pathogens include Herpes simplex virus (HSV)1, HSV2, Epstein Barr virus (EBV), cytomegalovirus (CMV), human Herpes virus (HEW) 6, HHV7, HHV8, Varicella zoster virus (VZV), hepatitis C, hepatitis B, adenovirus, Eastern Equine Encephalitis Virus (EEEV), West Nile virus (WINE), JC virus (JCV) and BK virus (BKV).

As used herein, the term "microorganism" includes prokaryotic and eukaryotic microbial species from the Domains of Archaea, Bacteria and Eucarya, the latter including yeast and filamentous fungi, protozoa, algae, or higher Protista. The terms "microbial cells" and "microbes" are used interchangeably with the term microorganism.

"Bacteria", or "Eubacteria", refers to a domain of prokaryotic organisms. Bacteria include at least 11 distinct groups as follows: (1) Gram-positive (gram+) bacteria, of which there are two major subdivisions: (i) high G+C group (*Actinomycetes, Mycobacteria, Micrococcus,* others) (ii) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) *Spirochetes* and related species; (5) *Planctomyces*; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema,* and *Fusobacterium*.

"Gram-positive bacteria" include cocci, nonsporulating rods, and sporulating rods. The genera of Gram-positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus,* and *Streptomyces*.

The methods described herein can be used to generate a phage display library comprising peptides from pathogens including, but not limited to pathogens from any of the following genera of viruses: *Adenoviridae, Alfamovirus, Allexivirus, Allolevivirus, Alphacryptovirus, Alphaherpesvirinae, Alphanodavirus, Alpharetrovirus, Alphavirus, Aphthovirus, Apscaviroid, Aquabirnavirus, Aquareovirus, Arenaviridae, Arenavirus, Arteriviridae, Arterivirus, Ascoviridae, Ascovirus, Asfarviridae, Asfivirus, Astroviridae, Astrovirus, Aureusvirus, Avenavirus, Aviadenovirus, Avibirnavirus, Avihepadnavirus, Avipoxvirus, Avsunviroid, Avsunviroidae, Baculoviridae, Badnavirus, Barnaviridae, Barnavirus, Bdellomicrovirus, Begomovirus, Benyvirus, Betacryptovirus, Betaherpesvirinae, Betanodavirus, Betaretrovirus, Betatetravirus, Birnaviridae, Bornaviridae, Bornavirus, Bracovirus, Brevidensovirus, Bromoviridae, Bromovirus, Bunyaviridae, Bunyavirus, Bymovirus,* "c2-like viruses," *Caliciviridae, Capillovirus, Capripoxvirus, Cardiovirus, Carlavirus, Carmovirus,* "Cassava vein mosaic-like viruses," *Caulimoviridae, Caulimovirus, Chlamydiamicrovirus, Chloriridovirus, Chlorovirus, Chordopoxyirinae, Chrysovirus, Circoviridae, Circovirus, Closteroviridae, Closterovirus, Cocadviroid, Coleviroid, Coltivirus, Comoviridae, Comovirus, Coronaviridae, Coronavirus, Corticoviridae, Corticovirus,* "Cricket paralysis-like viruses," *Crinivirus, Cucumovirus, Curtovirus, Cypovirus, Cystoviridae, Cystovirus, Cytomegalovirus, Cytorhabdovirus, Deltarelrovirus, Deltavirus, Densovirinae, Densovirus, Dependovirus, Dianthovirus,* "Ebola-like viruses," *Enamovirus, Enterovirus, Entomobirnavirus, Entomopoxyirinae, Entomopoxvirus A, Entomopoxvirus B,*

*Entomopoxvirus C, Ephemerovirus, Epsilonretrovirus, Errantivirus, Erythrovirus, Fabavirus, Fijivirus, Filoviridae, Flaviviridae, Flavivirus, Foveavirus, Furovirus, Fuselloviridae, Fusellovirus, Gammaherpesvirinae, Gammaretrovirus, Geminiviridae, Giardiavirus, Granulovirus, Hantavirus, Hemivirus, Hepacivirus, Hepadnaviridae,* "Hepatitis E-like viruses," *Hepatovirus, Herpesviridae, Hordeivirus, Hostuviroid, Hypoviridae, Hypovirus, Ichnovirus,* "Ictalurid herpes-like viruses," *Idaeovirus, Ilarvirus,* "Infectious laryngotracheitis-like viruses," *Influenzavirus A, Influenzavirus B, Influenzavirus C, Inoviridae, Inovirus, Ipomovirus, Iridoviridae, Iridovirus, Iteravirus,* "L5-like viruses," *Lagovirus,* "-like viruses," *Leishmaniavirus, Lentivirus, Leporipoxvirus, Leviviridae, Levivirus, Lipothrixviridae, Lipothrixvirus, Luteoviridae, Luteovirus, Lymphocryptovirus, Lymphocystivirus, Lyssavirus, Machlomovirus, Macluravirus, Marafivirus,* "Marburg-like viruses," "Marek's disease-like viruses," *Mastadenovirus, Mastrevirus, Metapneumovirus, Metaviridae, Metavirus, Microviridae, Microvirus, Mitovirus, Molluscipoxvirus, Morbillivirus,* "Mu-like viruses," *Muromegalovirus, Myoviridae, Nairovirus, Nanovirus, Narnaviridae, Narnavirus, Necrovirus, Nepovirus, Nodaviridae,* "Norwalk-like viruses," *Novirhabdovirus, Nucleopolyhedrovirus, Nucleorhabdovirus, Oleavirus, Omegatetravirus, Ophiovirus, Orbivirus, Orthohepadnavirus, Orthomyxoviridae, Orthopoxvirus, Orthoreovirus, Oryzavirus, Ourmiavirus,* "P1-like viruses," "P2-like viruses," "P22-like viruses," *Panicovirus, Papillomaviridae, Papillomavirus, Paramyxoviridae, Paramyxovirinae, Parapoxvirus, Parechovirus, Partitiviridae, Partitivirus, Parvoviridae, Parvoviridae, Parvovirus, Pecluvirus, Pelamoviroid, Pestivirus,* "Petunia vein clearing-like viruses," *Phaeovirus,* "-29-like viruses," "—H-like viruses," *Phlebovirus, Phycodnaviridae, Phytoreovirus, Picornaviridae, Plasmaviridae, Plasmavirus, Plectrovirus, Pneumovirinae, Pneumovirus, Podoviridae, Polerovirus, Polydnaviridae, Polyomaviridae, Polyomavirus, Pomovirus, Pospiviroid, Pospiviroidae, Potexvirus, Potyviridae, Potyvirus, Poxyiridae, Prasinovirus, Prions, Prymnesiovirus, Pseudoviridae, Pseudovirus,* "M1-like viruses", *Ranavirus, Reoviridae, Respirovirus, Retroviridae, Rhabdoviridae, Rhadinovirus, Rhinovirus, Rhizidiovirus,* "Rice tungro bacilliform-like viruses," *Roseolovirus, Rotavirus, Rubivirus, Rubulavirus, Rudiviridae, Rudivirus, Rymovirus,* "Sapporo-like viruses," *Satellites, Sequiviridae, Sequivirus, Simplexvirus, Siphoviridae, Sobermovirus,* "Soybean chlorotic mottle-like viruses," *Spiromicrovirus,* "SP01-like viruses," *Spumavirus, Suipoxvirus,* "Sulfolobus SNDV-like viruses," "T1-like viruses," "T4-like viruses," "T5-like viruses," "T7-like viruses," *Tectiviridae, Tectivirus, Tenuivirus, Tetraviridae, Thogotovirus, Tobamovirus, Tobravirus, Togaviridae, Tombusviridae, Tombusvirus, Torovirus, Tospovirus, Totiviridae, Totivirus, Trichovirus, Tritimovirus, Tymovirus, Umbravirus, Varicellovirus, Varicosavirus, Vesiculovirus, Vesivirus, Viroids, Vitivirus, Wakavirus,* and *Yatapoxvirus.*

The methods described herein can be used to generate a phage display library comprising peptides derived from pathogens including, but not limited to, pathogens from any of the following genera of the domain of Bacteria (or Eubacteria): *Abiotrophia, Acetitomaculum, Acetivibrio, Acetoanaerobium, Acetobacter, Acetobacterium, Acetofilamentum, Acetogenium, Acetohalobium, Acetomicrobium, Acetonema, Acetothermus, Acholeplasma, Achromatium, Achromobacter, Acidaminobacter, Acidaminococcus, Acidimicrobium, Acidiphilium, Acidisphaera, Acidithiobacillus, Acidobacterium, Acidocella, Acidomonas, Acidothermus, Acidovorax, Acinetobacter, Acrocarpospora, Actinoalloteichus, Actinobacillus, Actinobaculum, Actinobispora, Actinocorallia, Actinokineospora, Actinomadura, Actinomyces, Actinoplanes, Actinopolymorpha, Actinopolyspora, Actinopycnidium, Actinosporangium, Actinosynnema, Aegyptianella, Aequorivita, Aerococcus, Aeromicrobium, Aeromonas, Afipia, Agitococcus, Agreia, Agrobacterium, Agrococcus, Agromonas, Agromyces, Ahrensia, Albibacter, Albidovulum, Alcaligenes, Alcalilimnicola, Alcanivorax, Algoriphagus, Alicycliphilus, Alicyclobacillus, Alishewanella, Alistipes, Alkalibacterium, Alkahlimnicola, Alkaliphilus, Alkalispirillum, Alkanindiges, Allisonella, Allochromatium, Allofustis, Alloiococcus, Allomonas, Allorhizobium, Alterococcus, Alteromonas, Alysiella, Amaricoccus, Aminobacter, Aminobacterium, Aminomonas, Ammonifex, Ammomphilus, Amoebobacter, Amorphosporangium, Amphibacillus, Ampullariella, Amycolata, Amycolatopsis, Anaeroarcus, Anaerobacter, Anaerobaculum, Anaerobiospirillum, Anaerobranca, Anaerococcus, Anaerofilum, Anaeroglobus, Anaerolinea, Anaeromusa, Anaeromyxobacter, Anaerophaga, Anaeroplasma, Anaerorhabdus, Anaerosinus, Anaerostipes, Anaerovibrio, Anaerovorax, Anaplasma, Ancalochloris, Ancalomicrobium, Ancylobacter, Aneurinibacillus, Angiococcus, Angulomicrobium, Anoxybacillus, Anoxynatronum, Antarctobacter, Aquabacter, Aquabacterium, Aquamicrobium, Aquaspirillum, Aquifex, Arachnia, Arcanobacterium, Archangium, Arcobacter, Arenibacter, Arhodomonas, Arsenophonus, Arthrobacter, Asaia, Asanoa, Asteroleplasma, Asticcacaulis, Atopobacter, Atopobium, Aurantimonas, Aureobacterium, Azoarcus, Azomonas, Azomonotrichon, Azonexus, Azorhizobium, Azorhizophilus, Azospira, Azospirillum, Azotobacter, Azovibrio, Bacillus, Bacterionema, Bacteriovorax, Bacteroides, Bactoderma, Balnearium, Balneatrix, Bartonella, Bdellovibrio, Beggiatoa, Beijerinckia, Beneckea, Bergeyella, Beutenbergia, Bifidobacterium, Bilophila, Blastobacter, Blastochloris, Blastococcus, Blastomonas, Blattabacterium, Bogoriella, Bordetella, Borrelia, Bosea, Brachybacterium, Brachymonas, Brachyspira, Brackiella, Bradyrhizobium, Branhamella, Brenneria, Brevibacillus, Brevibacterium, Brevinema, Brevundimonas, Brochothrix, Brucella, Brumimicrobium, Buchnera, Budvicia, Bulleidia, Burkholderia, Buttiauxella, Butyrivibrio, Caedibacter, Caenibacterium, Calderobacterium, Caldicellulosiruptor, Caldilinea, Caldimonas, Caldithrix, Caloramator, Caloranaerobacter, Calymmatobacterium, Caminibacter, Caminicella, Campylobacter, Capnocytophaga, Capsularis, Carbophilus, Carboxydibrachium, Carboxydobrachium, Carboxydocella, Carboxydothermus, Cardiobacterium, Camimonas, Carnobacterium, Caryophanon, Caseobacter, Catellatospora, Catenibacterium, Catenococcus, Catenuloplanes, Catonella, Caulobacter, Cedecea, Cellulomonas, Cellulophaga, Cellulosimicrobium, Cellvibrio, Centipeda, Cetobacterium, Chainia, Chelatobacter, Chelatococcus, Chitinophaga, Chlamydia, Chlamydophila, Chlorobaculum, Chlorobium, Chlorojlexus, Chloroherpeton, Chloronema, Chondromyces, Chromatium, Chromobacterium, Chromohalobacter, Chryseobacterium, Chryseomonas, Chrysiogenes, Citricoccus, Citrobacter, Clavibacter, Clevelandina, Clostridium, Cobetia, Coenonia, Collinsella, Colwellia, Comamonas, Conexibacter, Conglomeromonas, Coprobacillus, Coprococcus, Coprothermobacter, Coriobacterium, Corynebacterium, Couchioplanes, Cowdria, Coxiella, Craurococcus, Crenothrix, Crinalium* (not validly published), *Cristispira, Croceibacter, Crocinitomix, Crossiella, Cryobacterium, Cryomorpha, Cryptobacterium, Cryptosporangium, Cupriavidus, Curtobacterium, Cyclobacterium, Cycloclasticus, Cystobacter, Cytophaga, Dactylosporan-* gium, Dechloromonas, Dechlorosoma, Deferribacter, Defluvibacter, Dehalobacter, Dehalospirillum, Deinobacter, Deinococcus, Deleya, Delftia, Demetria, Dendrosporobacter, Denitrobacterium, Denitrovibrio, Dermabacter, Dermacoccus, Dermatophilus, Derxia, Desemzia, Desulfacinum, Desulfitobacterium, Desulfobacca, Desulfobacter, Desulfobacterium, Desulfobacula, Desulfobulbus, Desulfocapsa, Desulfocella, Desulfococcus, Desulfofaba, Desulfofrigus, Desulfofustis, Desulfohalobium, Desulfomicrobium, Desulfomonas, Desulfomonile, Desulfomusa, Desulfonatronovibrio, Desulfonatronum, Desulfonauticus, Desulfonema, Desulfonispora, Desulforegula, Desulforhabdus, Desulforhopalus, Desulfosarcina, Desulfospira, Desulfosporosinus, Desulfotalea, Desulfotignum, Desulfotomaculum, Desulfovibrio, Desulfovirga, Desulfurella, Desulfurobacterium, Desulfuromonas, Desulfuromusa, Dethiosulfovibrio, Devosia, Dialister, Diaphorobacter, Dichelobacter, Dichotomicrobium, Dictyoglomus, Dietzia, Diplocalyx, Dolosicoccus, Dolosigranulum, Dorea, Duganella, Dyadobacter, Dysgonomonas, Ectothiorhodospira, Edwardsiella, Eggerthella, Ehrlichia, Eikenella, Elytrosporangium, Empedobacter, Enhydrobacter, Enhygromyxa, Ensifer, Enterobacter, Enterococcus, Enterovibrio, Entomoplasma, Eperythrozoon, Eremococcus, Erwinia, Erysipelothrix, Erythrobacter, Erythromicrobium, Erythromonas, Escherichia, Eubacterium, Ewingella, Excellospora, Exiguobacterium, Facklamia, Faecalibacterium, Faenia, Falcivibrio, Ferribacterium, Ferrimonas, Fervidobacterium, Fibrobacter, Filibacter, Filifactor, Filobacillus, Filomicrobium, Finegoldia, Flammeovirga, Flavimonas, Flavobacterium, Flectobacillus, Flexibacter, Flexistipes, Flexithrix, Fluoribacter, Formivibrio, Francisella, Frankia, Frateuria, Friedmanniella, Frigoribacterium, Fulvimarina, Fulvimonas, Fundibacter, Fusibacter, Fusobacterium, Gallibacterium, Gallicola, Gallionella, Garciella, Gardnerella, Gelidibacter, Gelria, Gemella, Gemmata, Gemmatimonas, Gemmiger, Gemmobacter, Geobacillus, Geobacter, Geodermatophilus, Georgenia, Geothrix, Geotoga, Geovibrio, Glaciecola, Globicatella, Gluconacetobacter, Gluconoacetobacter, Gluconobacter, Glycomyces, Gordonia, Gordonia, Gracilibacillus, Grahamella, Granulicatella, Grimontia, Haemobartonella, Haemophilus, Hafnia, Hahella, Halanaerobacter, Halanaerobium, Haliangium, Haliscomenobacter, Hallella, Haloanaerobacter, Haloanaerobium, Halobacillus, Halobacteroides, Halocella, Halochromatium, Haloincola, Halomicrobium, Halomonas, Halonatronum, Halorhodospira, Halospirulina, Halothermothrix, Halothiobacillus, Halovibrio, Helcococcus, Heliobacillus, Helicobacter, Heliobacterium, Heliophilum, Heliorestis, Heliothrix, Herbaspirillum, Herbidospora, Herpetosiphon, Hippea, Hirschia, Histophilus, Holdemania, Hollandina, Holophaga, Holospora, Hongia, Hydrogenobacter, Hydrogenobaculum, Hydrogenophaga, Hydrogenophilus, Hydrogenothermus, Hydrogenovibrio, Hymenobacter, Hyphomicrobium, Hyphomonas, Ideonella, Idiomarina, Ignavigranum, Ilyobacter, Inquilinus, Intrasporangium, Iodobacter, Isobaculum, Isochromatium, Isosphaera, Janibacter, Jannaschia, Janthinobacterium, Jeotgalibacillus, Jeotgalicoccus, Johnsonella, Jonesia, Kerstersia, Ketogulonicigenium, Ketogulonigenium, Kibdelosporangium, Kineococcus, Kineosphaera, Kineosporia, Kingella, Kitasatoa, Kitasatospora, Kitasatosporia, Klebsiella, Kluyvera, Knoellia, Kocuria, Koserella, Kozakia, Kribbella, Kurthia, Kutzneria, Kytococcus, Labrys, Lachnobacterium, Lachnospira, Lactobacillus, Lactococcus, Lactosphaera, Lamprobacter, Lamprocystis, Lampropedia, Laribacter, Lautropia, Lawsonia, Lechevalieria, Leclercia, Legionella, Leifsonia, Leisingera, Leminorella, Lentibacillus, Lentzea, Leptonema, Leptospira, Leptospirillum, Leptothrix, Leptotrichia, Leucobacter, Leuconostoc, Leucothrix, Levinea, Lewinella, Limnobacter, Limnothrix, Listeria, Listonella, Lonepinella, Longispora, Lucibacterium, Luteimonas, Luteococcus, Lysobacter, Lyticum, Macrococcus, Macromonas, Magnetospirillum, Malonomonas, Mannheimia, Maricaulis, Marichromatium, Marinibacillus, Marinilabilia, Marinilactibacillus, Marinithermus, Marinitoga, Marinobacter, Marinobacterium, Marinococcus, Marinomonas, Marinospirillum, Marmoricola, Massilia, Megamonas, Megasphaera, Meiothermus, Melissococcus, Melittangium, Meniscus, Mesonia, Mesophilobacter, Mesoplasma, Mesorhizobium, Methylarcula, Methylobacillus, Methylobacter, Methylobacterium, Methylocaldum, Methylocapsa, Methylocella, Methylococcus, Methylocystis, Methylomicrobium, Methylomonas, Methylophaga, Methylophilus, Methylopila, Methylorhabdus, Methylosarcina, Methylosinus, Methylosphaera, Methylovorus, Micavibrio, Microbacterium, Microbispora, Microbulbifer, Micrococcus, Microcyclus, Microcystis, Microellobosporia, Microlunatus, Micromonas, Micromonospora, Micropolyspora, Micropruina, Microscilla, Microsphaera, Microtetraspora, Microvirga, Microvirgula, Mitsuokella, Mobiluncus, Modestobacter, Moellerella, Mogibacterium, Moorella, Moraxella, Morganella, Moritella, Morococcus, Muricauda, Muricoccus, Mycetocola, Mycobacterium, Mycoplana, Mycoplasma, Myroides, Myxococcus, Nannocystis, Natroniella, Natronincola, Natronoincola, Nautilia, Neisseria, Neochlamydia, Neorickettsia, Neptunomonas, Nesterenkonia, Nevskia, Nitrobacter, Nitrococcus, Nitrosococcus, Nitrosolobus, Nitrosomonas, Nitrosospira, Nitrospina, Nitrospira, Nocardia, Nocardioides, Nocardiopsis, Nonomuraea, Nonomuria, Novosphingobium, Obesumbacterium, Oceanicaulis, Oceanimonas, Oceanisphaera, Oceanithermus, Oceanobacillus, Oceanobacter, Oceanomonas, Oceanospirillum, Ochrobactrum, Octadecabacter, Oenococcus, Oerskovia, Okibacterium, Oleiphilus, Oleispira, Oligella, Oligotropha, Olsenella, Opitutus, Orenia, Oribaculum, Orientia, Ornithinicoccus, Ornithinimicrobium, Ornithobacterium, Oscillochloris, Oscillospira, Oxalicibacterium, Oxalobacter, Oxalophagus, Oxobacter, Paenibacillus, Pandoraea, Pannonibacter, Pantoea, Papillibacter, Parachlamydia, Paracoccus, Paracraurococcus, Paralactobacillus, Paraliobacillus, Parascardovia, Parvularcula, Pasteurella, Pasteuria, Paucimonas, Pectinatus, Pectobacterium, Pediococcus, Pedobacter, Pedomicrobium, Pelczaria, Pelistega, Pelobacter, Pelodictyon, Pelospora, Pelotomaculum, Peptococcus, Peptoniphilus, Peptostreptococcus, Persephonella, Persicobacter, Petrotoga, Pfennigia, Phaeospirillum, Phascolarctobacterium, Phenylobacterium, Phocoenobacter, Photobacterium, Photorhabdus, Phyllobacterium, Pigmentiphaga, Pilimelia, Pillotina, Pimelobacter, Pirella, Pirellula, Piscirickettsia, Planctomyces, Planktothricoides, Planktothrix, Planobispora, Planococcus, Planomicrobium, Planomonospora, Planopolyspora, Planotetraspora, Plantibacter, Pleisomonas, Plesiocystis, Plesiomonas, Polaribacter, Polaromonas, Polyangium, Polynucleobacter, Porphyrobacter, Porphyromonas, Pragia, Prauserella, Prevotella, Prochlorococcus, Prochloron, Prochlorothrix, Prolinoborus, Promicromonospora, Propionibacter, Propionibacterium, Propionicimonas, Propioniferax, Propionigenium, Propionimicrobium, Propionispira, Propionispora, Propionivibrio, Prosthecobacter, Prosthecochloris, Prosthecomicrobium, Proteus, Protomonas, Providencia, Pseudaminobacter, Pseudoalteromonas, Pseudoamycolata, Pseudobutyrivibrio, Pseudocaedibacter, Pseudomonas,

*Pseudonocardia, Pseudoramibacter, Pseudorhodobacter, Pseudospirillum, Pseudoxanthomonas, Psychrobacter, Psychroflexus, Psychromonas, Psychroserpens, Quadricoccus, Quinella, Rahnella, Ralstonia, Ramlibacter, Raoultella, Rarobacter, Rathayibacter, Reichenbachia, Renibacterium, Rhabdochromatium, Rheinheimera, Rhizobacter, Rhizobium, Rhizomonas, Rhodanobacter, Rhodobaca, Rhodobacter, Rhodobium, Rhodoblastus, Rhodocista, Rhodococcus, Rhodocyclus, Rhodoferax, Rhodoglobus, Rhodomicrobium, Rhodopila, Rhodoplanes, Rhodopseudomonas, Rhodospira, Rhodospirillum, Rhodothalassium, Rhodothermus, Rhodovibrio, Rhodovulum, Rickettsia, Rickettsiella, Riemerella, Rikenella, Rochalimaea, Roseateles, Roseburia, Roseibium, Roseiflexus, Roseinatronobacter, Roseivivax, Roseobacter, Roseococcus, Roseomonas, Roseospira, Roseospirillum, Roseovarius, Rothia, Rubrimonas, Rubritepida, Rubrivivax, Rubrobacter, Ruegeria, Rugamonas, Ruminobacter, Ruminococcus, Runella, Saccharobacter, Saccharococcus, Saccharomonospora, Saccharopolyspora, Saccharospirillum, Saccharothrix, Sagittula, Salana, Salegentibacter, Salibacillus, Salinibacter, Salinibacterium, Salinicoccus, Salinisphaera, Salinivibrio, Salmonella, Samsonia, Sandaracinobacter, Sanguibacter, Saprospira, Sarcina, Sarcobium, Scardovia, Schineria, Schlegelella, Schwartzia, Sebaldella, Sedimentibacter, Selenihalanaerobacter, Selenomonas, Seliberia, Serpens, Serpula, Serpulina, Serratia, Shewanella, Shigella, Shuttleworthia, Silicibacter, Simkania, Simonsiella, Sinorhizobium, Skermanella, Skermania, Slackia, Smithella, Sneathia, Sodalis, Soehngenia, Solirubrobacter, Solobacterium, Sphaerobacter, Sphaerotilus, Sphingobacterium, Sphingobium, Sphingomonas, Sphingopyxis, Spirilliplanes, Spirillospora, Spirillum, Spirochaeta, Spiroplasma, Spirosoma, Sporanaerobacter, Sporichthya, Sporobacter, Sporobacterium, Sporocytophaga, Sporohalobacter, Sporolactobacillus, Sporomusa, Sporosarcina, Sporotomaculum, Staleya, Staphylococcus, Stappia, Starkeya, Stella, Stenotrophomonas, Sterolibacterium, Stibiobacter, Stigmatella, Stomatococcus, Streptacidiphilus, Streptimonospora, Streptoalloteichus, Streptobacillus, Streptococcus, Streptomonospora, Streptomyces: S. abikoensis, S. erumpens, S. erythraeus, S. michiganensis, S. microflavus, S. zaomyceticus, Streptosporangium, Streptoverticillium, Subtercola, Succiniclasticum, Succinimonas, Succinispira, Succinivibrio, Sulfitobacter, Sulfobacillus, Sulfurihydrogenibium, Sulfitrimonas, Sulfitrospirillum, Sutterella, Suttonella, Symbiobacterium, Symbiotes, Synergistes, Syntrophobacter, Syntrophobotulus, Syntrophococcus, Syntrophomonas, Syntrophosphora, Syntrophothermus, Syntrophus, Tannerella, Tatlockia, Tatumella, Taylorella, Tectibacter, Teichococcus, Telluria, Tenacibaculum, Tepidibacter, Tepidimonas, Tepidiphilus, Terasakiella, Teredinibacter, Terrabacter, Terracoccus, Tessaracoccus, Tetragenococcus, Tetrasphaera, Thalassomonas, Thalassospira, Thauera, Thermacetogenium, Thermaerobacter, Thermanaeromonas, Thermanaerovibrio, Thermicanus, Thermithiobacillus, Thermoactinomyces, Thermoanaerobacter, Thermoanaerobacterium, Thermoanaerobium, Thermobacillus, Thermobacteroides, Thermobifida, Thermobispora, Thermobrachium, Thermochromatium, Thermocrinis, Thermocrispum, Thermodesulfobacterium, Thermodesulforhabdus, Thermodesulfovibrio, Thermohalobacter, Thermohydrogenium, Thermoleophilum, Thermomicrobium, Thermomonas, Thermomonospora, Thermonema, Thermosipho, Thermosyntropha, Thermoterrabacterium, Thermothrix, Thermotoga, Thermovenabulum, Thermovibrio, Thermus, Thialkalicoccus, Thialkalimicrobium, Thialkalivibrio, Thioalkalicoccus, Thioalkalimicrobium, Thioalkalispira, Thioalkalivibrio, Thiobaca, Thiobacillus, Thiobacterium, Thiocapsa, Thiococcus, Thiocystis, Thiodictyon, Thioflavicoccus, Thiohalocapsa, Thiolamprovum, Thiomargarita, Thiomicrospira, Thiomonas, Thiopedia, Thioploca, Thiorhodococcus, Thiorhodospira, Thiorhodovibrio, Thiosphaera, Thiospira, Thiospirillum, Thiothrix, Thiovulum, Tindallia, Tissierella, Tistrella, Tolumonas, Toxothrix, Trabulsiella, Treponema, Trichlorobacter, Trichococcus, Tropheryma, Tsukamurella, Turicella, Turicibacter, Tychonema, Ureaplasma, Ureibacillus, Vagococcus, Vampirovibrio, Varibaculum, Variovorax, Veillonella, Verrucomicrobium, Verrucosispora, Vibrio, Victivallis, Virgibacillus, Virgisporangium, Virgosporangium, Vitellibacter, Vitreoscilla, Vogesella, Volcaniella, Vulcanithermus, Waddlia, Weeksella, Weissella, Wigglesworthia, Williamsia, Wolbachia, Wolinella, Xanthobacter, Xanthomonas, Xenophilus, Xenorhabdus, Xylanimonas, Xylella, Xylophilus, Yersinia, Yokenella, Zavarzinia, Zobellia, Zoogloea, Zooshikella, Zymobacter, Zymomonas,* and *Zymophilus.*

Production of a Phage Display Library

General methods for producing a phage display library are known to those of skill in the art and/or are described in e.g., Larman et al. (2011) *Nature Biotechnology* 29(6):535-541, which is incorporated herein by reference in its entirety.

Contemplated herein are phage display libraries that comprise a plurality of peptides derived from a plurality of pathogens, such as bacteria, fungi, or viruses. In one embodiment, it is contemplated herein that the plurality of peptides will represent a substantially complete set of peptides from a group of viruses, bacteria, or fungi (e.g., all pathogenic viruses, bacteria or fungi). In one embodiment, the phage display library comprises a substantially complete set of peptides from viruses known to infect humans (or a subgroup thereof). Similarly, phage display libraries comprising a substantially complete set of peptides from pathogenic bacteria (or a subgroup thereof) or pathogenic fungi (or a subgroup thereof) are also contemplated herein. As used herein, the term "subgroup" refers to a related grouping of viruses, bacteria or fungi that would benefit from simultaneous testing. For example, one of skill in the art can generate a phage display library comprising a substantially complete set of peptides from a genus of pathogens (e.g., a subgroup of virus, such as the Herpes genus). Such a library would permit one of skill in the art to distinguish between highly related pathogens in an antibody sample.

In some embodiments, the phage display library comprises less than 10,000 peptide sequences. In other embodiments, the phage display library comprises less than 9000, less than 8000, less than 7000, less than 6000, less than 5000, less than 4000, less than 3000, less than 2000, less than 1000, less than 750, less than 500, less than 250, less than 100, less than 50 or less than 25 peptide sequences. In other embodiments, the phage display library comprises at least 100, at least 200, at least 500, at least 1000, at least 5000, at least 10,000 peptide sequences or more. It will be appreciated by one of ordinary skill in the art that as the length of the individual peptide sequences increase, the total number of peptide sequences in the library can decrease without loss of any pathogen sequences (and vice versa).

In some embodiments, the phage display library comprises peptides derived from at least 10 protein sequences (e.g., viral protein sequences), at least 20 protein sequences, at least 30 protein sequences, at least 40 protein sequences, at least 50 protein sequences, at least 60 protein sequences, at least 70 protein sequences, at least 80 protein sequences, at least 90 protein sequences, at least 100 protein sequences, at least 200 protein sequences, at least 300 protein sequences, at least 400 protein sequences, at least 500 protein sequences, at least 600 protein sequences, at least 700 protein sequences, at least 800 protein sequences, at least 900 protein sequences, at least 1000 protein sequences, at least 2000 protein sequences, at least 3000 protein sequences, at least 4000 protein sequences, at least 5000 protein sequences, at least 6000 protein sequences, at least 6500 protein sequences, at least 7000 protein sequences, at least 7500 protein sequences, at least 8000 protein sequences, at least 8500 protein sequences, at least 9000 protein sequences, at least 10,000 protein sequences or more.

In some embodiments, the phage display library comprises a plurality of proteins sequence that have less than 90% shared identity; in other embodiments the plurality of protein sequences have less than 85% shared identity, less than 80% shared identity, less than 75% shared identity, less than 70% shared identity, less than 65% shared identity, less than 60% shared identity, less than 55% shared identity, less than 50% shared identity or even less.

In some embodiments, the phage display library comprises protein sequences from at least 3 unique pathogens or at least 5 unique pathogens (e.g., 5 unique viruses, 5 unique bacteria, or 5 unique fungi); in other embodiments the library comprises protein sequences from at least 10, at least 20, at least 50, at least 75, at least 100, at least 200, at least 300, at least 400, at least 500, at least 600, at least 700, at least 800, at least 900, at least 1000 unique pathogens up to and including protein sequences from all viruses, bacteria, or fungi known to cause disease in a human or other mammal.

In some embodiments, the protein sequences of the phage display library are at least 10 amino acids long; in other embodiments the protein sequences are at least 20, at least 30, at least 40, at least 50, at least 60, at least 70, at least 80, at least 90, at least 100, at least 150, at least 200, at least 250, at least 300, at least 350, at least 400, at least 450 amino acids or more in length.

In some embodiments, each peptide of the phage library will overlap at least one other peptide by at least 5 amino acids. In other embodiments, each peptide of the phage library will overlap at least one other peptide by at least 10, at least 15, at least 20, at least 21, at least 22, at least 23, at least 24, at least 25, at least 26, at least 27, at least 28, at least 29, at least 30, at least 32, at least 35, at least 40 amino acids or more.

Reaction Samples

As used herein, the term "reaction sample" refers to a sample that, at a minimum, comprises a phage display library, for example, the phage display library described herein. The reaction sample can also comprise additional buffers, salts, osmotic agents, etc. to facilitate the formation of complexes between the peptides in the phage display library when the reaction sample is contacted with a biological sample comprising an antibody. A "biological sample" as that term is used herein refers to a fluid or tissue sample derived from a subject that comprises or is suspected of comprising at least one antibody.

A biological sample can be obtained from any organ or tissue in the individual to be tested, provided that the biological sample comprises, or is suspected of comprising, an antibody. Typically the biological sample will comprise a blood sample, however other biological samples are contemplated herein, for example, cerebrospinal fluid.

In some embodiments, a biological sample is treated to remove cells or other biological particulates. Methods for removing cells from a blood or other biological sample are well known in the art and can include e.g., centrifugation, ultrafiltration, immune selection, or sedimentation etc. Antibodies can be detected from a biological sample or a sample that has been treated as described above or as known to those of skill in the art. Some non-limiting examples of biological samples include a blood sample, a urine sample, a semen sample, a lymphatic fluid sample, a cerebrospinal fluid sample, a plasma sample, a serum sample, a pus sample, an amniotic fluid sample, a bodily fluid sample, a stool sample, a biopsy sample, a needle aspiration biopsy sample, a swab sample, a mouthwash sample, a cancer sample, a tumor sample, a tissue sample, a cell sample, a synovial fluid sample, or a combination of such samples. For the methods described herein, it is preferred that a biological sample is from whole blood, plasma, cerebral spinal fluid, serum, and/or urine. In one embodiment, the biological sample is cerebrospinal fluid.

In some embodiments, samples can be obtained from an individual with a disease or pathological condition. In one embodiment, the disease or pathological condition is one that is suspected of having a common viral, bacterial or fungal origin. Some exemplary disease or pathological conditions include, but not limited to: a blood disorder, blood lipid disease, autoimmune disease, bone or joint disorder, a cardiovascular disorder, respiratory disease, endocrine disorder, immune disorder, infectious disease, muscle wasting and whole body wasting disorder, neurological disorders including neurodegenerative and/or neuropsychiatric diseases, skin disorder, kidney disease, scleroderma, stroke, hereditary hemorrhage telangiectasia, diabetes (e.g., Type I or Type II diabetes), disorders associated with diabetes (e.g., PVD), hypertension, Gaucher's disease, Kawasaki disease, Bell's palsy, Meniere's disease, juvenile idiopathic arthritis, chronic fatigue syndrome, Gulf War illness, Myasthenia Gravis, IgG4 disease, cystic fibrosis, sickle cell anemia, liver disease, pancreatic disease, eye, ear, nose and/or throat disease, diseases affecting the reproductive organs, gastrointestinal diseases (including diseases of the colon, diseases of the spleen, appendix, gall bladder, and others) and the like. For further discussion of human diseases, see Mendelian Inheritance in Man: A Catalog of Human Genes and Genetic Disorders by Victor A. McKusick (12th Edition (3 volume set) June 1998, Johns Hopkins University Press, ISBN: 0801857422), the entirety of which is incorporated herein. Preferably, samples from a normal demographically matched individual and/or from a non-disease sample from a patient having the disease are used in the analysis to provide controls. The samples can comprise a plurality of cells from individuals sharing a trait. For example, the trait shared can be gender, age, pathology, predisposition to a pathology, exposure to an infectious disease (e.g., HIV), kinship, death from the same disease, treatment with the same drug, exposure to chemotherapy, exposure to radiotherapy, exposure to hormone therapy, exposure to surgery, exposure to the same environmental condition (e.g., such as carcinogens, pollutants, asbestos, TCE, perchlorate, benzene, chloroform, nicotine and the like), the same genetic alteration or group of alterations, expression of the same gene or sets of genes (e.g., samples can be from individuals sharing a common haplotype, such as a particular set of HLA alleles), and the like.

Removal of Unbound Phage

In some embodiments, the methods and assays described herein comprise a step of contacting modified bacteriophage or the phage display library as described herein with a biological sample that comprises, or is suspected of comprising, at least one antibody. Any antiviral antibodies present in the biological sample will bind to bacteriophage(s) that display the cognate antigen.

In certain embodiments, it is desirable to separate the bacteriophage(s) bound to an antibody in the biological sample from any free bacteriophage(s) that are not bound to an antibody in the sample. In one embodiment, antibodies from the reaction sample are immobilized on a solid support to permit one to separate out the unbound phage. Antibody immobilization can be achieved using methods routine to those of ordinary skill in the art. Essentially any method that permits one to specifically immobilize IgM, IgA, or IgG subclasses (e.g., IgG4) can be used to immobilize antibodies from the sample, including antibodies that are complexed to one or more bacteriophage. In some embodiments, Protein A, Protein G or a combination thereof is/are used to immobilize the antibody to permit removal of unbound phage. Such methods are known to those of ordinary skill in the art and as such are not described in detail herein.

In some embodiments, the peptide or protein used to immobilize antibodies from the reaction mixture can be attached to a solid support, such as, for example, magnetic beads (e.g., micron-sized magnetic beads), Sepharose beads, agarose beads, a nitrocellulose membrane, a nylon membrane, a column chromatography matrix, a high performance liquid chromatography (HPLC) matrix or a fast performance liquid chromatography (FPLC) matrix for purification. For example, the reaction mixture comprising bacteriophage and antibodies can be contacted with magnetic beads coated with Protein A and/or Protein G. The Protein A and G will bind to antibodies in the mixture and immobilize them on the beads. This process also immobilizes any phage particles bound by the antibodies. In one embodiment, a magnet can be used to separate the immobilized phage from unbound phage.

As used herein, the term "Magnetic bead" means any solid support that is attracted by a magnetic field; such solid supports include, without limitation, DYNABEADS™, BIOMAG™ Streptavidin, MPG7 Streptavidin, Streptavidin MAGNESPHERE™, Streptavidin Magnetic Particles, AFFINMP™, any of the MAGA™ line of magnetizable particles, BIOMAG™ Superparamagnetic Particles, or any other magnetic bead to which a molecule (e.g., an oligonucleotide primer) may be attached or immobilized.

Peptide Detection

Following a step to remove any unbound phage, the peptides in the bound phage/antibody complexes can be identified using e.g., PCR. Although not necessary, the bound phage/antibody complexes can first be released from the solid support using appropriate conditions e.g., temperature, pH, etc. In some embodiments, the sample is subjected to conditions that will permit lysis of the phage (e.g., heat denaturation). In one embodiment, the nucleic acids from the lysed phage is subjected to an amplification reaction, such as a PCR reaction. In one embodiment, the nucleic acids encoding a phage-displayed peptide comprise a common adapter sequence for PCR amplification. In such embodiments, a PCR primer is designed to bind to the common adapter sequence for amplification of the DNA corresponding to a phage-displayed peptide.

In some embodiments, a detectable label is used in the amplification reaction to permit detection of different amplification products. As used herein, "label" or "detectable label" refers to any atom or molecule which can be used to provide a detectable (preferably quantifiable) signal, and which can be operatively linked to a polynucleotide, such as a PCR primer. Labels may provide signals detectable by fluorescence, radioactivity, colorimetry, gravimetry, X-ray diffraction or absorption, magnetism, enzymatic activity, mass spectrometry, binding affinity, hybridization radiofrequency, nanocrystals and the like. A primer of the present invention may be labeled so that the amplification reaction product may be "detected" by "detecting" the detectable label. "Qualitative or quantitative" detection refers to visual or automated assessments based upon the magnitude (strength) or number of signals generated by the label. A labeled polynucleotide (e.g., an oligonucleotide primer) according to the methods of the invention can be labeled at the 5' end, the 3' end, or both ends, or internally. The label can be "direct", e.g., a dye, or "indirect", e.g., biotin, digoxin, alkaline phosphatase (AP), horse radish peroxidase (HRP). For detection of "indirect labels" it is necessary to add additional components such as labeled antibodies, or enzyme substrates to visualize the captured, released, labeled polynucleotide fragment. In a preferred embodiment, an oligonucleotide primer is labeled with a fluorescent label. Suitable fluorescent labels include fluorochromes such as rhodamine and derivatives (such as Texas Red), fluorescein and derivatives (such as 5-bromomethyl fluorescein), Lucifer Yellow, IAEDANS, 7-Me.sub.2N-coumarin-4-acetate, 7-OH-4-CH$_3$-coumarin-3-acetate, 7-NH.sub.2-4-CH$_3$-coumarin-3-acetate (AMCA), monobromobimane, pyrene trisulfonates, such as Cascade Blue, and monobromorim-ethyl-ammoniobimane (see for example, DeLuca, Immunofluorescence Analysis, in Antibody As a Tool, Marchalonis, et al., eds., John Wiley & Sons, Ltd., (1982), which is incorporated herein by reference).

The methods described herein can benefit from the use of labels including, e.g., fluorescent labels. In one aspect, the fluorescent label can be a label or dye that intercalates into or otherwise associates with amplified (usually double-stranded) nucleic acid molecules to give a signal. One stain useful in such embodiments is SYBR Green (e.g., SYBR Green I or II, commercially available from Molecular Probes Inc., Eugene, Oreg.). Others known to those of skill in the art can also be employed in the methods described herein. An advantage of this approach is reduced cost relative to the use of, for example, labeled nucleotides.

As used herein, the term "amplified product" refers to polynucleotides which are copies of a portion of a particular polynucleotide sequence and/or its complementary sequence, which correspond in nucleotide sequence to the template polynucleotide sequence and its complementary sequence. An "amplified product," can be DNA or RNA, and it may be double-stranded or single-stranded.

Exemplary Methods for Peptide Detection

In an exemplary embodiment, the phage are lysed by heat denaturation and PCR is used to amplify the DNA region corresponding to the displayed peptide sequence. One of the PCR primers contains a common adaptor sequence which can be amplified in a second PCR reaction by another set of primers to prepare the DNA for ILLUMINA™ high throughput sequence. Unique barcoded oligonucleotides in the second PCR reaction are used to amplify different samples and pool them together in one sequencing run to e.g., reduce cost and/or permit simultaneous detection of multiple phage-displayed peptides.

High-Throughput Systems

In certain embodiments, the detection of a phage-displayed peptide comprises high throughput detection of a plurality of peptides simultaneously, or near simultaneously. In some embodiments, the high-throughput systems use methods similar to DNA sequencing techniques.

A number of DNA sequencing techniques are known in the art, including fluorescence-based sequencing methodologies (See, e.g., Birren et al., Genome Analysis: Analyzing DNA, 1, Cold Spring Harbor, N.Y.). In some embodiments, automated sequencing techniques understood in the art are utilized. In some embodiments, the high-throughput systems described herein use methods that provide parallel sequencing of partitioned amplicons (e.g., WO2006084132). In some embodiments, DNA sequencing is achieved by parallel oligonucleotide extension (See, e.g., U.S. Pat. Nos. 5,750, 341, and 6,306,597). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803), the 454 picotiter pyrosequencing technology (Margulies et al., 2005 Nature 437, 376-380; US 20050130173), the Solexa single base addition technology (Bennett et al., 2005, Pharmacogenomics, 6, 373-382; U.S. Pat. Nos. 6,787,308; 6,833,246), the Lynx massively parallel signature sequencing technology (Brenner et al. (2000). Nat. Biotechnol. 18:630-634; U.S. Pat. Nos. 5,695,934; 5,714, 330), and the Adessi PCR colony technology (Adessi et al. (2000). Nucleic Acid Res. 28, E87; WO 00018957).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7:287-296). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by ILLUMINA™, and the Supported Oligonucleotide Ligation and Detection™ (SOLiD) platform commercialized by APPLIED BIOSYSTEMS™. Non-amplification approaches, also known as single-molecule sequencing, are exemplified by the HELISCOPE™ platform commercialized by HELICOS BIOSYSTEMS™, and emerging platforms commercialized by VISIGEN™, OXFORD NANOPORE TECHNOLOGIES LTD., and PACIFIC BIOSCIENCES™, respectively.

In pyrosequencing (Voelkerding et al, Clinical Chem., 55: 641-658, 2009; MacLean et al., Nature Rev. Microbial., 7:287-296; U.S. Pat. Nos. 6,210,891; 6,258,568), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the SOLEXA/ILLUMINA platform (Voelkerding et al., Clinical Chem., 55. 641-658, 2009; MacLean et al., Nature Rev. Microbial., 7:287-296; U.S. Pat. Nos. 6,833,246; 7,115, 400; 6,969,488), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLID™ technology (Voelkerding et al., Clinical Chem., 55: 641-658, 2009; MacLean et al., Nature Rev. Microbial., 7:287-296; U.S. Pat. Nos. 5,912,148; 6,130,073) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLID™ system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (see, e.g., Astier et al., J. Am. Chem. Soc. 2006 Feb. 8; 128(5)1705-10). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HELISCOPE™ by HELICOS BIOSCIENCES™ is employed (Voelkerding et al., Clinical Chem., 55. 641-658, 2009; MacLean et al., Nature Rev. Microbial, 7:287-296; U.S. Pat. Nos. 7,169,560; 7,282,337; 7,482,120; 7,501,245; 6,818,395; 6,911,345; 7,501,245). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is about 99.6% for 50 base reads, with ~100 Mb generated per run. The read-length is 100 base pairs. The accuracy for homopolymer repeats of 5 repeats in length is ~98%.

Another exemplary nucleic acid sequencing approach that CAN be adapted for use with the methods described herein was developed by STRATOS GENOMICS, Inc. and involves the use of XPANDOMERS™. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an XPANDOMER™ of a length longer than the plurality of the subunits of the daughter strand. The XPANDOMER™ typically includes the tethers and reporter elements for parsing genetic information in a sequence corresponding to the contiguous nucleotide sequence of all or a portion of the target nucleic acid. Reporter elements of the XPANDOMER™ are then detected. Additional details relating to XPANDOMER™-based approaches are described in, for example, U.S. Pat. Pub No. 20090035777, entitled "HIGH THROUGHPUT NUCLEIC ACID SEQUENCING BY EXPANSION," filed Jun. 19, 2008, which is incorporated herein in its entirety.

Other emerging single molecule sequencing methods include real-time sequencing by synthesis using a VISIGEN™ platform (Voelkerding et al., *Clinical Chem.*, 55: 641-58, 2009; U.S. Pat. No. 7,329,492; U.S. patent application Ser. No. 11/671,956; U.S. patent application Ser. No. 11/781,166) in which immobilized, primed DNA template is subjected to strand extension using a fluorescently-modified polymerase and florescent acceptor molecules, resulting in detectible fluorescence resonance energy transfer (FRET) upon nucleotide addition.

Another real-time single molecule sequencing system developed by PACIFIC BIOSCIENCES™ (Voelkerding et al., *Clinical Chem.*, 55. 641-658, 2009; MacLean et al., *Nature Rev.* Microbiol., 7:287-296; U.S. Pat. Nos. 7,170, 050; 7,302,146; 7,313,308; 7,476,503) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that can be adapted for use with the methods described herein include, for example, U.S. Pat. Nos. 7,405,281, 7,315,019, 7,313,308, 7,302,146, 7,170,050, U.S. Pat. Pub. Nos. 20080212960, 20080206764, 20080199932, 20080176769, 20080176316, 20080176241, 20080165346, 20080160531, 20080157005, 20080153100, 20080153095, 20080152281, 20080152280, 20080145278, 20080128627, 20080108082, 20080095488, 20080080059, 20080050747, 20080032301, 20080030628, 20080009007, 20070238679, 20070231804, 20070206187, 20070196846, 20070188750, 20070161017, 20070141598, 20070134128, 20070128133, 20070077564, 20070072196, 20070036511, and Korlach et al. (2008) *PNAS* 105(4): 1176-81, all of which are herein incorporated by reference in their entireties.

Subsequently, in some embodiments, the data produced comprises sequence data from multiple barcoded DNAs. Using the known association between the barcode and the source of the DNA, the data can be deconvoluted to assign sequences to the source subjects, samples, organisms, etc. The sequences are mapped, in some embodiments, to a reference DNA sequence (e.g., a chromosome) and genotypes are assigned to the source subjects, samples, organisms, etc., e.g., by modeling, e.g., by a Hidden Markov Model.

Some embodiments provide a processor, data storage, data transfer, and software comprising instructions to assign genotypes. Some embodiments of the technology provided herein further comprise functionalities for collecting, storing, and/or analyzing data. For example, some embodiments comprise the use of a processor, a memory, and/or a database for, e.g., storing and executing instructions, analyzing data, performing calculations using the data, transforming the data, and storing the data. In some embodiments, the processor is configured to calculate a function of data derived from the sequences and/or genotypes determined. In some embodiments, the processor performs instructions in software configured for medical or clinical results reporting and in some embodiments the processor performs instructions in software to support non-clinical results reporting.

In some embodiments, the detection of a phage-displayed peptide comprises PCR with barcoded oligonucleotides. As used herein, the term "barcode" refers to a unique oligonucleotide sequence that allows a corresponding nucleic acid base and/or nucleic acid sequence to be identified. In certain aspects, the nucleic acid base and/or nucleic acid sequence is located at a specific position on a larger polynucleotide sequence (e.g., a polynucleotide covalently attached to a bead). In certain embodiments, barcodes can each have a length within a range of from 4 to 36 nucleotides, or from 6 to 30 nucleotides, or from 8 to 20 nucleotides. In certain aspects, the melting temperatures of barcodes within a set are within 10° C. of one another, within 5° C. of one another, or within 2° C. of one another. In other aspects, barcodes are members of a minimally cross-hybridizing set. That is, the nucleotide sequence of each member of such a set is sufficiently different from that of every other member of the set that no member can form a stable duplex with the complement of any other member under stringent hybridization conditions. In one aspect, the nucleotide sequence of each member of a minimally cross-hybridizing set differs from those of every other member by at least two nucleotides. Barcode technologies are known in the art and are described in e.g., Winzeler et al. (1999) *Science* 285:901; Brenner (2000) *Genome Biol.* 1:1 Kumar et al. (2001) *Nature Rev.* 2:302; Giaever et al. (2004) *Proc. Natl. Acad. Sci. USA* 101:793; Eason et al. (2004) *Proc. Natl. Acad. Sci. USA* 101:11046; and Brenner (2004) *Genome Biol.* 5:240.

Contemplated Applications of the Phage Display Library

The described technology allows for detection of such past (e.g., resolved or unresolved infections) or ongoing infection by detecting host antibody response to a pathogen such as a virus, bacteria, or fungi. Using the described systems and methods, wherein a comprehensive peptide phage library can capture virtually all host generated antibodies, the simultaneous detection of the complete antiviral antibody responses as an indicator of virus infection against virtually all known viruses capable of infecting humans. Uniquely, because antibody responses persist for long periods of time, this approach further allows for detection of prior exposure, where an infection has been contained. These responses can therefore be used as an indicator not only a person person's past ongoing infections, but resolved ones as well.

In addition to the aforementioned diagnostic uses, this technology further provides a mechanism to identify viral correlates or causes of disease. Many diseases suspected have a viral cause, but without positive identification of a responsible pathogen. Examples include Kawasaki Disease, Bell's Palsy, Meniere's Disease, Type I Diabetes and Juvenile Idiopathic Arthritis. In each of these diseases and/or dysfunctional conditions, viral correlates of onset or severity have been suggested, but a pathogenic origin cannot be identified due to the lack of system-wide screening techniques for viral exposure, and researchers must rely on piecemeal detection schemes in order to narrow down possible disease-causing agents. In contrast, the described systems and methods provide not only a systematic approach to compare antiviral responses in patient and control sera to identify viral correlates of disease, but across virtually all viruses known to infect humans, allowing for a much improved route for identifying responsible pathogens.

In addition, the detection of antiviral antibody responses in subjects further allows identification of critical antigen peptide epitopes. The high-throughput nature of the described technology also allows rapid and wide-scale detection of such signatures across various subjects, thereby providing means for mapping of antiviral antibody epitopes across populations, which is not possible with existing technology. In addition to aiding antibody design for therapy, this information further allows identification of potential cross-reactivity with human antigens, a key source of autoimmune disease generation.

Importantly, a critical aspect of establishing programmable microarrays to include viral peptides is generation of an appropriate oligonucleotide sequence set for library generation. Importantly, wide-scale, parallel detection of viral antigens is particularly challenging, given their highly adaptive evolutionary nature and comparatively small antigenic signature compared to a library of human peptides, as one example. As unique library members may provide only short differences in antigenic sequence, the Inventors have improved algorithms for designing oligonucleotide sequences from parental protein sequences using randomized codons to minimize redundancy, and in order to increase the ability to align short reads to unique members of the library.

Importantly, the programmable microarray approach described herein, further including the antibody-focused adaptions, algorithms to design oligonucleotide sequences with reduced redundancy, and/or short read alignments, all lend themselves for wide extension of the programmable microarray technology to detection of other pathogens (e.g., bacteria or fungi), as well as adaption into other display systems (e.g., ribosome display, arrayed peptide, or yeast display). In this regard, the combination of advantages described herein provide a wide-ranging, systematic approach for using host antibody response as a means to identify past and present pathogen exposure.

The proteomic technology described herein applies a phage library that can uniformly express peptide libraries, such as synthetic representations of a complete set of viral peptides known to infect humans. Using this approach, the Inventors demonstrate viral peptides enriched by donor serum are highly reproducible and sera from different donors, on the other hand, recognize distinct profiles of peptides presumably commensurate with their previous unique histories of viral exposure. Moreover, using this approach, the Inventors identified a known epitope in the EBV BRRF2 protein that is cross-reactive with autoimmune antigens in patients with multiple sclerosis. The described systems and methods can therefore be applied to determine common antiviral antibody responses in people immunized against viruses in order to improve vaccine design.

All references cited herein are incorporated by reference in their entirety as though fully set forth. Unless defined otherwise, technical and scientific terms used herein have the same meaning as commonly understood by one of ordinary skill in the art to which this invention belongs.

Singleton et al., *Dictionary of Microbiology and Molecular Biology* 4th ed., J. Wiley & Sons (New York, N.Y. 2012); March, *Advanced Organic Chemistry Reactions, Mechanisms and Structure* 5th ed., J. Wiley & Sons (New York, N.Y. 2001); and Sambrook and Russel, *Molecular Cloning: A Laboratory Manual* 4th ed., Cold Spring Harbor Laboratory Press (Cold Spring Harbor, N.Y. 2012); provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The present invention may be as defined in any one of the following numbered paragraphs.

1. A method for detecting an antibody against a pathogen in a subject, the method comprising:
   (a) contacting a reaction sample comprising a display library with a biological sample comprising antibodies, wherein the display library comprises a plurality of peptides derived from a plurality of pathogens, and
   (b) detecting a peptide bound to at least one antibody, thereby detecting an antibody capable of binding the peptide.
2. The method of paragraph 1, wherein the plurality of pathogens is a plurality of viruses, bacteria or fungi.
3. The method of paragraph 1 or 2, wherein the display library is a phage display library.
4. The method of paragraph 1, 2, or 3, wherein the antibodies in the reaction sample are immobilized.
5. The method of any one of the preceding paragraphs, wherein the antibodies are immobilized to a solid support adapted for binding IgM, IgA, or IgG subclasses.
6. The method of any one of the preceding paragraphs, wherein the antibodies are immobilized by contacting the display library and antibodies from the biological sample with Protein A and/or Protein G.
7. The method of any one of the preceding paragraphs, wherein the Protein A and/or Protein G are immobilized to a solid support.
8. The method of any one of the preceding paragraphs, comprising removing unbound antibody and peptides of the display library.
9. The method of any one of the preceding paragraphs, wherein the plurality of peptides are each less than 100, 200, or 300 amino acids long.
10. The method of any one of the preceding paragraphs, wherein the plurality of peptides are each less than 75 amino acids long.
11. The method of any one of the preceding paragraphs, wherein each peptide of the plurality of peptides comprises a common adapter region appended to the end of the nucleic acid sequence encoding the peptide.
12. The method of any one of the preceding paragraphs, wherein the detection of the antibody comprises a step of lysing the phage and amplifying the DNA.
13. The method of any one of the preceding paragraphs, wherein at least two antibodies are detected.
14. The method of any one of the preceding paragraphs, wherein the at least two antibodies are detected simultaneously.
15. The method of any one of the preceding paragraphs, wherein antibodies from the biological samples are immobilized.
16. A method for identifying a pathogen associated with a disease, the method comprising
   (a) obtaining a biological sample from a plurality of subjects having a common disease, wherein the common disease is suspected of having a pathogenic component,
   (b) separately contacting each sample of a plurality of reaction samples with each biological sample under conditions that allow formation of at least one antibody-peptide complex, wherein the reaction samples each comprise a display library comprising a plurality of peptides derived from a plurality of pathogens,
   (c) isolating the at least one antibody-peptide complex formed in each reaction sample from unbound phage,
   (d) correlating at least one peptide in the at least one antibody-peptide complex in each reaction sample to the pathogen from which it is derived, and
   (e) identifying a pathogen that is significantly enriched in the plurality of subjects with disease compared to subjects without the disease.
17. The method of paragraph 16, wherein the plurality of pathogens is a plurality of viruses, bacteria or fungi.
18. The method of paragraph 16 or 17, wherein the display library is a phage display library.
19. The method of paragraph 16, 17, or 18, wherein the antibodies in the reaction sample are immobilized.
20. The method of any one of paragraphs 16-19, wherein the antibodies are immobilized to a solid support adapted for binding IgM, IgA, or IgG subclasses.
21. The method of any one of paragraphs 16-20, wherein the antibodies are immobilized by contacting the display library and antibodies from the biological sample with Protein A and/or Protein G.
22. The method of any one of paragraphs 16-21, wherein the Protein A and/or Protein G are immobilized to a solid support.
23. The method of any one of paragraphs 16-22, wherein the plurality of peptides are each less than 100 amino acids long.
24. The method of any one of paragraphs 16-23, wherein the plurality of peptides are each less than 75 amino acids long.
25. The method of any one of paragraphs 16-24, wherein each peptide of the plurality of peptides comprises a common adapter region appended to the end of the nucleic acid sequence encoding the peptide.
26. The method of any one of paragraphs 16-25, wherein the detection of the at least one peptide in the at least one antibody-peptide complex comprises a step of lysing the phage and amplifying the DNA.
27. The method of any one of paragraphs 16-26, wherein at least two peptides are detected.
28. The method of any one of paragraphs 16-27, wherein the at least two peptides are detected simultaneously.
29. The method of any one of paragraphs 16-28, wherein the common disease comprises disease selected from the group consisting of: Kawasaki Disease, Bell's Palsy, Meniere's Disease, Type I diabetes, juvenile idiopathic arthritis, Chronic Fatigue Syndrome, Gulf War Illness, Myasthenia Gravis, and IgG4 disease.
30. The method of any one of the preceding paragraphs, further comprising identifying the epitope to which the antibody binds.

31. The method of any one of the preceding paragraphs, further comprising determining whether the antibody cross-reacts with an autoimmune antigen in the subject.

32. A method for improving vaccine design, the method comprising:
(a) obtaining a biological sample from a plurality of subjects exposed to a pathogen,
(b) separately contacting each sample of a plurality of reaction samples with each biological sample under conditions that allow formation of at least one antibody-peptide complex, wherein the reaction samples each comprise a display library comprising a plurality of peptides derived from a plurality of pathogens,
(c) isolating the at least one antibody-peptide complex formed in each reaction sample from unbound phage,
(d) correlating at least one peptide in the at least one antibody-peptide complex in each reaction sample to the pathogen from which it is derived, and
(e) identifying an antigenic peptide that is significantly enriched in the plurality of subjects exposed to the pathogen as compared to subjects that have not been exposed to the pathogen for use in designing an improved vaccine.

33. The method of paragraph 32, wherein the plurality of pathogens is a plurality of viruses, bacteria or fungi.

34. The method of paragraph 32 or 33, wherein the display library is a phage display library.

35. The method of paragraph 32, 33 or 34, wherein the antibodies in the reaction sample are immobilized.

36. The method of any one of paragraphs 32-35, wherein the antibodies are immobilized to a solid support adapted for binding IgM, IgA, or IgG subclasses.

37. The method of any one of paragraphs 32-36, wherein the antibodies are immobilized by contacting the display library and antibodies from the biological sample with Protein A and/or Protein G.

38. The method of any one of paragraphs 32-37, wherein the Protein A and/or Protein G are immobilized to a solid support.

39. The method of any one of paragraphs 32-38, wherein the plurality of peptides are each less than 100, 200, or 300 amino acids long.

40. The method of any one of paragraphs 32-39, wherein the plurality of peptides are each less than 75 amino acids long.

41. The method of any one of paragraphs 32-40, wherein each peptide of the plurality of peptides comprises a common adapter region appended to the end of the nucleic acid sequence encoding the peptide.

42. The method of any one of paragraphs 32-41, wherein the detection of the antigenic peptide comprises a step of lysing the phage and amplifying the DNA.

43. The method of any one of paragraphs 32-42, wherein at least two peptides are detected.

44. The method of any one of paragraphs 32-43, wherein the at least two peptides are detected simultaneously.

45. A phage library displaying a plurality of viral peptides, wherein the plurality of viral peptides represent a set of peptides from viruses known to infect humans.

46. The phage library of paragraph 45, wherein the phage library comprises a plurality of viral peptides from at least 3 viruses known to infect humans.

47. The phage library of paragraph 45 or 46, wherein the phage library comprises a plurality of viral peptides from at least 10 viruses known to infect humans.

48. The phage library of paragraph 45, 46, or 47 wherein the phage library comprises a plurality of viral peptides from at least 20 viruses known to infect humans.

49. The phage library of any one of claims 45-48, wherein the phage library comprises at least 10 peptide sequences.

50. The phage library of any one of claims 45-49, wherein the phage library comprises at least 20 peptide sequences.

51. The phage library of any one of claims 45-50, wherein the plurality of peptides are each less than 100, 200 or 300 amino acids long.

52. The phage library of any one of claims 45-51, wherein the plurality of peptides are each less than 75 amino acids long.

53. The phage library of any one of claims 45-52, wherein each peptide of the plurality of peptides comprises a common adapter region appended to the end of the nucleic acid sequence encoding the peptide.

54. The phage library of any one of claims 45-53, wherein the plurality of peptides are immunodominant epitopes.

EXAMPLES

Example 1: Peptide Sequence Library Generation

Figure 1A:
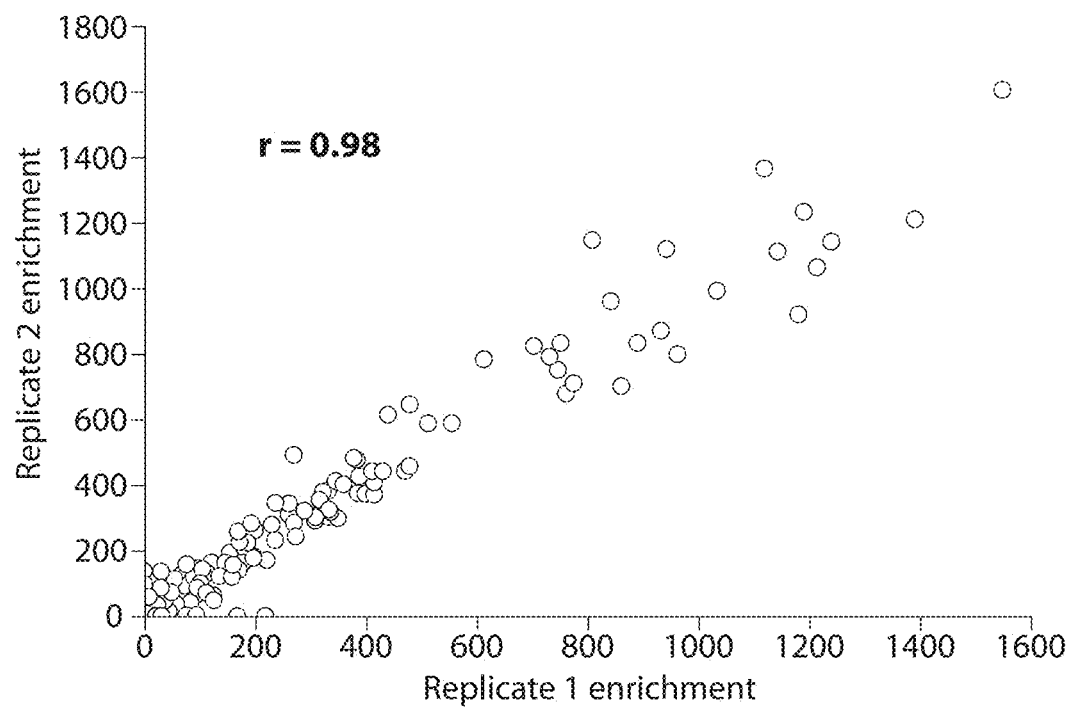
FIGS. 1A-1C show the fold enrichment of each peptide in each of two pull-downs with (FIG. 1A) the same donor serum or (FIG. 1B) the sera of two different donors (FIG. 1C) illustration of process (from Benjamin, et al. *Nature Biotechnology* 29: 535-541 (2011)).
Figure 1B:
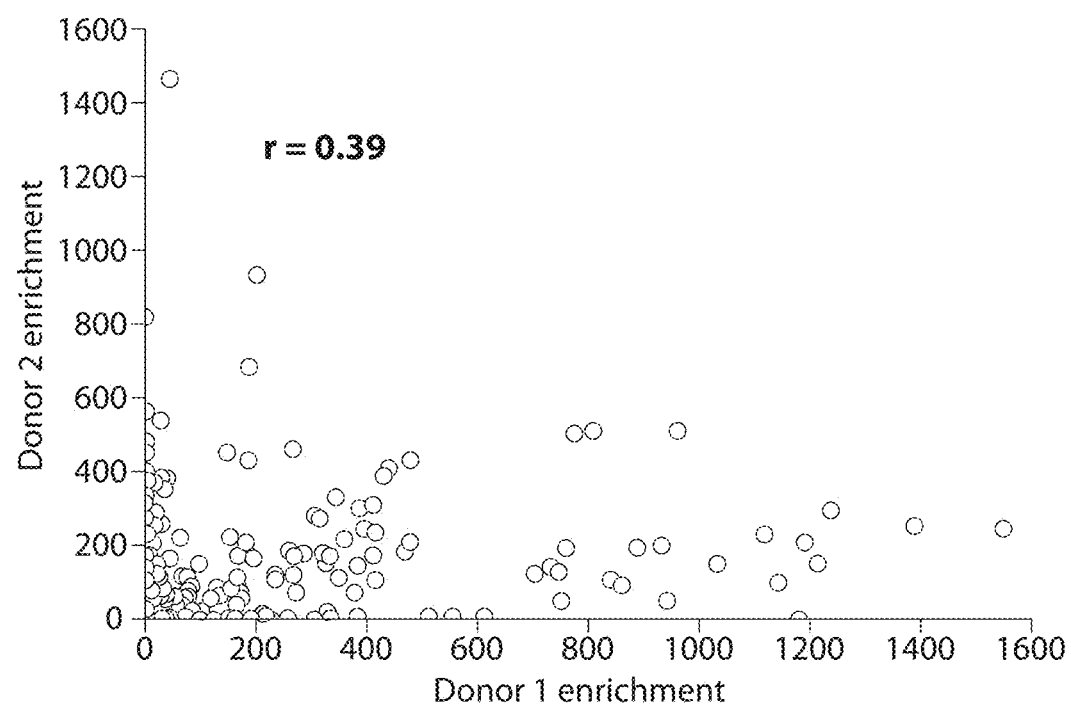
Figure 1C:
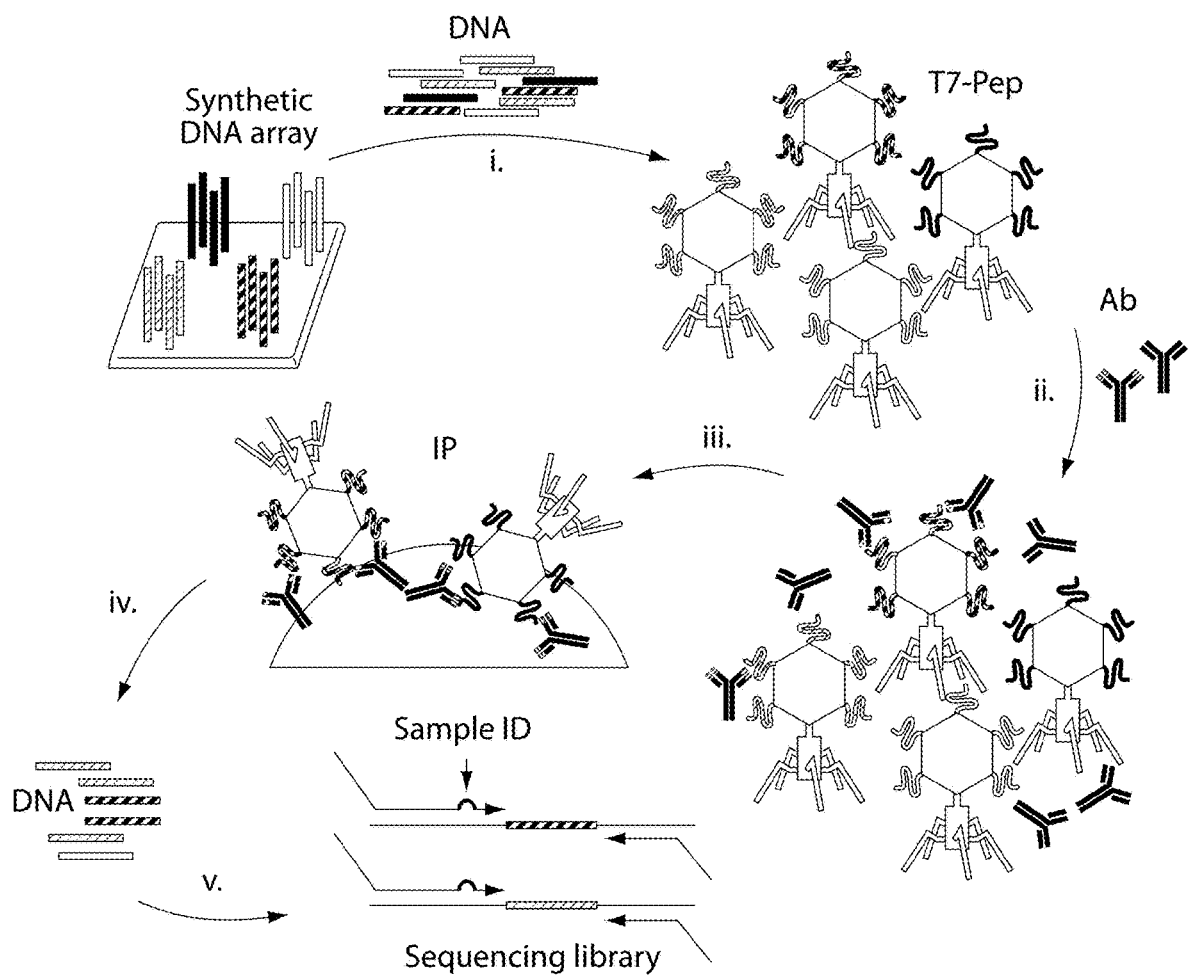

The general process is illustrated in FIG. 1C. Peptide sequences are back-translated into DNA sequences with randomized codon usage to minimize sequence redundancy in order to facilitate unique identification using short DNA reads. The DNA sequences were also edited using synonymous mutations to remove rare codons and restriction sites used for downstream cloning. Finally, a common "adapter" region was appended to the ends of each DNA sequence to allow PCR amplification of the library. The final set of defined DNA sequences were synthesized as oligonucleotides on a programmable DNA microarray, PCR amplified, and cloned into a commercially available T7-Select 10-3b display system using standard molecular biology techniques. The T7-Select 10-3b system produces peptides encoded by DNA as fusions to the exterior coat proteins of T7 bacteriophage particles. Each bacteriophage particle contains DNA encoding a peptide fused to the C-terminus of the T7 gene 10 protein. The exterior of the bacteriophage particle is surrounded by 415 copies of the gene 10 protein; on average, 5-15 of these copies will contain the C-terminal peptide fusion.

Example 2: Immobilization Steps

One can mix this set of modified bacteriophage with a sample containing antibodies. Any antiviral antibodies in the sample will bind to bacteriophage that display the cognate antigen. After a period of mixing, one adds in micron-sized magnetic beads coated with Protein A and Protein G. Protein A and G will bind to antibodies in the mixture and immobilize them on the beads. This process also immobilizes any phage particles bound by the antibodies. After another period of mixing, one can use a magnet to separate the immobilized phage from unbound phage.

Example 3: Phage Lysis and Signal Reading

Then, phage are lysed by heat denaturation and PCR is applied to amplify the DNA region corresponding to the displayed peptide sequence. This PCR primer contains a common adapter sequence which can be amplified in a second PCR reaction by another set of primers to prepare the DNA for Illumina high throughput sequencing. Unique barcoded oligonucleotides in the second PCR reaction amplify different samples and pool them together in one sequencing run for cost reduction.

To distinguish various signal reads, a set of custom Python scripts are applied to count the frequency of each peptide in each barcoded sample, and custom statistical analysis is applied to identify which peptides are significantly enriched by the selection. One can then determine which peptide epitopes are being recognized by antibodies in those samples.

Example 4: Detection of Viral Antibodies

As a preliminary test, the Inventors performed a pull-down using a commercial HA antibody, which recognizes an epitope of influenza haemagglutinin. Results are shown in FIGS. 1A and 1B. Importantly, using the described systems and methods, the Inventors were able to confirm 10 to 100-fold enrichment of at least two out of eight peptides in the library that contain the HA epitope. In a pilot study of donor antibody repertoires, the Inventors discovered that the viral peptides enriched by donor serum are highly reproducible. Sera from different donors, on the other hand, recognize distinct profiles of peptides presumably commensurate with their previous unique histories of viral exposure.

Figure 2:
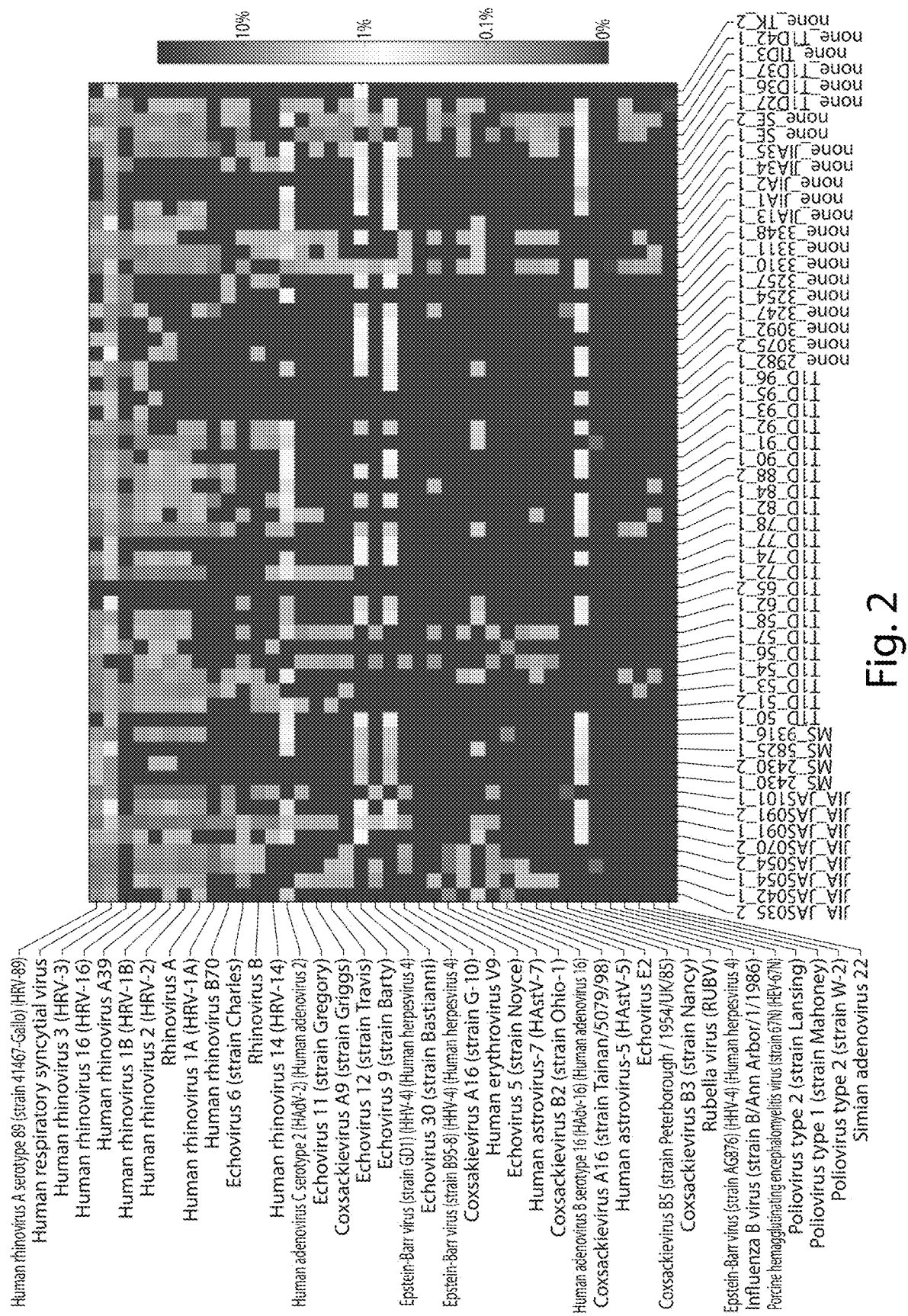
FIG. 2 is a heatmap showing the distribution of responses to viruses across different patient samples. The percentage of peptides from a particular virus that were determined to be significantly enriched in that particular sample.

A pattern of strong enrichment of peptide epitopes from a single virus indicates the sample donor is or was infected with that virus. In the described study, the Inventors observed that the vast majority of donors have strong responses against common viruses such as Rhinovirus (common cold), while fewer patients have strong responses against rarer viruses such as Human erythrovirus V9 or Simian adenovirus (FIG. 2).

Example 5: Detection of Cross-Reactive Antigens Related to Autoimmunity

Figure 3:
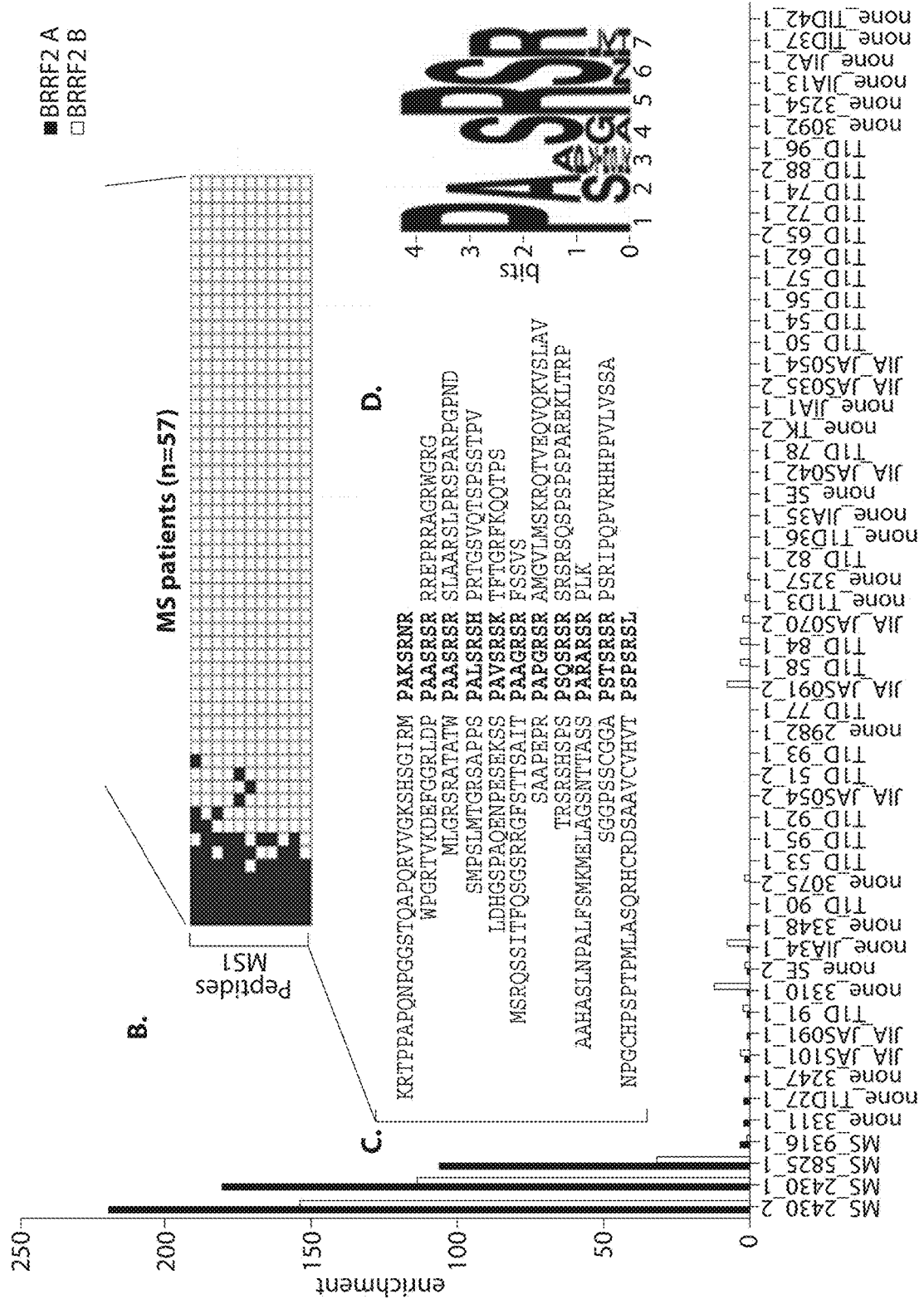
FIG. 3 Using a library of peptides encoded by the human genome, the Inventors identified an epitope in multiple sclerosis patients known to cross-react with a portion of the EBV BRRF2 protein (B) inset, black squares indicates the patient, columns, has a response against the peptide, row, containing the epitope). Using the library of peptides encoded by human viruses, the Inventors also detected strong responses against this epitope, found in two peptides (BRRF2 A and BRRF2 B), in all three of samples from patients with multiple sclerosis who had previously been confirmed to have cross-reacting antibody responses (MS_2430_2, MS2430_1, and MS_5826_1). (C) ClustalW alignment (SEQ ID NOs. 22-32, respectively, in order of appearance) is shown along with (D) MEME-generated seven-element motif.

As positive confirmation of the described systems and methods, the Inventors identified a known epitope in the EBV BRRF2 protein that is cross-reactive with autoimmune antigens in patients with multiple sclerosis (FIG. 3). This technology can be used to identify other such epitopes in diseases with suspected viral etiology. Particular peptide epitope responses can be important in providing protective immunity against reinfection. The described systems and methods can therefore be applied to determine common antiviral antibody responses in people immunized against viruses in order to improve vaccine design.

Example 6: VirScan

Summary

The human virome plays important roles in host health and immunity. However, current methods for detecting viral infections and antiviral responses have limited throughput and coverage. Described herein is the inventors' "VirScan", a high-throughput method to comprehensively analyze viral infection and antibody response using immunoprecipitation and massively parallel DNA sequencing of a bacteriophage library displaying peptides from all known human virus species. The inventors assayed over 106 million antibody-viral peptide interactions in 569 humans across four different continents, nearly doubling the number of previously established viral epitopes. In this cohort the inventors detected immune responses in sera to an average of 10 species of viruses per person and a total of 87 species in at least two individuals. It was determined that although rates of specific virus exposure are heterogeneous across populations, human antibody responses target strikingly conserved epitope cohorts for each virus, indicating that these broadly immunogenic epitopes elicit highly similar antibodies across individuals. The results described herein indicate that VirScan is a powerful approach for studying interactions between the virome and the immune system.

Background

Emerging evidence indicates that the collection of viruses found to infect humans (the "human virome") can have profound effects on human health (1). In addition to directly causing acute or chronic illness, each virus leaves an indelible footprint in the host. Viral infection permanently alters the immune system and can also alter host immunity in more subtle ways (2). For example, latent herpesvirus infection has been shown to confer symbiotic protection against bacterial infection in mice through prolonged production of interferon-γ and systemic activation of macrophages (3). This interplay between virome and host immunity has also been implicated in the pathogenesis of complex diseases such as type 1 diabetes, inflammatory bowel disease, and asthma (4). Despite this growing appreciation for the importance of interactions between the virome and host, a comprehensive method to systematically characterize these interactions has yet to be developed (5).

The advent of high-throughput DNA sequencing has ushered in a new era of unbiased viral nucleic acid detection (6). However, nucleic acid tests fail in cases where viruses have already been cleared after causing or initiating tissue damage and can miss viruses of low abundance or viruses not normally present in the sampled fluid or surface. In contrast, humoral responses to infection typically arise within two weeks of initial exposure and can persist over years or decades (7). Tests detecting antiviral antibodies in peripheral blood can therefore identify ongoing and cleared infections. However, current serological methods are predominantly limited to testing one virus at a time and are therefore only employed to address specific clinical hypotheses. Scaling serological analyses to encompass the complete human virome poses significant technical challenges, but would be of great value for better understanding host-virus interactions, and would overcome many of the limitations associated with current clinical technologies.

Described herein is VirScan, a novel technology that leverages recent advances in programmable DNA microarray technology to create a synthetic representation of the human virome (FIG. 1C). Immunoprecipitation and massively parallel DNA sequencing were used to comprehensively analyze the binding of an individual's antibodies to peptides in this synthetic human virome. VirScan is thus able to characterize the full spectrum of viral peptide epitopes targeted by an individual's B cell response. By testing a large number of individuals that are known to have viral infections detected by classical methods, it was confirmed that this platform identifies antiviral responses with very high sensitivity and specificity. Characterization of 569 serum samples revealed known and novel differences in viral exposure between populations of differing age, HIV status, and geographic location. Finally, the inventors employed VirScan to identify the specific B cell epitope determinants targeted and found remarkable similarity in epitope recognition across individuals and populations. These findings establish VirScan as a powerful new approach for studying interactions between the human virome and the immune system in health and disease.

Results

The VirScan Platform

VirScan utilizes the Phage Immunoprecipitation sequencing (PhIP-seq) technology as previously described (8). Briefly, the inventors used a programmable DNA microarray to synthesize 93,904 200-mer oligonucleotides, encoding 56-residue peptide tiles, with 28 residue overlaps, that together span the reference protein sequences (collapsed to 90% identity) of all viruses annotated to have human tropism in the UniProt database (9). This library includes peptides from 206 species of virus and over 1,000 different strains. The library was cloned into a T7 bacteriophage display vector for screening.

To perform a screen, one of skill in the art will incubate the library with a serum sample containing antibodies, recover the antibodies using a mixture of protein A and G coated magnetic beads, and remove unbound phage particles by washing. Finally, one will perform PCR and massively parallel DNA sequencing on the phage inserts to quantify enrichment of each library member due to antibody binding. Each sample is screened in duplicate to ensure reproducibility. VirScan requires only 2 µg of immunoglobulin (<1 µL of serum) per sample and can be automated on a 96-well liquid handling robot (10). PCR product from 96 immunoprecipitations can be individually barcoded and pooled for sequencing, reducing the cost for a comprehensive viral Ab screen to approximately $25 per sample.

Figure 8:
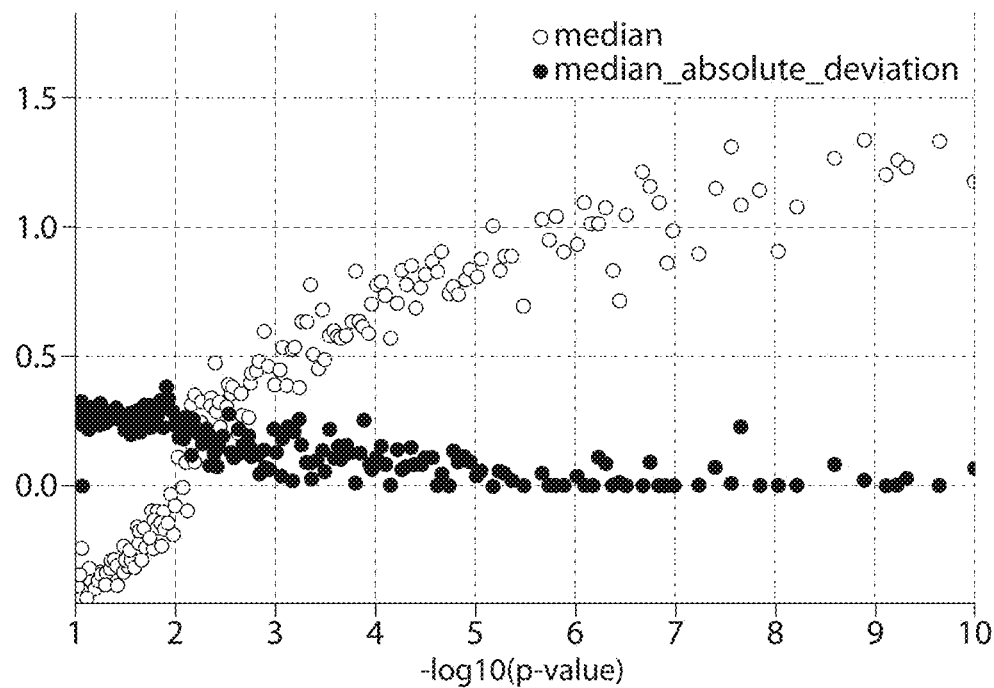
FIG. 8 Reproducibility threshold. Scatterplot for median and median absolute deviation of replicate 2–$\log_{10}$(p-values) whose replicate 1–$\log_{10}$(p-value) falls within the window whose left edge is shown on the horizontal axis.
Figure 9:
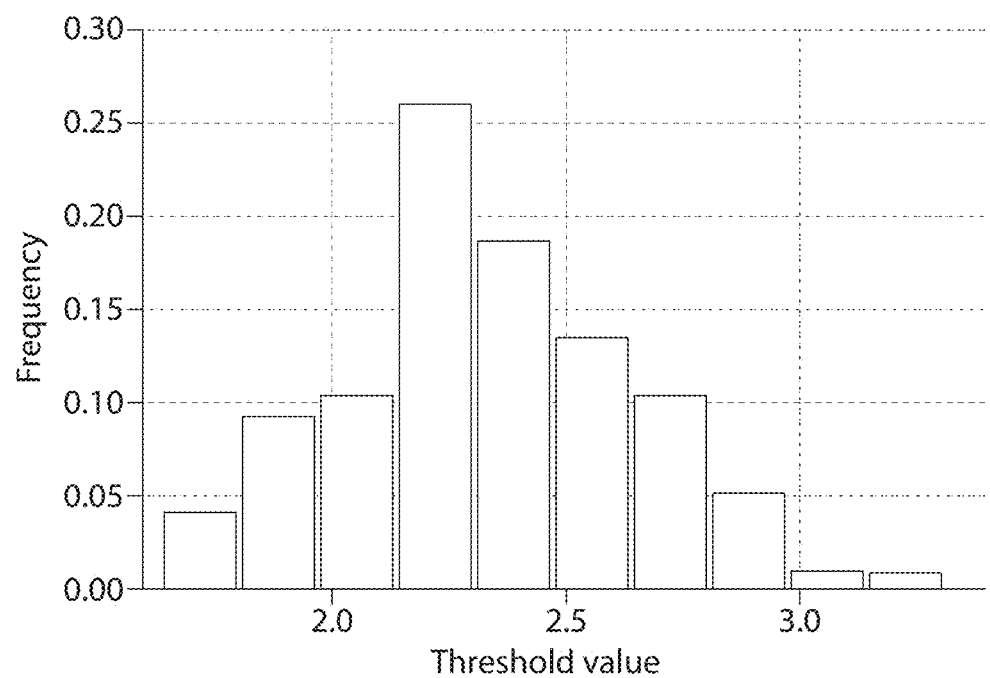
FIG. 9 Distribution of reproducibility threshold $-\log_{10}$(p-values). Histogram of the frequency of the reproducibility threshold $-\log_{10}$(p-values). The mean and median of the distribution are both approximately 2.3.

Following sequencing, the inventors tally the read count for each peptide before ("input") and after ("output") immunoprecipitation. The inventors then fit a zero-inflated generalized Poisson model to the distribution of output read counts for each input read count and regress the parameters as a function of input read count (FIG. 8). Using this model, a $-\log_{10}$(p-value) for the significance of each peptide's enrichment is calculated. Finally, a peptide is determined to be "significantly enriched" if its $-\log_{10}$(p-value) is greater than the reproducibility threshold of 2.3 in both replicates (FIG. 9).

VirScan is Highly Sensitive and Specific

Figure 4A:
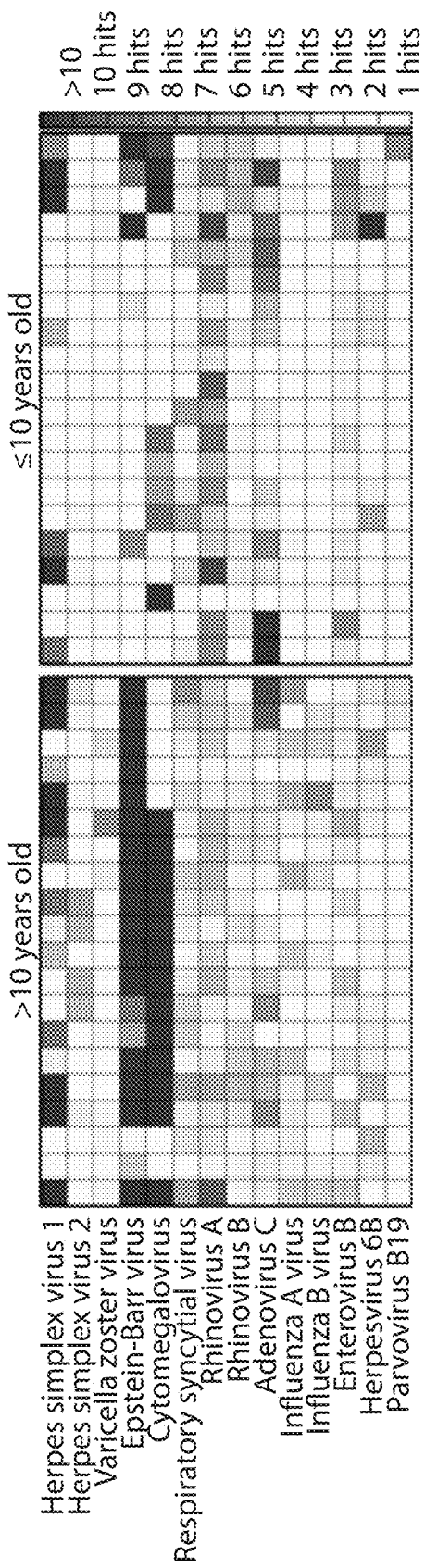
FIGS. 4A-4E show a general VirScan analysis of the human virome. The virome peptide library consists of 93,904 56 amino acid peptides tiling, with 28 amino acid overlap, across the proteomes of all known human viruses. 200 nt DNA sequences encoding the peptides were printed on a releasable DNA microarray. The released DNA was amplified and cloned into a T7 phage display vector and packaged into virus particles displaying the encoded peptide on its surface. The library is mixed with a sample containing antibodies that bind to their cognate peptide antigen on the phage surface. The antibodies are immobilized and unbound phage are washed away. Finally, amplification of the bound DNA and high throughput sequencing of the insert DNA from bound phage reveals peptides targeted by sample antibodies. Abbreviations: aa, amino acid; Ab, antibody; IP: immunoprecipitation.

FIG. 4a shows the antibody profiles of a set of human viruses in sera from a typical group of individuals in a heat map format that illustrates the number of enriched peptides from each virus. The inventors frequently detected antibodies to multiple peptides from common human viruses, such as Epstein-Barr virus (EBV), Cytomegalovirus (CMV), and rhinovirus. As expected, more peptides were observed to be enriched from viruses with larger proteomes, such as EBV and CMV, likely because there are more epitopes available for recognition. The inventors noticed fewer enriched peptides in samples from individuals less than ten years of age compared to their geographically matched controls, in line with an accumulation of viral infections throughout adolescence and adulthood. However, there were occasional samples from young donors with very strong responses to viruses that cause childhood illness, such as Parvovirus B19 and Herpesvirus 6B, which cause the "fifth disease" and "sixth disease" of the classical infectious childhood rashes, respectively (11). These observations are examined in greater detail in FIG. 5.

A computational method was developed to identify the set of viruses to which an individual has been exposed, based on the number of enriched peptides identified per virus. Briefly, the inventors set a threshold number of significant non-overlapping peptide enrichments for each virus. The inventors empirically determined that a threshold of three non-overlapping enriched peptides gave the best performance for detecting Herpes simplex virus 1 compared to a commercial serologic test, described below (Table 1).

TABLE 1

Virscan is highly sensitive and specific. Sensitivity is the percentage of samples positive for the virus as determined by VirScan out of all n known positives. Specificity is the percentage of samples negative for the virus by VirScan out of all n known negatives.

| Virus | Sensitivity (n) | Specificity (n) |
| --- | --- | --- |
| Hepatitis C virus | 93% (26) | 97%* (31) |
| Human immunodeficiency virus 1 | 93% (61) | 97%** (31) |
| Herpes simplex virus 1 | 97% (38) | 100% (6) |
| Herpes simplex virus 2 | 90% (20) | 100% (24) |

*The one false negative was from an individual whose HCV-negative status was self-reported, but had antibodies to as many HCV peptides as 23% of the true HCV positive individuals and is likely to be HCV positive now or in the past. It is possible that this individuals was exposed to HCV but cleared the infection. If true, the observed specificity for HCV is 100%.
**The one false positive was from an individual whose HIV-negative status was self-reported, but had antibodies to as many HIV peptides as 68% of the true HIV positive individuals and was very likely to be HIV positive. If true, the observed specificity for HIV is 100%.

Figure 10:
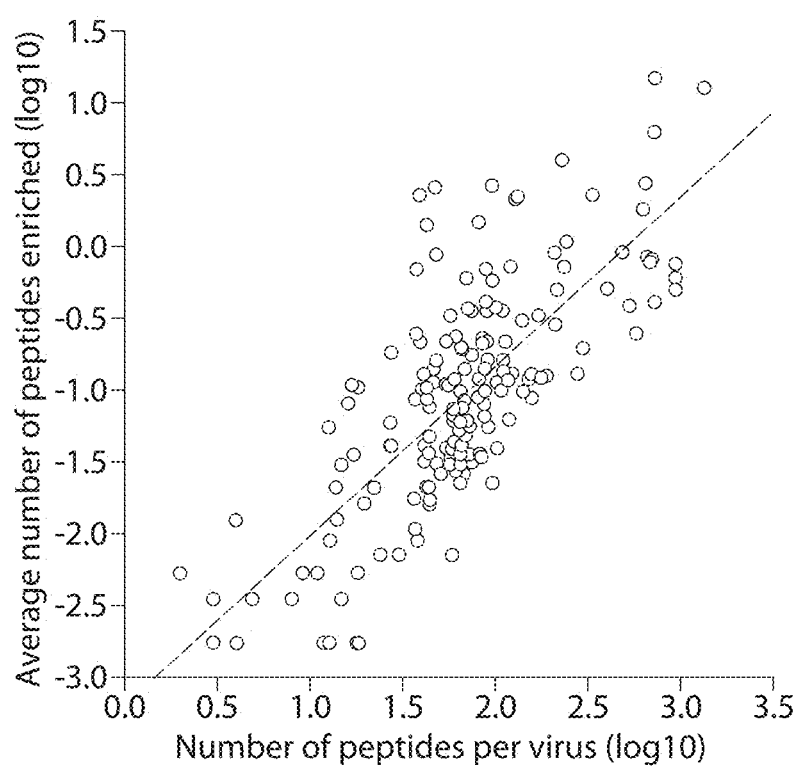
FIG. 10 Correlation between virus size and number of enriched peptides. Each dot on this log-log scatterplot is a virus. The horizontal axis corresponds to the size of the virus in number of peptides. The vertical axis corresponds to the average number of peptides enriched from the virus across all samples tested. The dashed line is a least-squares best-fit curve for the data.

For other viruses, the inventors adjusted the threshold to account for the size of the viral proteome (FIG. 10). Next, the number of enriched peptides from each virus was tallied. Antibodies generated against a specific virus can cross-react with similar peptides from a related virus. This would lead to false positives because an antibody targeted to an epitope from one virus to which a donor was exposed would also enrich a homologous peptide from a related virus to which the donor may not have been exposed. In order to address this issue, the inventors adopted a maximum parsimony approach to infer the fewest number of virus exposures that could elicit the observed spectrum of antiviral peptide antibodies. For groups of enriched peptides that share a 7 amino acid subsequence and may be recognized by a single specific antibody, the inventors only count it as one epitope for the virus which has the greatest number of other enriched peptides. If this adjusted peptide count is greater than the threshold for that virus, the sample is considered positive for the virus.

Using this analytical framework, the inventors measured the performance of VirScan using serum samples from patients known to be infected or not infected with human immunodeficiency virus (HIV) and Hepatitis C virus (HCV), based on commercial Elisa and WB assays. For both viruses, VirScan achieves very high sensitivities and specificities of ~95% or higher (Table 1). The viral genotype was also known for the HCV samples. Despite the very high sequence similarity among HCV genotypes (12), which poses a problem for all antibody-based detection methods, VirScan correctly reported the HCV genotype in 72% of the samples. The inventors also compared VirScan to a commercially available serology test that is type specific for the highly related Herpes simplex viruses 1 and 2 (HSV1 and HSV2). Again, despite sequence similarity between these viruses, VirScan is extremely specific and sensitive (Table 1). These results demonstrate that VirScan performs well in distinguishing between closely related viruses. The data also demonstrate that VirScan can detect antibodies to viruses that range in size from small (HIV and HCV) to very large (HSV1 and HSV2) with high sensitivity and specificity.

Population-Level Analysis of Viral Exposures

Figure 4B:
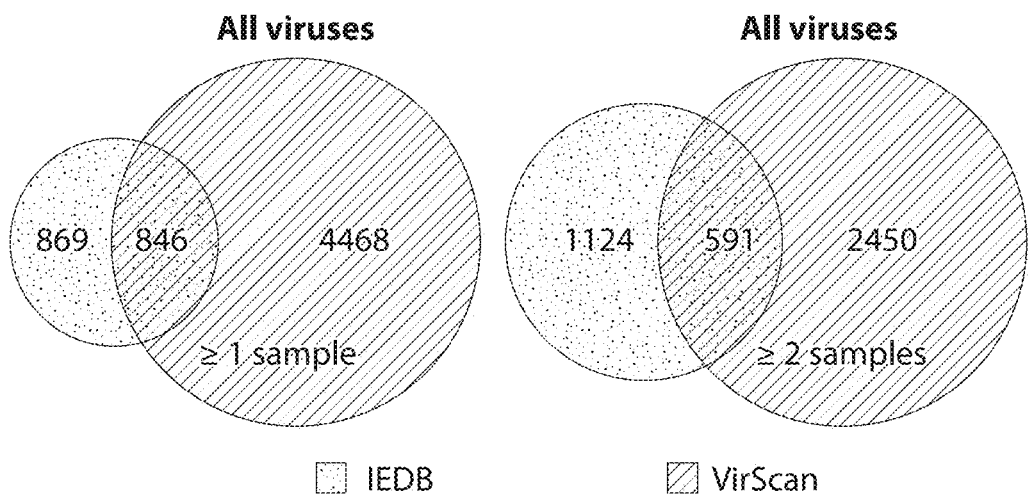
Figure 4C:
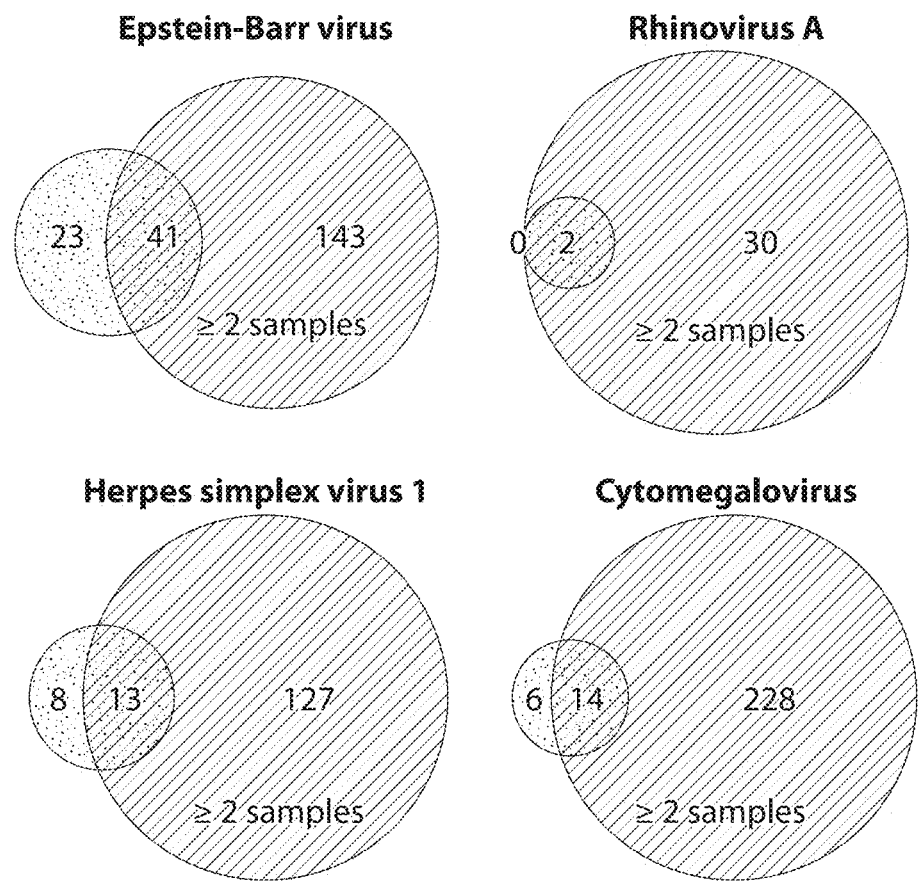
Figures 4D, 4E:
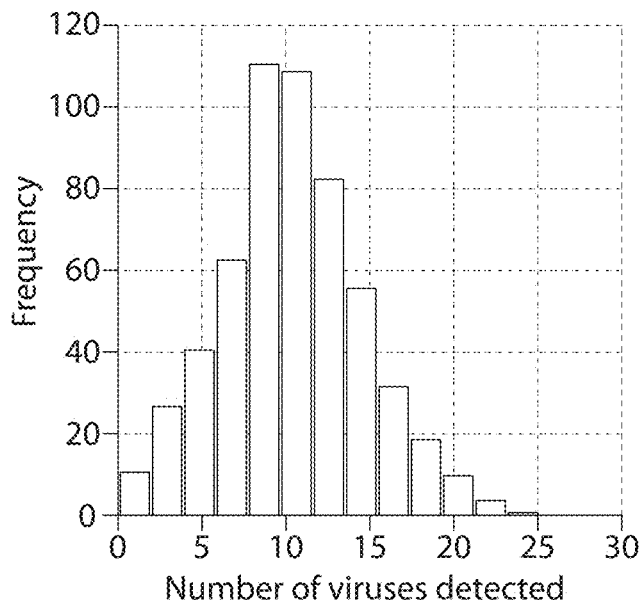

After ascertaining the high accuracy of VirScan for a panel of viruses, the inventors undertook a large-scale screening of samples that lacked any annotation of exposure history. Using our multiplex approach, 106 million antibody-peptide interactions were assayed using samples from 569 human donors in duplicate. Antibody responses were detected to an average of 10 species of virus per sample (FIG. 4D). Each person is likely exposed to multiple distinct strains of some viral species. These results are the first such estimate. Antibody responses to 65 of the 206 species of virus in the library were detected in at least 5 individuals, and 87 species in at least 2 individuals (Table 2).

TABLE 2

Prevalence of all viruses detected in donors residing in the United States. Known HIV-positive and HCV-positive samples were excluded from this analysis.

| Virus | % |
| --- | --- |
| Epstein-Barr virus | 88.1 |
| Rhinovirus B | 75.2 |
| Human adenovirus C | 74.6 |
| Rhinovirus A | 73.9 |
| Human respiratory syncytial virus | 68.0 |
| Influenza A virus | 58.4 |
| Human herpesvirus 6B | 57.1 |
| Herpes simplex virus 1 | 54.1 |
| Cytomegalovirus | 49.8 |
| Influenza B virus | 42.2 |
| Enterovirus C | 37.3 |
| Varicella zoster virus | 24.4 |
| Human adenovirus F | 22.1 |
| Human adenovirus B | 17.5 |
| Herpes simplex virus 2 | 16.5 |
| Enterovirus A | 16.5 |
| Enterovirus B | 11.9 |
| Norwalk virus | 11.6 |
| Mamastrovirus 1 | 11.2 |
| Human herpesvirus 7 | 10.2 |
| Human parainfluenza virus 3 | 9.6 |
| Human adenovirus D | 8.6 |
| Cowpox virus | 7.6 |
| Human adenovirus A | 6.9 |
| Human metapneumovirus | 6.3 |
| Human coronavirus HKU1 | 5.6 |
| Influenza C virus | 4.6 |
| Hepatitis B virus | 4.6 |
| Human parvovirus B19 | 4.3 |
| Human herpesvirus 6A | 4.0 |
| Aichivirus A | 4.0 |
| Virus | % |
| Alphapapillomavirus 9 | 3.6 |
| Rubella virus | 3.3 |
| Hepatitis E virus | 2.6 |
| Human herpesvirus 8 | 2.3 |
| Betapapillomavirus 1 | 2.3 |
| Rotavirus A | 2.0 |
| Human parainfluenza virus 4 | 2.0 |
| Torque teno virus | 1.7 |
| Measles virus | 1.7 |
| Human coronavirus NL63 | 1.7 |
| Hepatitis C virus | 1.7 |
| Eastern equine encephalitis virus | 1.7 |
| Tanapox virus | 1.3 |
| Rotavirus C | 1.3 |
| Betapapillomavirus 2 | 1.3 |
| Alphapapillomavirus 7 | 1.3 |
| Alphapapillomavirus 11 | 1.3 |
| Alphapapillomavirus 10 | 1.3 |
| Venezuelan equine encephalitis virus | 1.0 |
| SARS-related coronavirus | 1.0 |
| Ross River virus | 1.0 |
| Human parainfluenza virus 1 | 1.0 |
| Human adenovirus E | 1.0 |
| Betacoronavirus 1 | 1.0 |
| Yaba monkey tumor virus | 0.7 |
| Variola virus | 0.7 |
| Torque teno mini virus 1 | 0.7 |
| Rotavirus B | 0.7 |
| Lagos bat virus | 0.7 |
| Human coronavirus 229E | 0.7 |
| Hepatitis A virus | 0.7 |

TABLE 2-continued

Prevalence of all viruses detected in donors residing in the United States. Known HIV-positive and HCV-positive samples were excluded from this analysis.

| Virus | % |
| --- | --- |
| Dugbe virus | 0.7 |
| Dengue virus | 0.7 |
| Chikungunya virus | 0.7 |
| Bat coronavirus 1B | 0.7 |
| Alphapapillomavirus 1 | 0.7 |
| Yellow fever virus | 0.3 |
| Vesicular stomatitis Indiana virus | 0.3 |
| Vaccinia virus | 0.3 |
| Uukuniemi virus | 0.3 |
| Torque teno midi virus 1 | 0.3 |
| Orf virus | 0.3 |
| Monkeypox virus | 0.3 |
| Molluscum contagiosum virus | 0.3 |
| Marburg marburgvirus | 0.3 |
| Macacine herpesvirus 1 | 0.3 |
| KI polyomavirus | 0.3 |
| JC polyomavirus | 0.3 |
| Isfahan virus | 0.3 |
| Human parainfluenza virus 2 | 0.3 |
| Human immunodeficiency virus 2 | 0.3 |
| Getah virus | 0.3 |
| Enterovirus D | 0.3 |
| Cercopithecine herpesvirus 2 | 0.3 |
| Bunyamwera virus | 0.3 |
| Banna virus | 0.3 |
| Australian bat lyssavirus | 0.3 |
| Alphapapillomavirus 3 | 0.3 |
| Alphapapillomavirus 2 | 0.3 |
| Alphacoronavirus 1 | 0.3 |

The most frequently detected viruses are generally those known to commonly infect humans (FIG. 4E). The inventors occasionally detected what appear to be false positives that may be due to antibodies that cross react with non-viral peptides. For example, over 43% of the samples positive for Cowpox virus were right at the threshold of detection and had antibodies against a peptide from the C4L gene that shares an eight amino acid sequence ('SESDSDSD') (SEQ ID NO: 1) with the Clumping Factor B protein from *Staphylococcus aureus*, which humans are known to generate antibodies against (13). This will become less of an issue as the inventors test more examples of sera from patients with known infections to determine the set of likely immunogenic peptides for a given virus. The inventors frequently detected antibodies to rhinovirus and respiratory syncytial virus, which are normally found only in the respiratory tract, indicating that VirScan using blood samples is still able to detect viruses that do not cause viremia. Antibodies to influenza, which is normally cleared, and poliovirus were also detected, which in modern times most people generate antibodies through vaccination. Since the original antigen is no longer present, the inventors are likely detecting antibodies secreted by long-lived memory B cells (14).

The frequency at which influenza (58.4%) and poliovirus (37.3%) was detected is lower than expected given that the majority of the population has been exposed to or vaccinated against these viruses. This may be due to reduced sensitivity because of a gradual narrowing and decrease of the long-lived B cell response in the absence of persistent antigen. The frequency of detecting varicella zoster virus (chicken pox) antibodies is also lower than expected (24.4%), even though the frequency of detecting other latent herpesviruses, such as Epstein-Barr virus (88.1%) and cytomegalovirus (49.8%), is similar to the prevalence reported in epidemiological studies (15-17). Without wishing to be bound by theory, this may reflect differences in how frequently these viruses shed antigens that stimulate B cell responses or a more limited humoral response that relies on epitopes that cannot be detected in a 56 residue peptide. It might be possible to increase the sensitivity of detection of these viral antibodies by stimulating memory B cells in vitro to probe the history of infection more deeply.

Figure 5A:
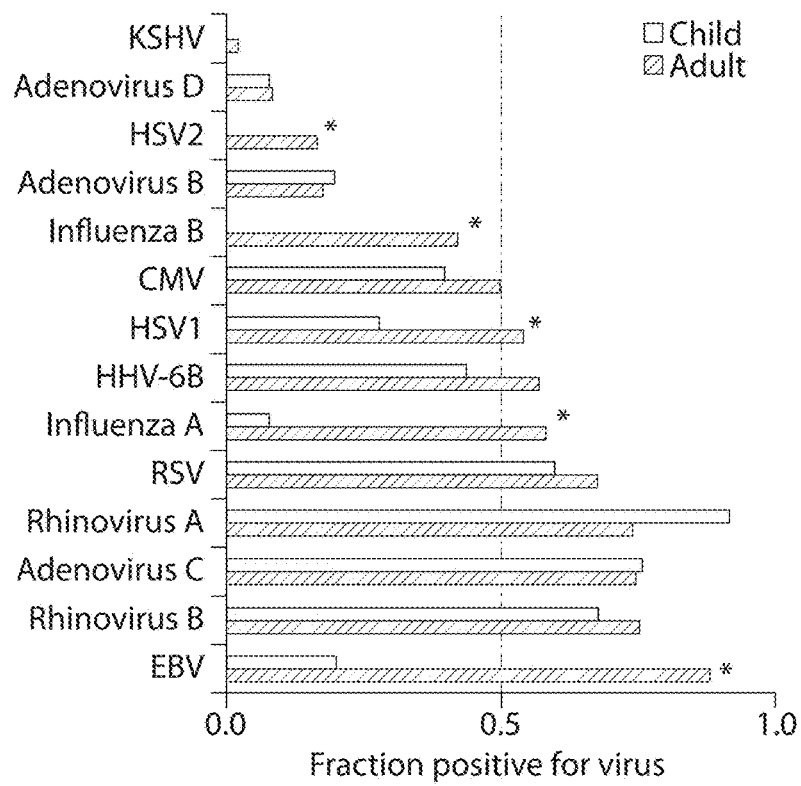
FIGS. 5A-5E show a population stratification of the human virome immune response. The bar graphs depict the differences in exposure to viruses between donors who are (FIG. 5A) children less than ten years of age versus adults over ten years of age, (FIG. 5B) HIV positive versus HIV negative, (FIG. 5C) residing in Peru versus residing in the United States, (FIG. 5D) residing in South Africa versus residing in the United States, and (FIG. 5E) residing in Thailand versus residing in the United States. Asterisks indicate false discovery rate <0.05.

To assess differences in viral exposure between populations, the inventors split the samples into different groups based on age, HIV status, and geography. Results were first compared from children under the age of ten to adults within the United States (HIV-positive individuals were excluded from this analysis) (FIG. 5A). Fewer children were positive for most viruses, including Epstein-Barr virus, HSV1, HSV2, and influenza virus, which is consistent with our preliminary observations comparing the number of enriched peptides (FIG. 4A). Even though children may generate lower antibody titers in general, the data are in line with these younger donors probably have not yet been exposed to many of these viruses, for example HSV2 which is sexually transmitted (18).

Figure 5B:
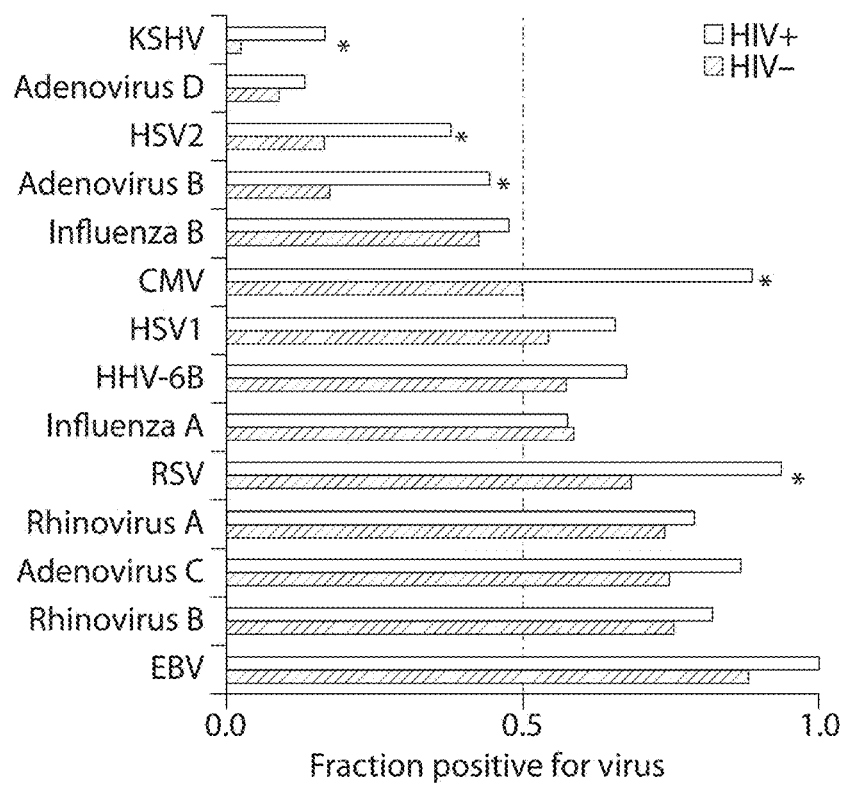

When comparing results from HIV positive to HIV negative samples, the inventors found more of the HIV positive samples to also be seropositive for additional viruses, including HSV2, CMV, and Kaposi's sarcoma-associated herpesvirus (KSHV) (false discovery rate q<0.05, FIG. 5B). These results are consistent with prior studies indicating higher risk of these co-infections in HIV positive patients (19-21). Without wishing to be bound by theory, the patients with HIV may engage in activities that put them at higher risk for exposure to these viruses. Alternatively, these viruses may increase the risk of HIV infection.

Figure 5C:
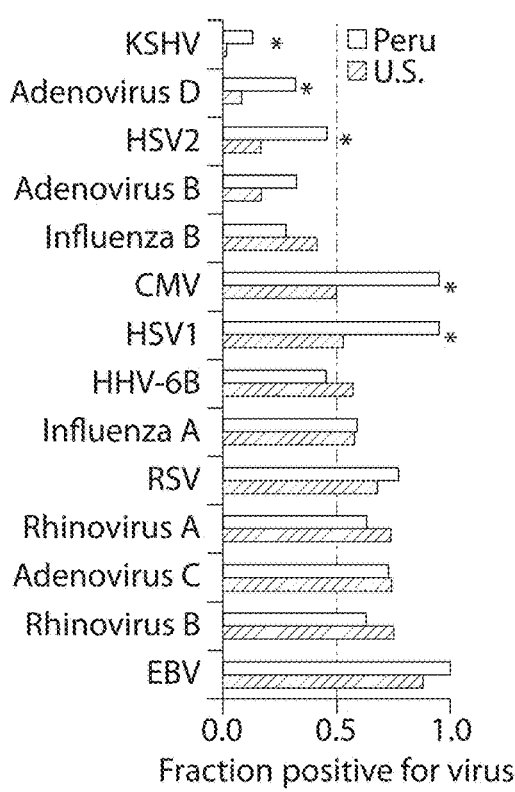
Figure 5D:
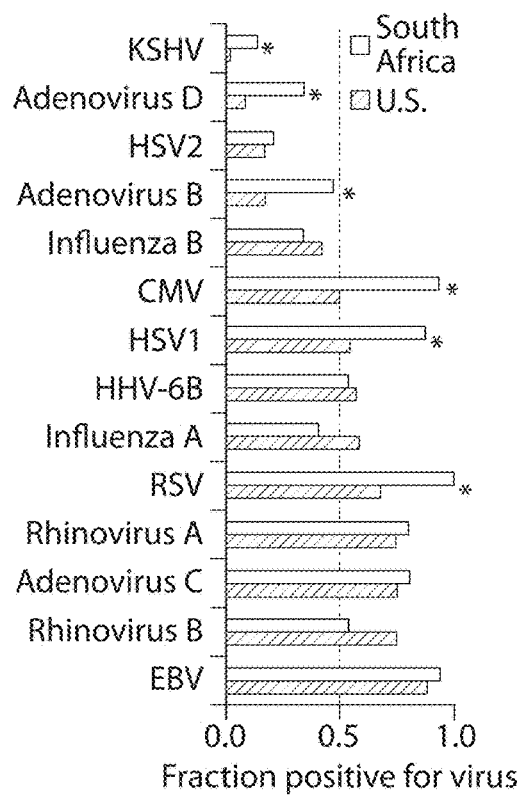
Figure 5E:
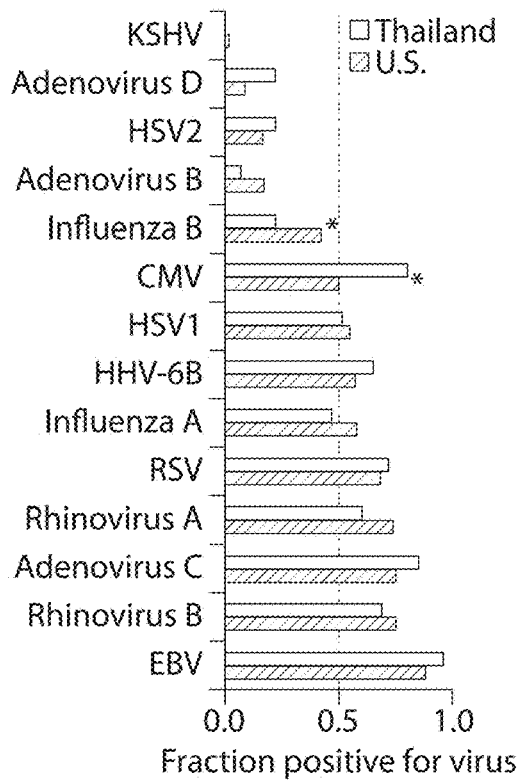

Finally, the inventors compared the evidence of viral exposure between samples taken from adult HIV-negative donors residing in countries from four different continents (the United States, Peru, Thailand, and South Africa). In general, donors outside the United States had higher frequencies of seropositivity (FIGS. 5C-5E). For example, cytomegalovirus antibodies were found in significantly higher frequencies in samples from Peru, Thailand, and South Africa. Other viruses, such as Kaposi's sarcoma-associated herpesvirus and HSV1 were detected more frequently in donors from Peru and South Africa, but not Thailand. The observed seroprevalence of different adenovirus species varies across populations. Adenovirus C seropositivity was found at similar frequencies in all regions, but Adenovirus D seropositivity was generally higher outside the United States, while Adenovirus B seropositivity was higher in Peru and South Africa, but lower in Thailand. Without wishing to be bound by theory, the higher rates of virus exposure outside the United States could be due to differences in population density, cultural practices, sanitation, or genetic susceptibility. Interestingly, Influenza B seropositivity was more common in the United States compared to other countries, especially Thailand. The incidence of Influenza B is much lower than Influenza A but the standard flu vaccination contains both Influenza A and B strains, so the elevated frequency of individuals with seroreactivity may be due to higher rates of flu vaccination in the United States. Other viruses, such as Rhinovirus and Epstein-Barr virus, were detected at very similar frequencies in all the geographic regions.

Analysis of Viral Epitope Determinants

Figure 11A:
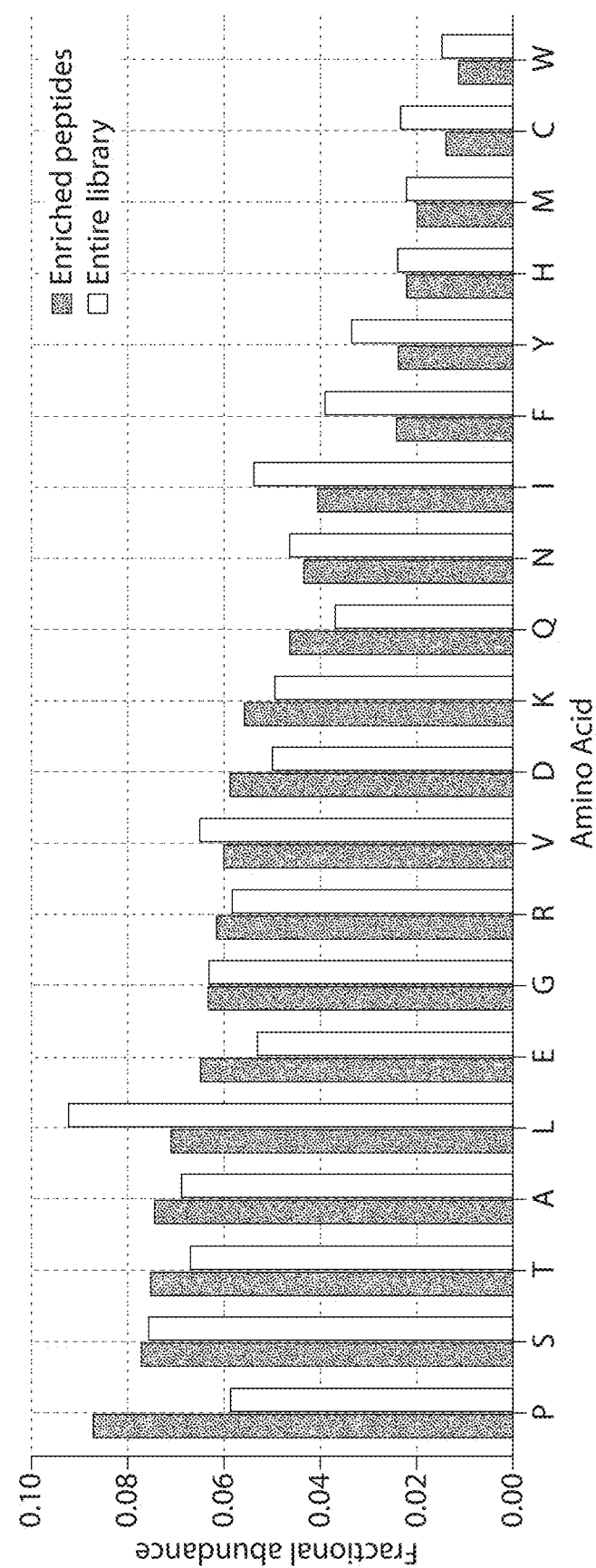
FIGS. 11A-11B Amino acid composition of enriched peptides.
Figure 11B:
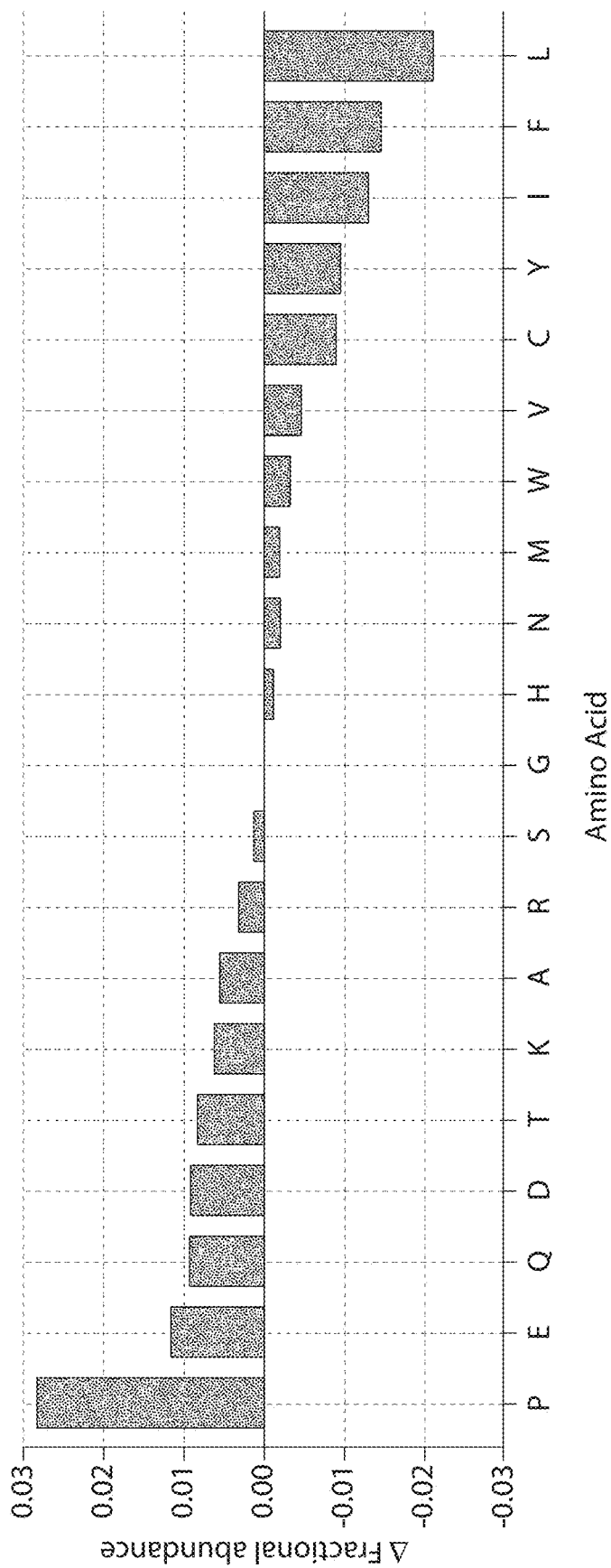
Figure 12A:
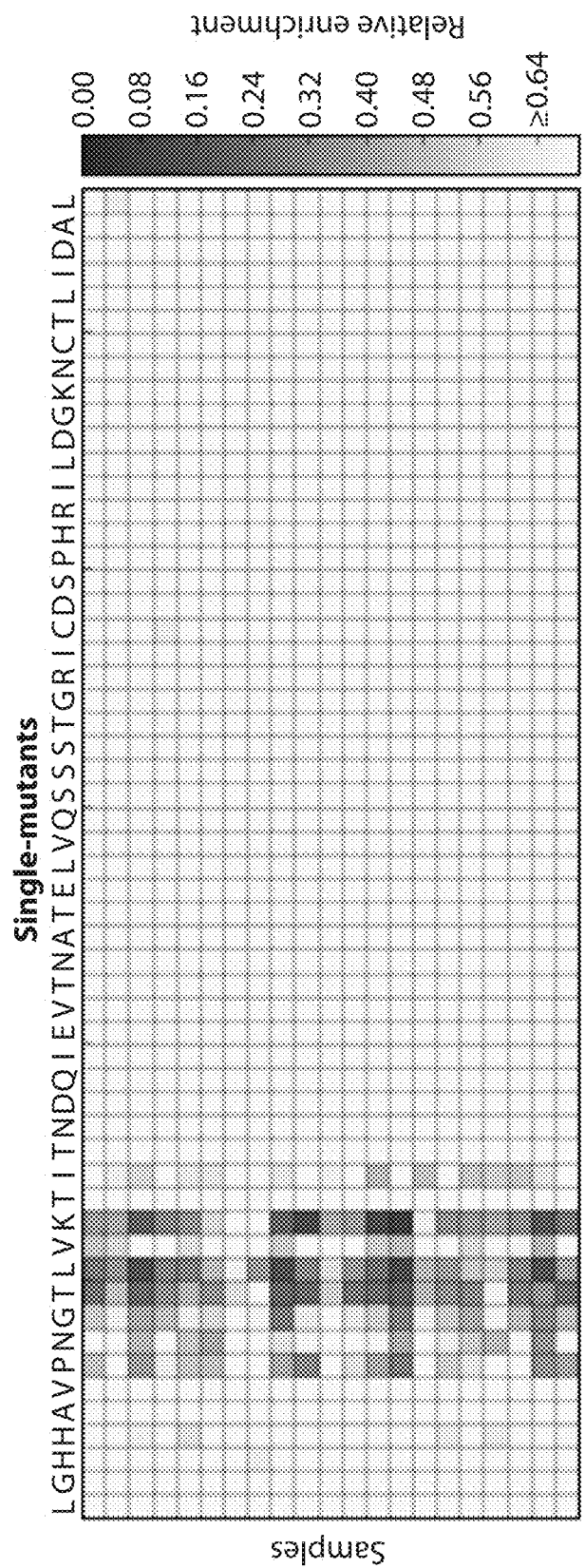
FIGS. 12A-12C Influenza A: hemagglutinin (UniProt ID: H8PET1, positions 1-56) Scanning mutagenesis identification of linear B cell epitopes in an immunogenic peptide from human viral proteins. Each row is a sample. Each column denotes the first mutated position for (FIG. 12A) single- (SEQ ID NO.
Figure 12B:
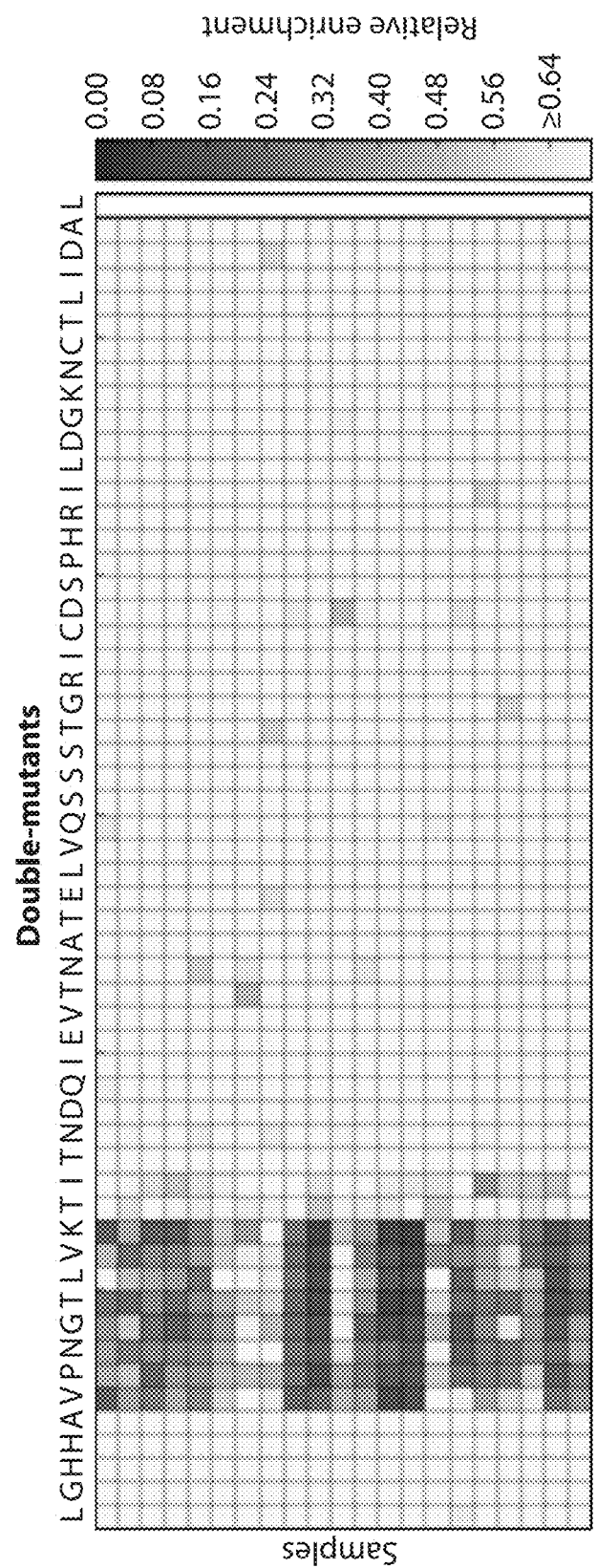
Figure 12C:
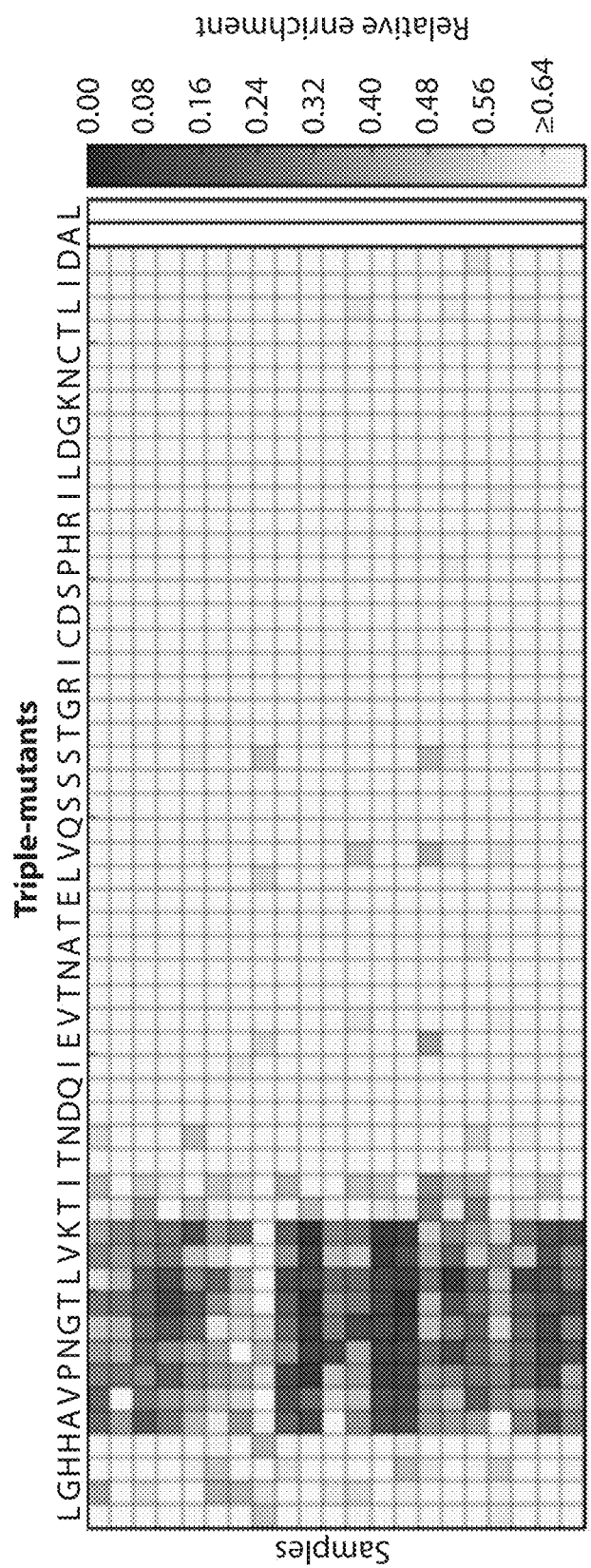
Figure 13A:
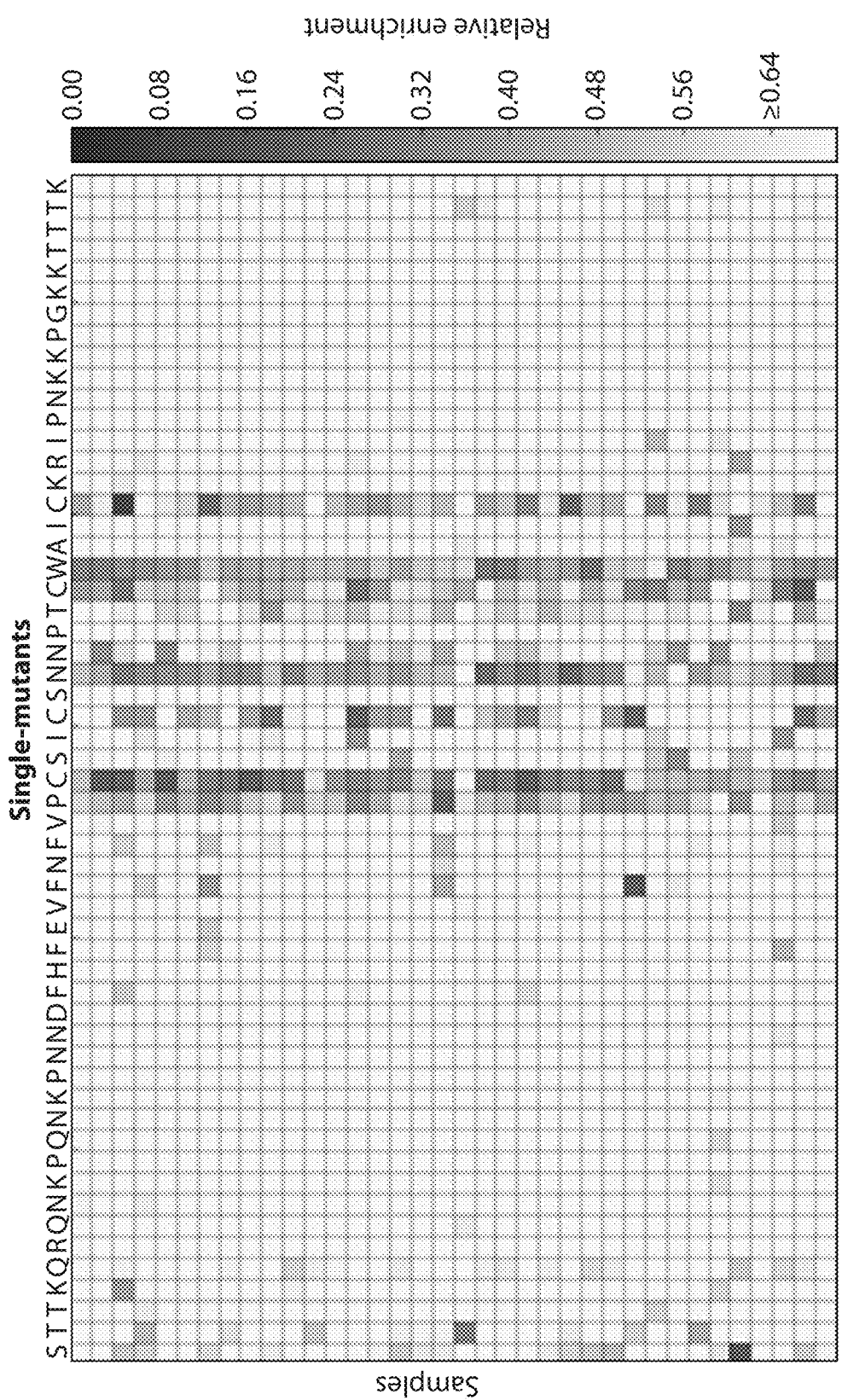
Figure 13B:
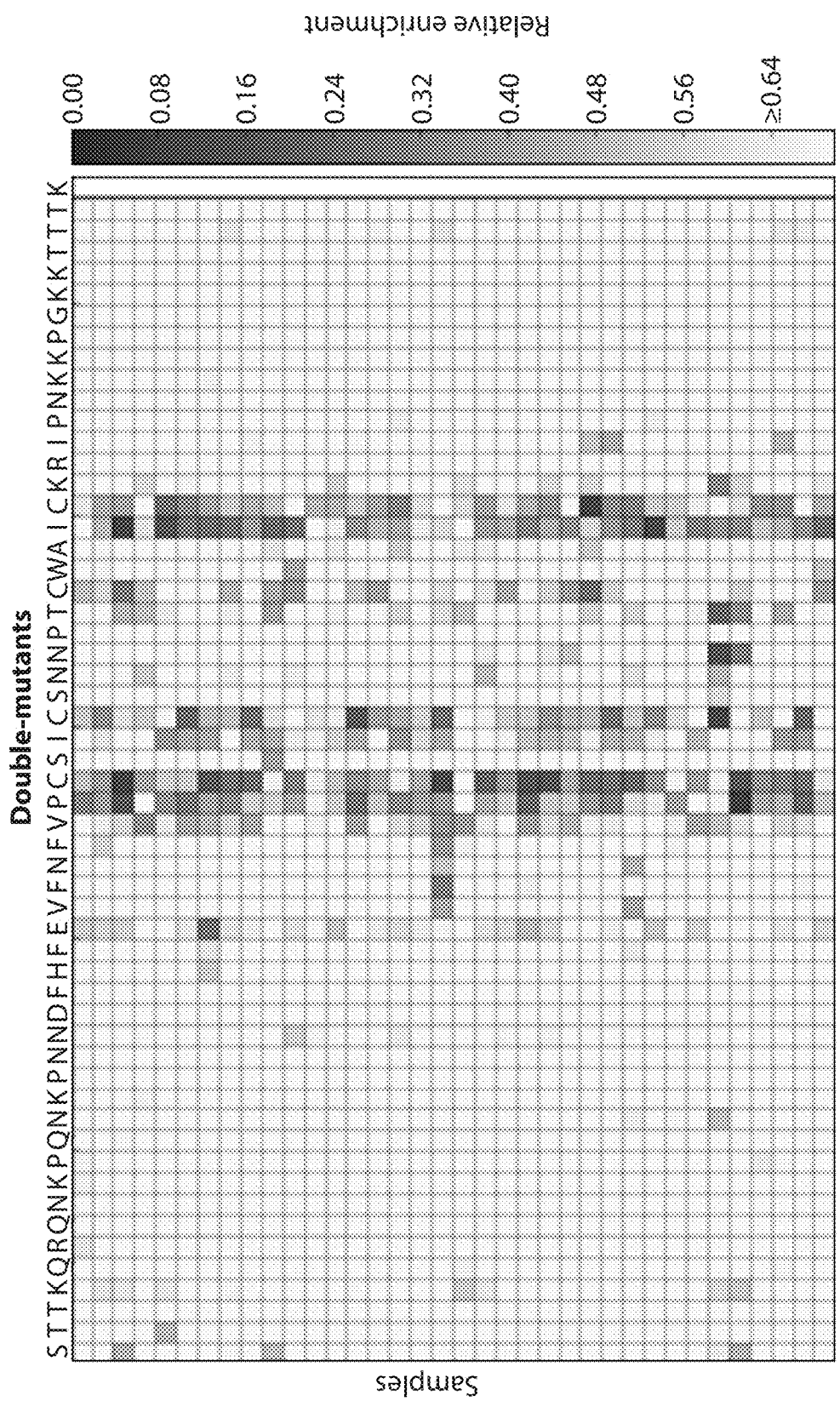
Figure 13C:
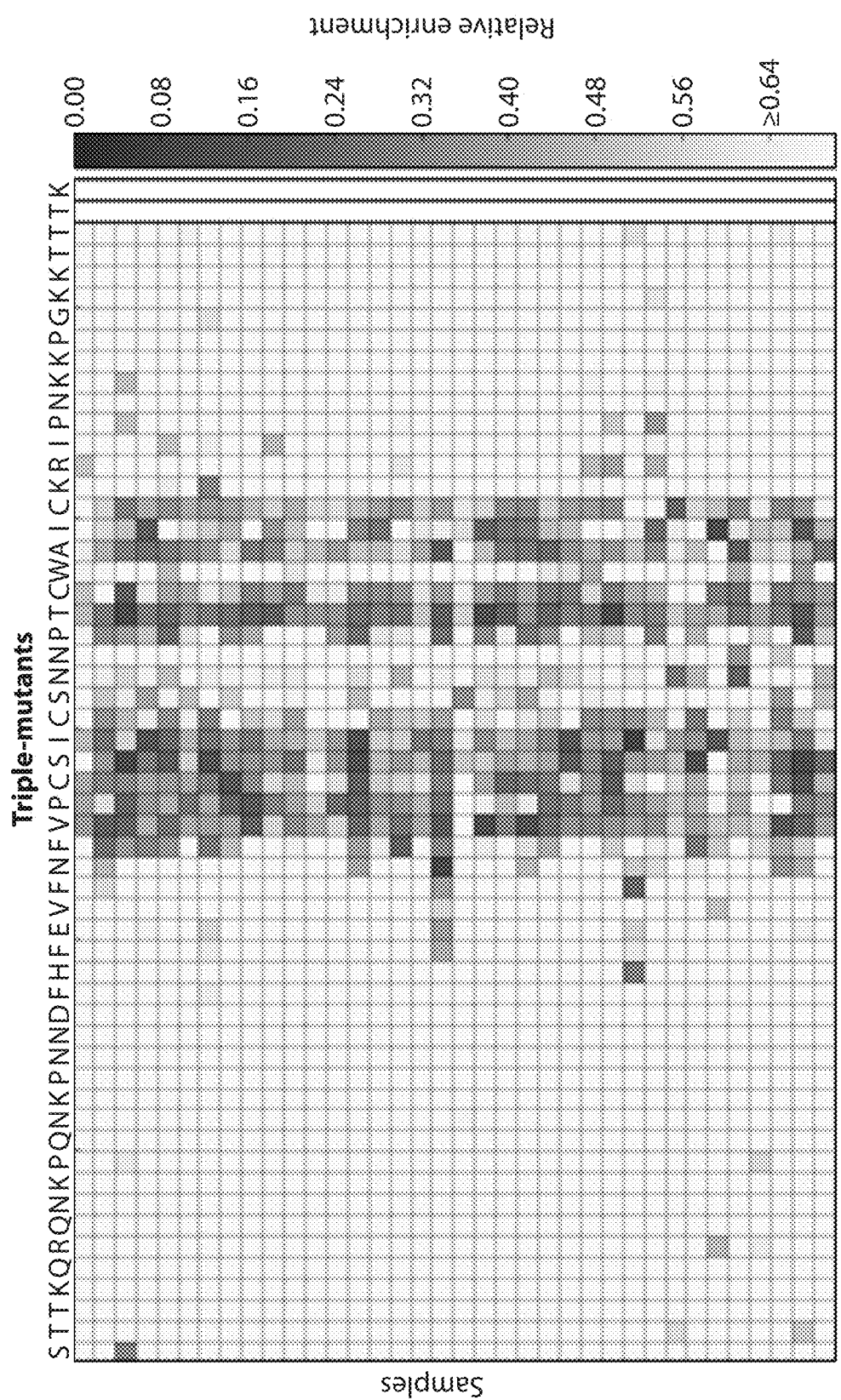
Figure 14A:
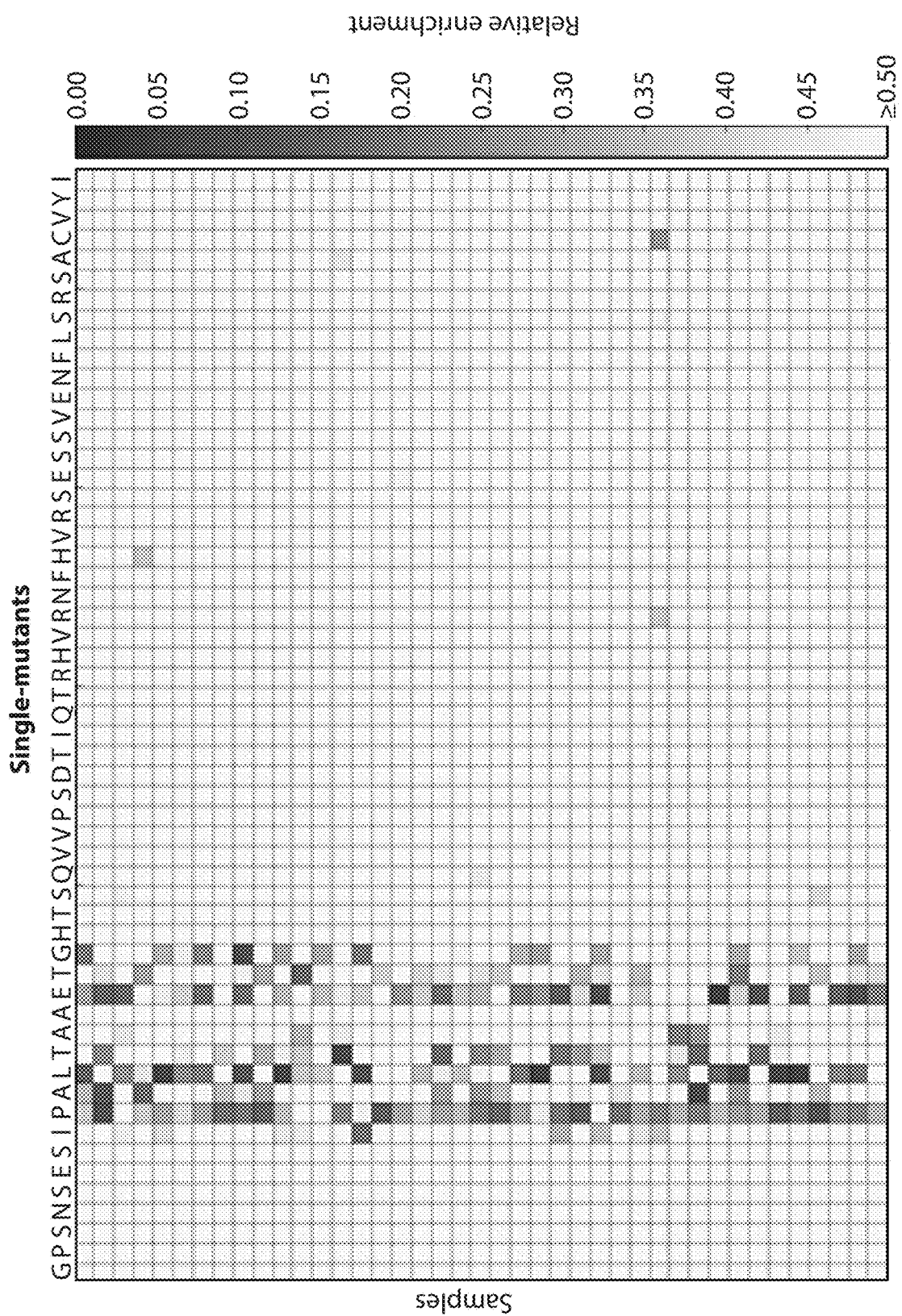
Figure 14B:
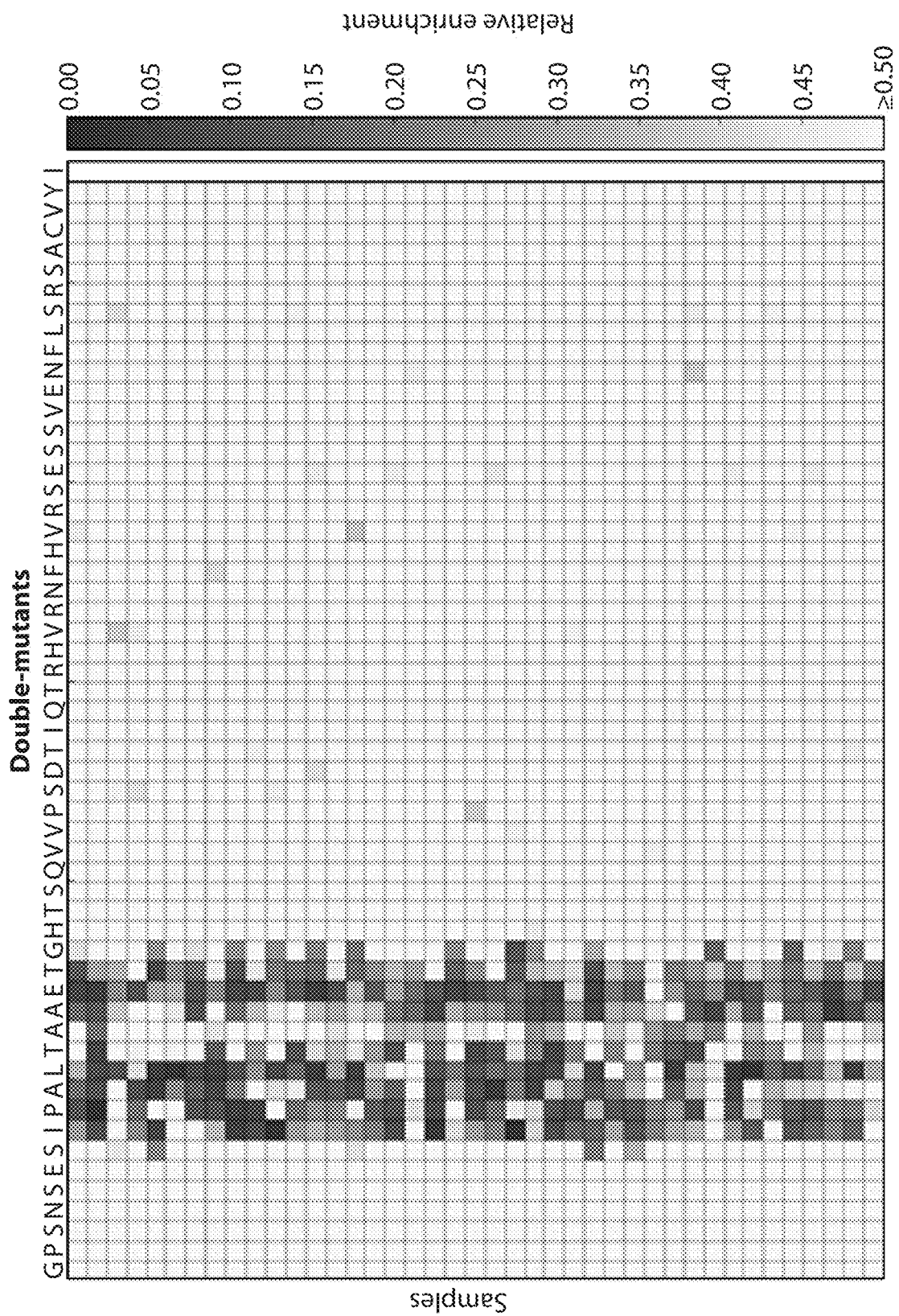
Figure 14C:
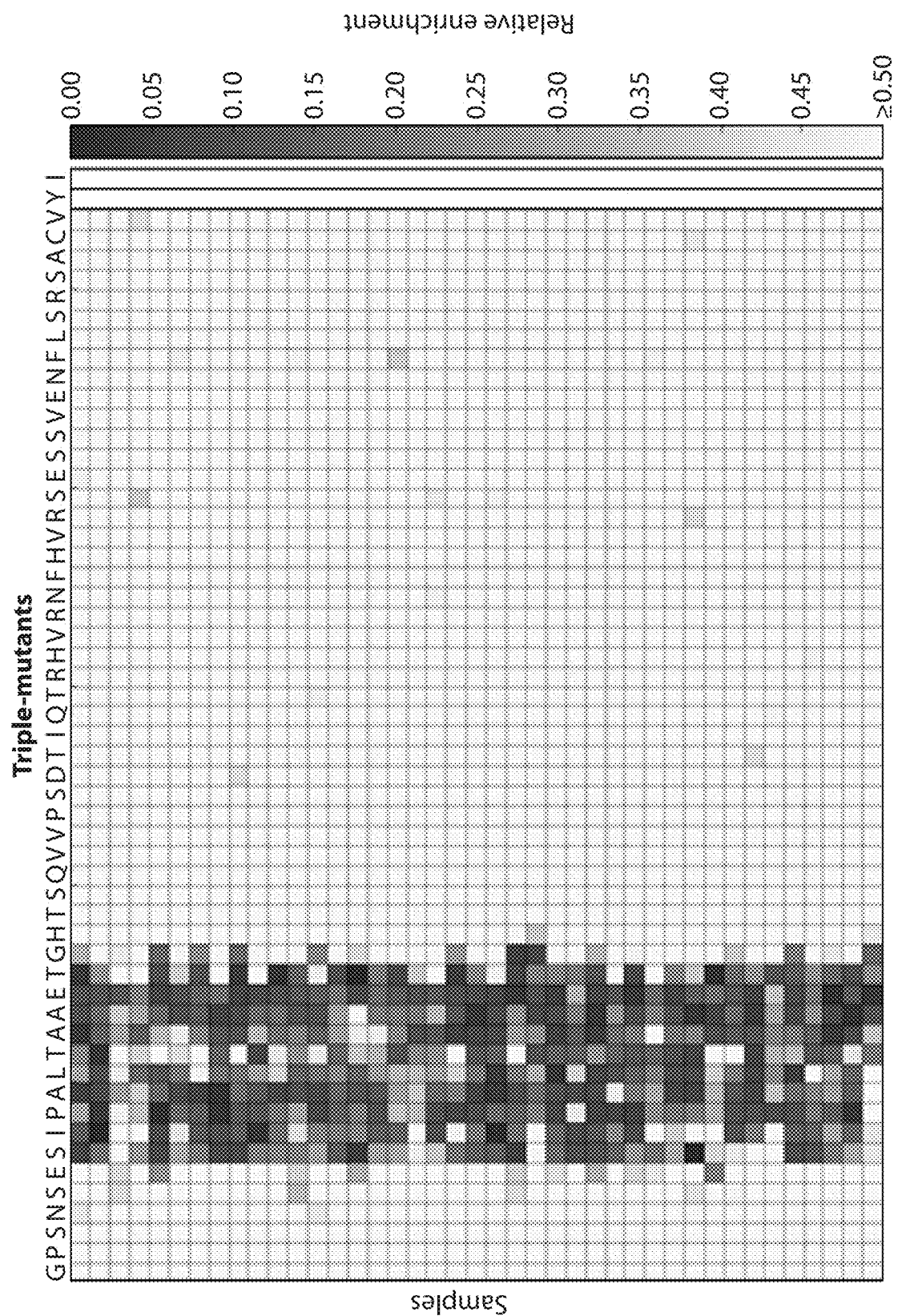
Figure 15A:
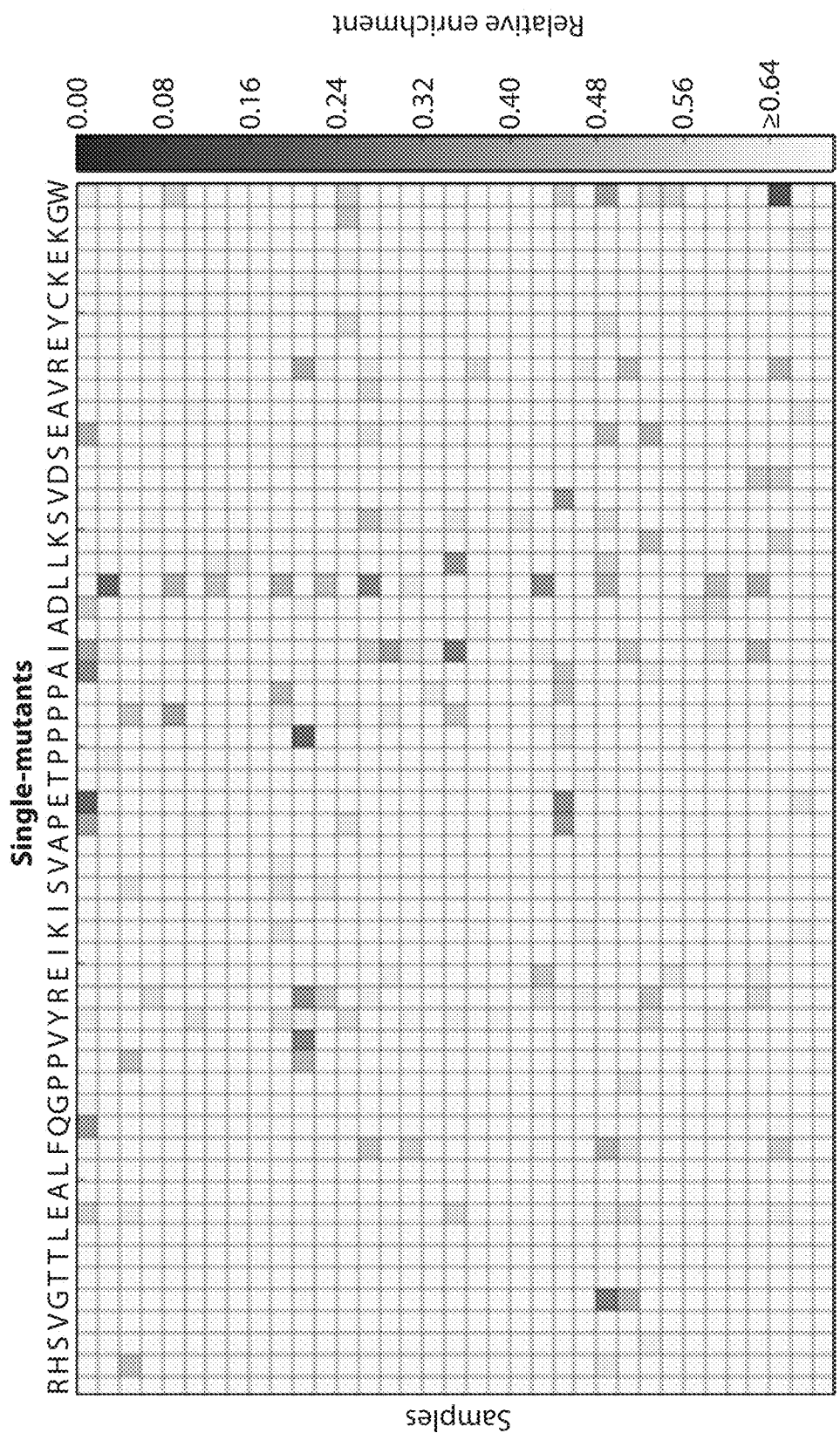
Figure 15B:
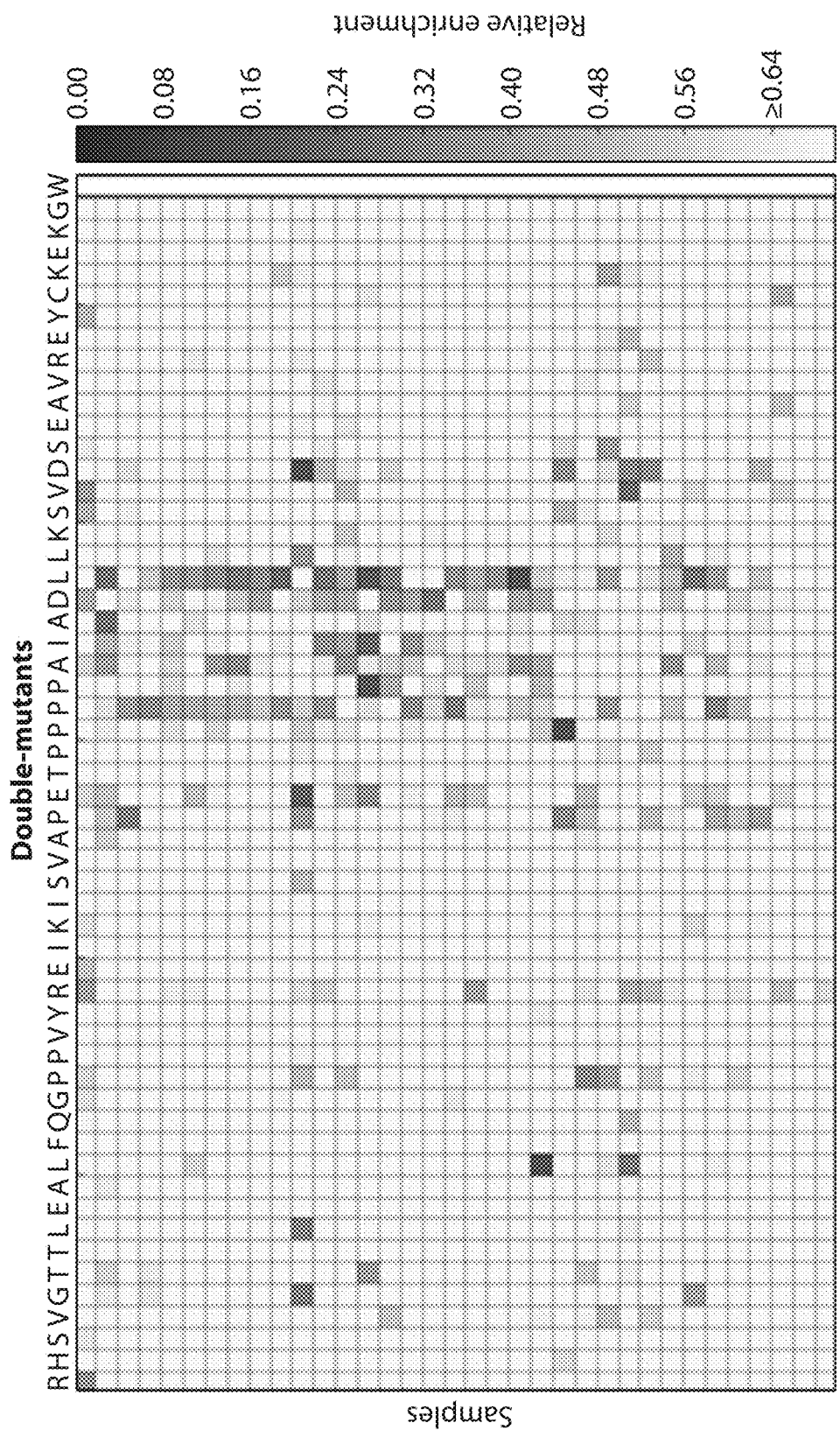
Figure 15C:
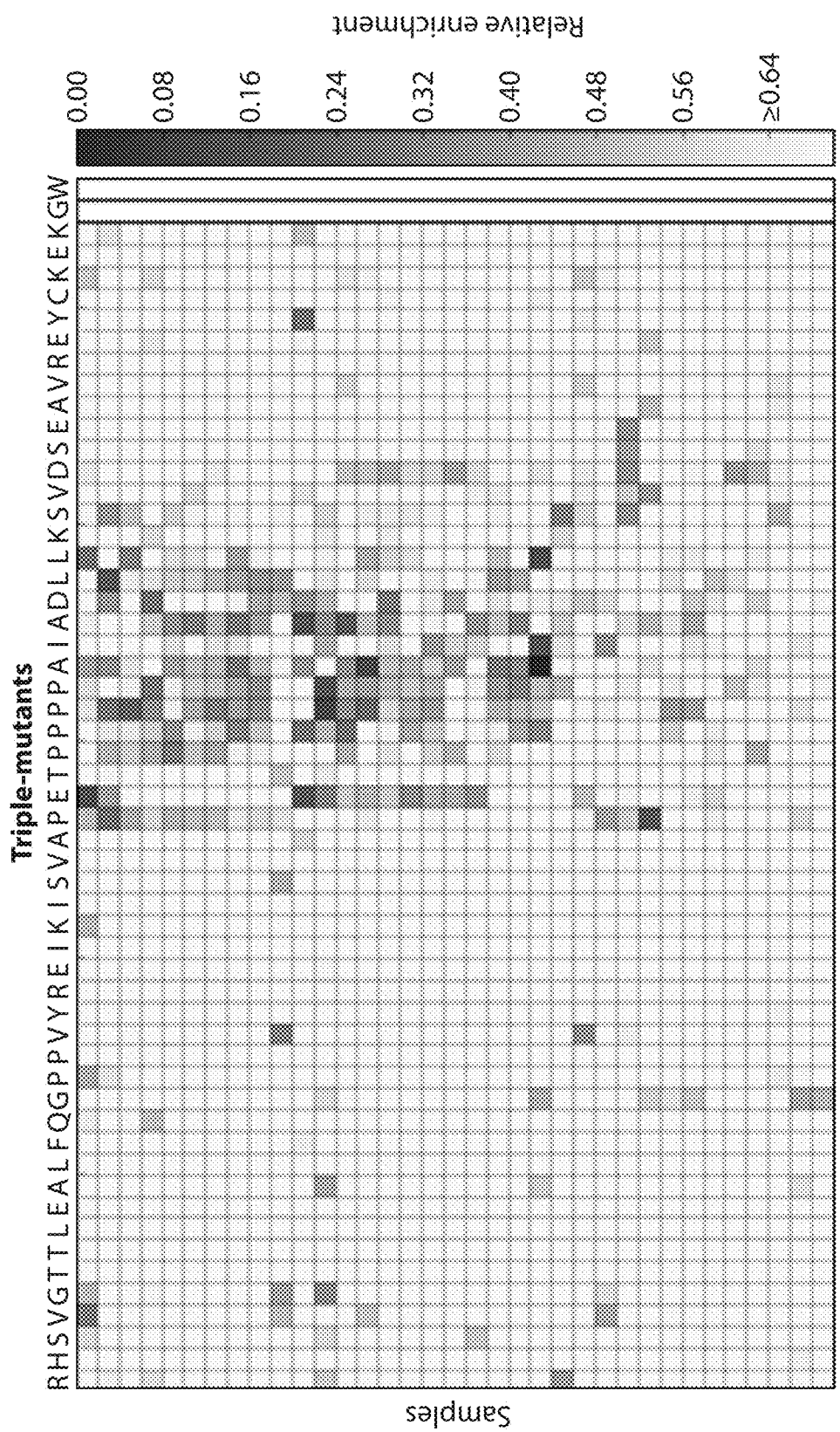
Figure 16A:
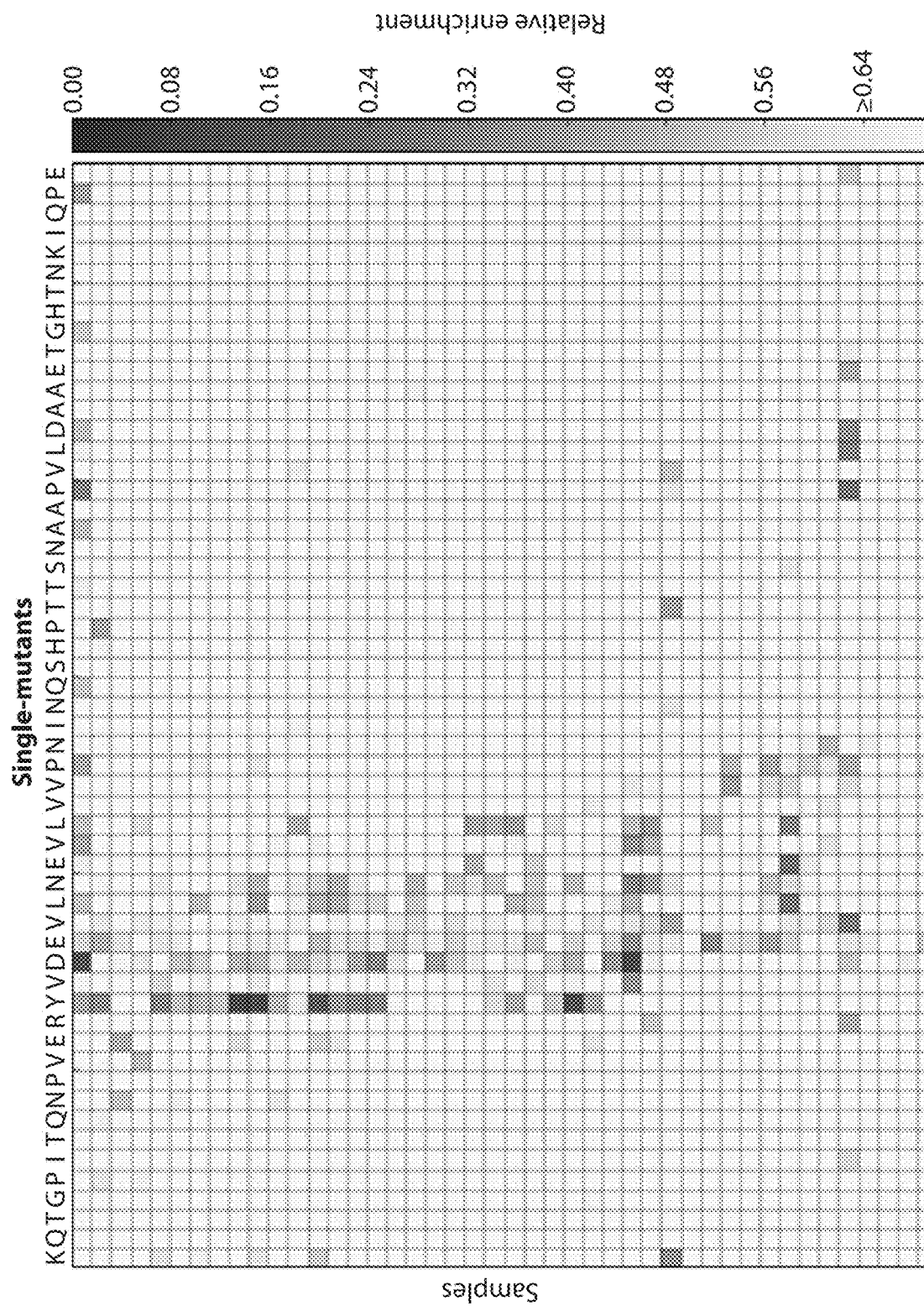
Figure 16B:
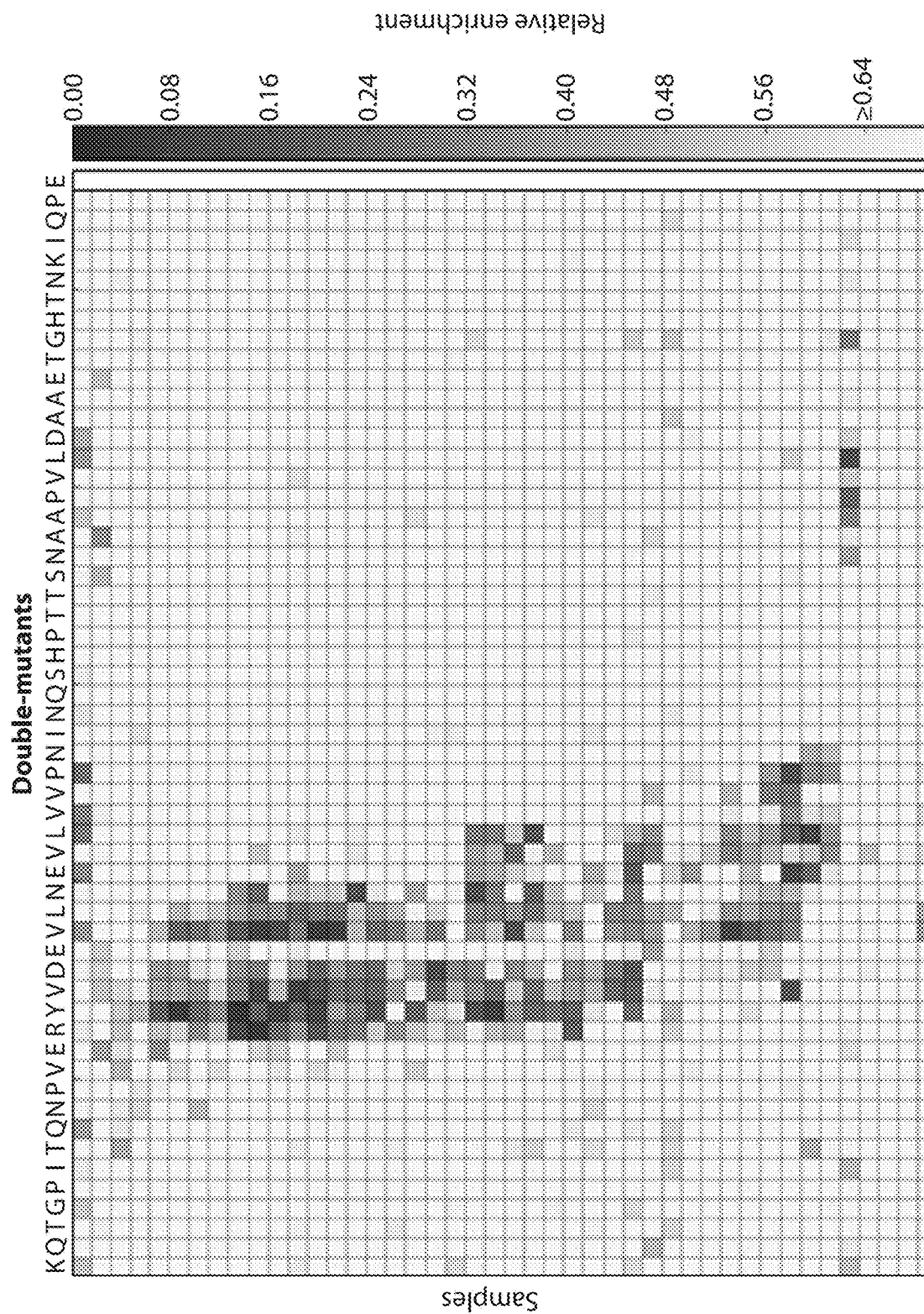
Figure 16C:
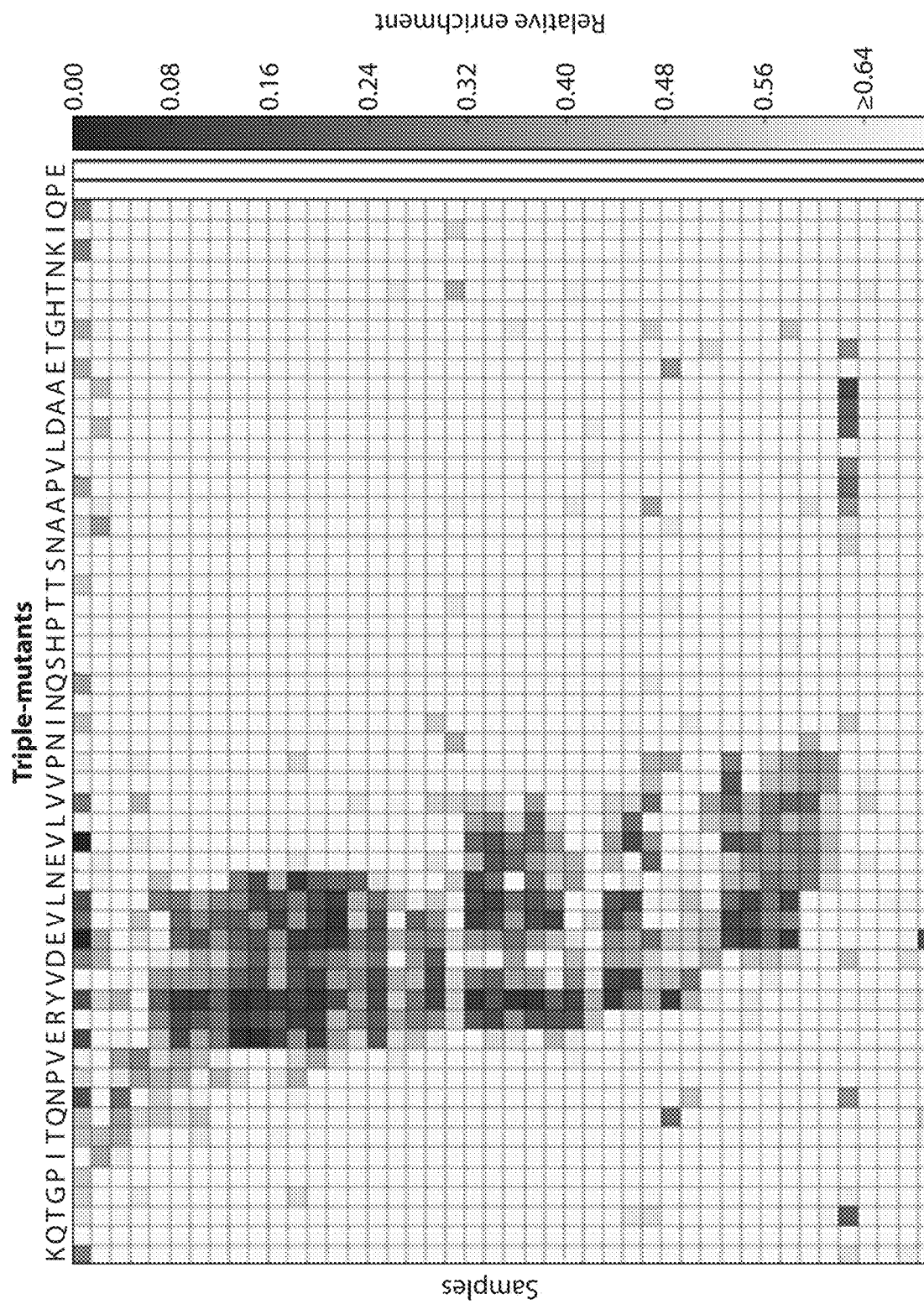
Figure 17A:
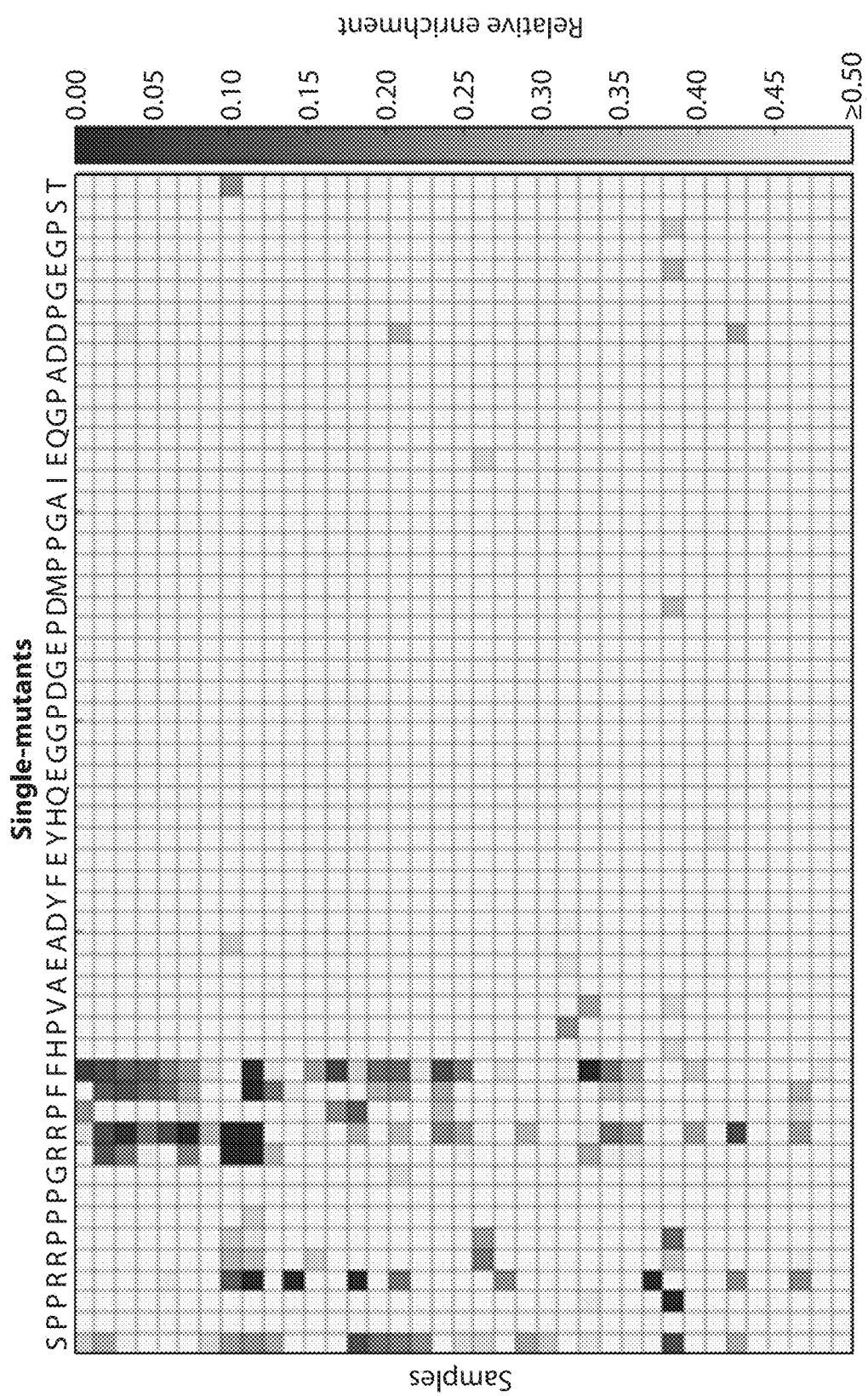
Figure 17B:
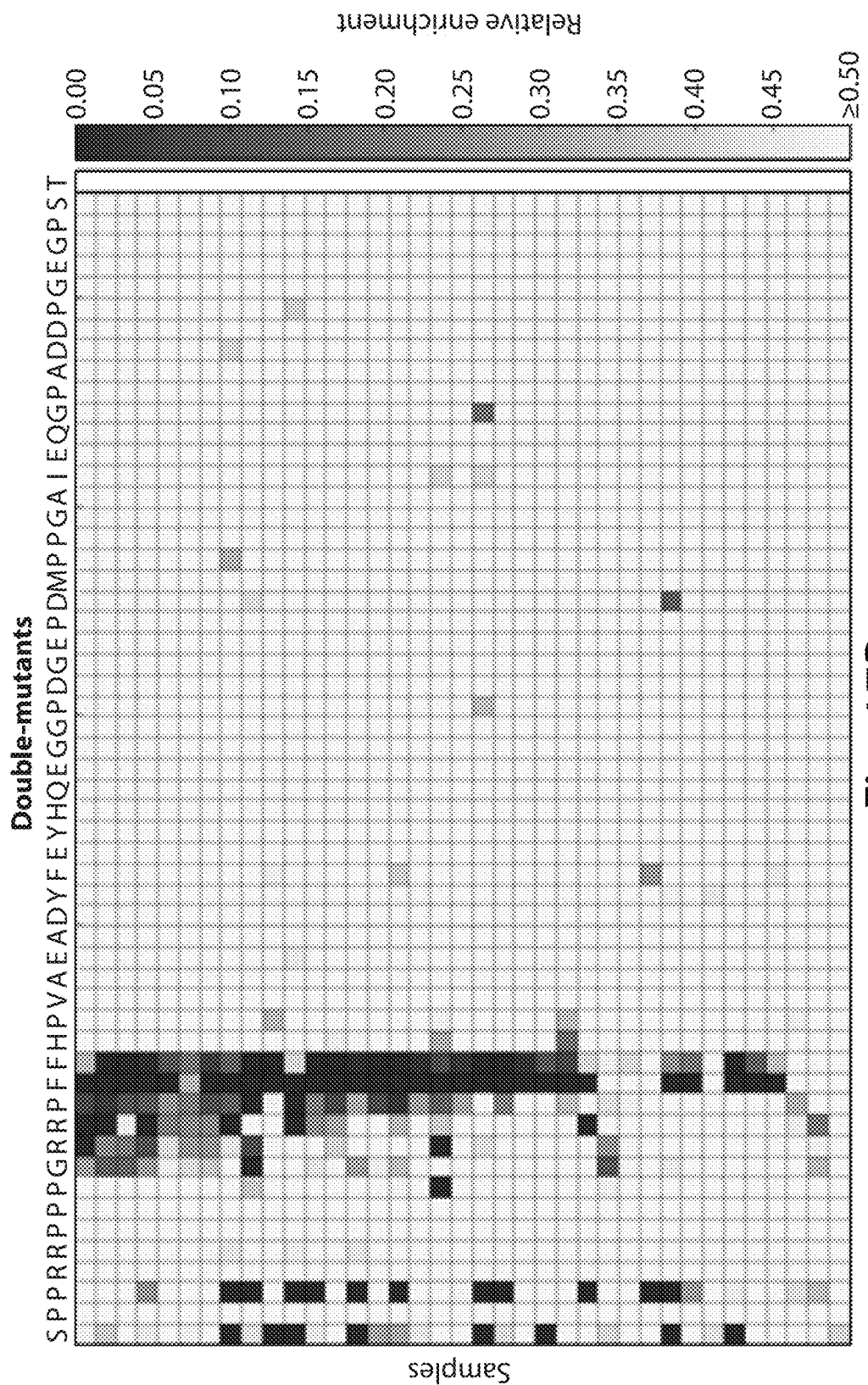
Figure 17C:
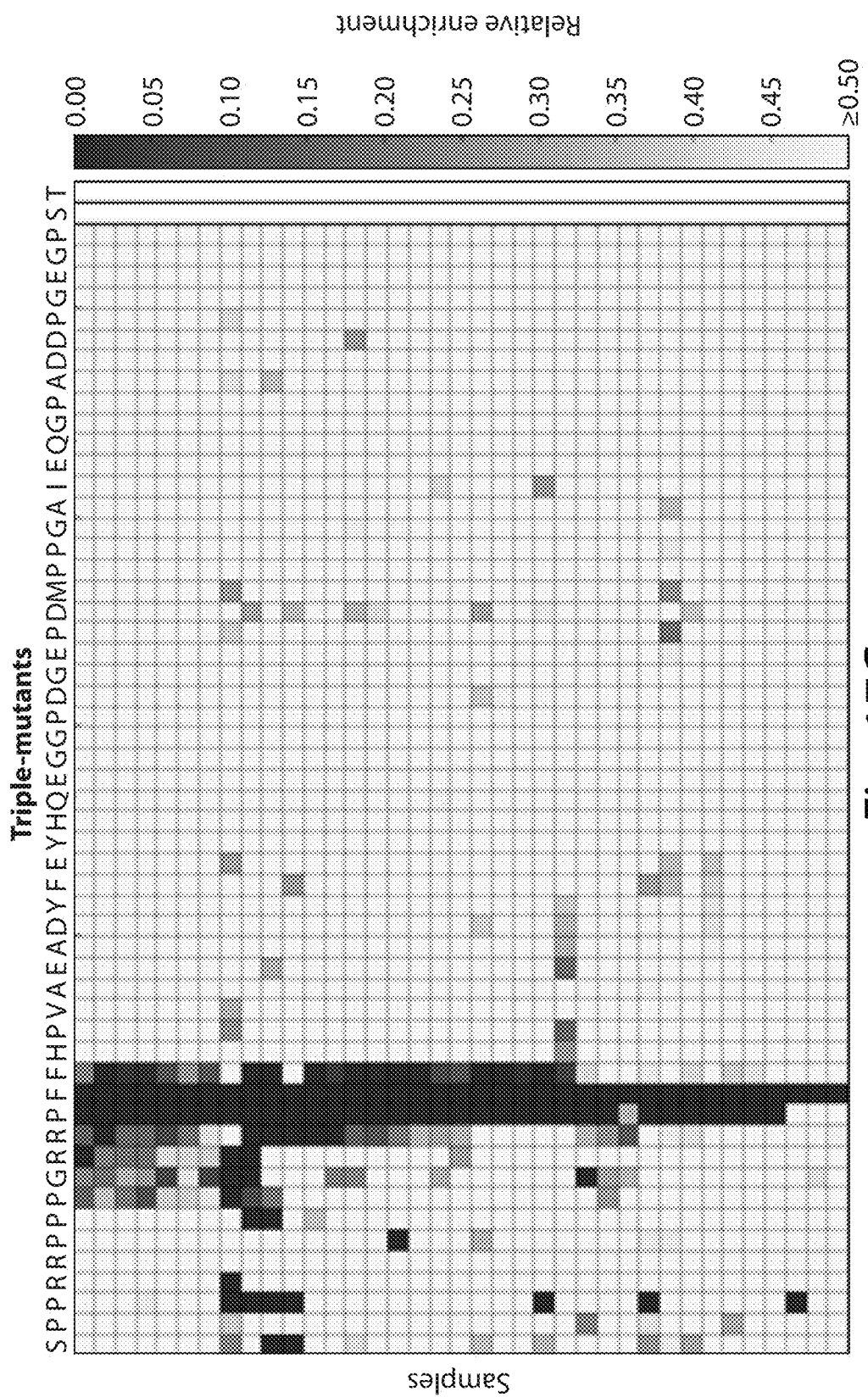

After analyzing responses on the whole virus level, the inventors focused their attention on the specific peptides targeted by these antibodies. They detected antibodies to a total of 3,041 unique peptides in at least 2 samples, and 5,314 in at least 1 sample. Because of the presence of many related peptides in the library and the Immune Epitope Database (IEDB), for the following analysis the inventors consider a peptide "unique" only if it does not contain a continuous 7-residue subsequence (the estimated size of a linear B cell epitope) in common with any other peptide in the database. Analyzed as such, the VirScan database nearly doubles the 1,715 unique human B cell epitopes from human viruses in the IEDB (22). The epitopes identified in our unbiased analysis demonstrate a significant overlap with those contained in the IEDB ($p<10^{-30}$, FIG. 4B). The amount of overlap is even greater for epitopes from viruses that commonly cause infection (FIG. 4D). It may have been possible to detect even more immunogenic peptides in common with the IEDB if more samples from individuals infected with rare viruses were tested. The inventors next analyzed the amino acid composition of recurrently enriched peptides. Enriched peptides tend to have more proline and charged amino acids and fewer hydrophobic amino acids, which is consistent with a previous analysis of B cell epitopes in the IEDB (FIGS. 11A-11B) (23). This trend likely reflects enrichment for amino acids that are surface exposed or can form stronger interactions with antibodies.

B Cell Responses Target Highly Similar Viral Epitopes Across Individuals

Figure 6A:
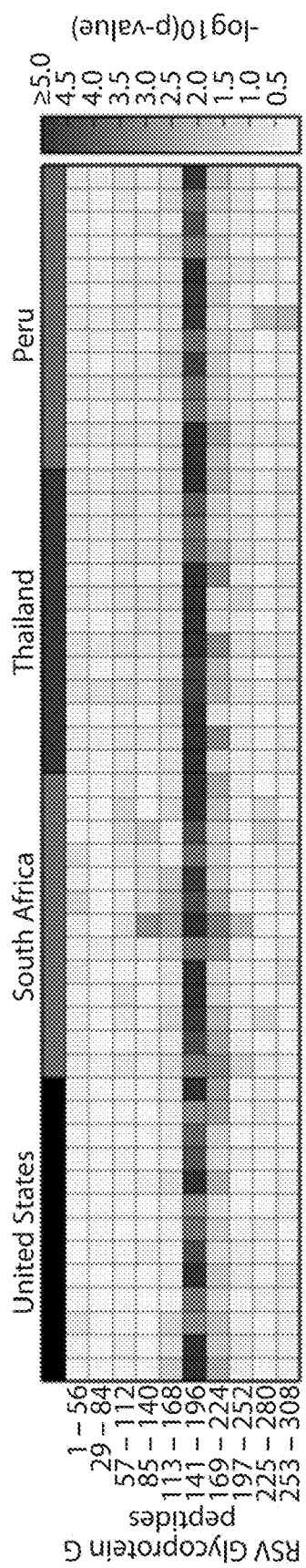
FIGS. 6A-6C show data indicating that the human antivirome response recognizes a similar spectrum of peptides among infected individuals. In the heatmap charts, each row is a peptide tiling across the entire indicated protein and each column is a sample. The bar above each column, labeled at the top of the figure, marks the country of origin for that sample. The samples shown are a subset of individuals with antibodies to at least one peptide from the proteins indicated. The intensity of each cell corresponds to the $-\log_{10}$(p-value) measure of significance of enrichment for a peptide in a sample (greater values indicates stronger antibody response). Data are shown for (FIG. 6A) Human respiratory syncytial virus Attachment Glycoprotein G (G), (FIG. 6B) Human adenovirus C penton protein (L2), and (FIG. 6C) Epstein-Barr virus nuclear antigen 1 (EBNA1). Data shown are the mean of two replicates.

The inventors compared the profile of peptides recognized by the antibody response in different individuals and found that for a given protein, each sample generally only had strong responses against one to three immunodominant peptides (FIG. 6). Surprisingly, it was found that the vast majority of seropositive samples for a given virus recognized the same immunodominant peptides, indicating that the antiviral B cell response is highly stereotyped across individuals. For example, in glycoprotein G from respiratory syncytial virus, there is only a single immunodominant peptide comprising positions 141-196 that is targeted by all samples with detectable antibodies to the protein, regardless of the country of origin (FIG. 6A).

Figure 6B:
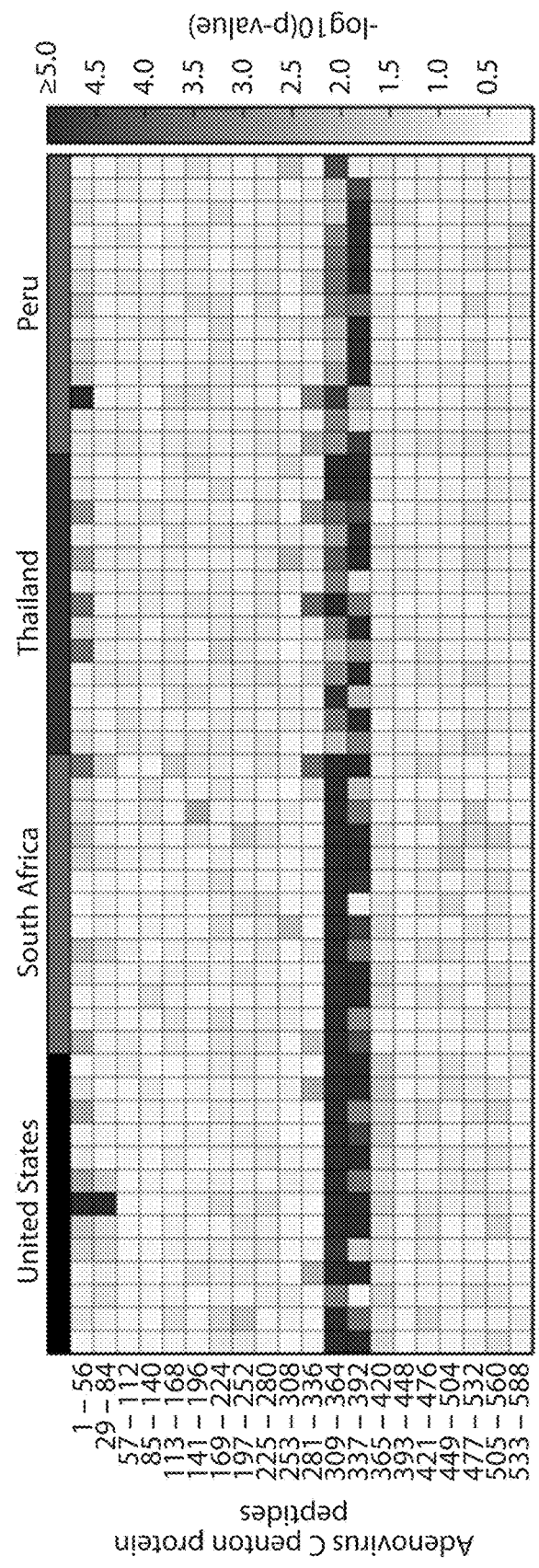
Figure 6C:
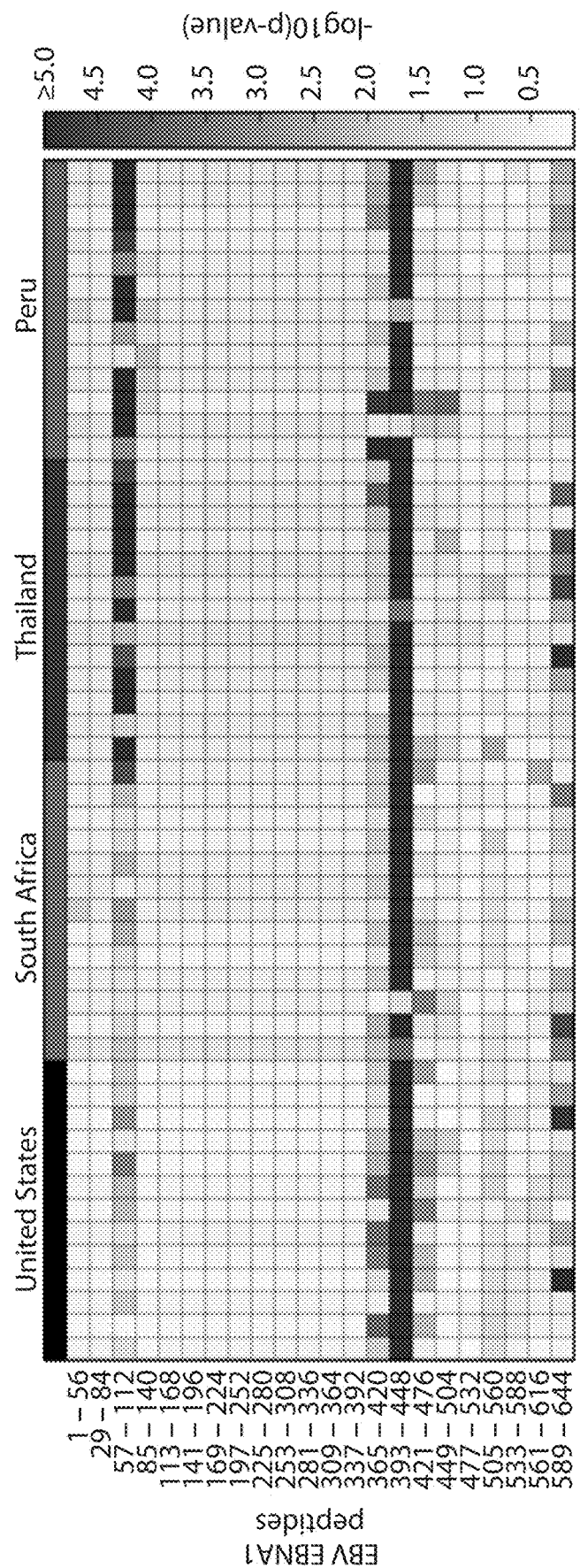
Figure 7A:
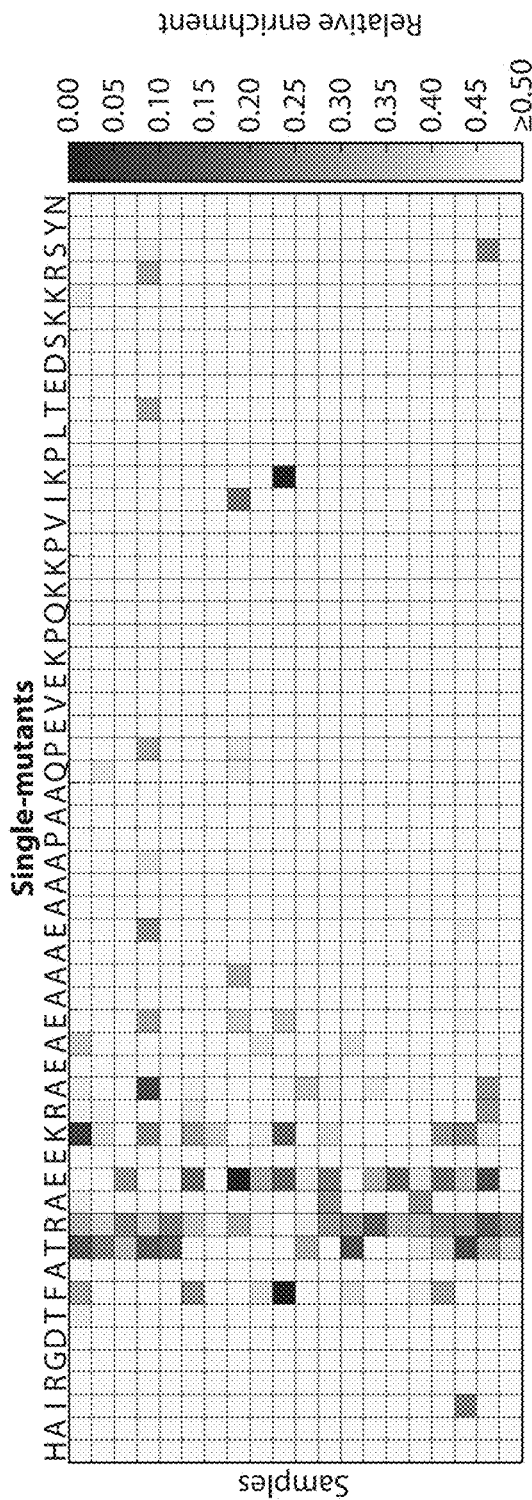
FIGS. 7A-7C Recognition of common epitopes within an immunogenic peptide from human adenovirus C penton protein (L2) across individuals. Each row is a sample. Each column denotes the first mutated position for the (FIG. 7A) single- (SEQ ID NO: 33), (FIG. 7B) double- (SEQ ID NO: 33), and (FIG. 7C) triple-alanine (SEQ ID NO: 33) mutant peptide scanning through. The intensity of each cell indicates the enrichment of the mutant peptide relative to the wild-type. For double-mutants, the last position is blank. The same is true for the last two positions for triple-mutants. Data shown are the mean of two replicates.
Figure 7B:
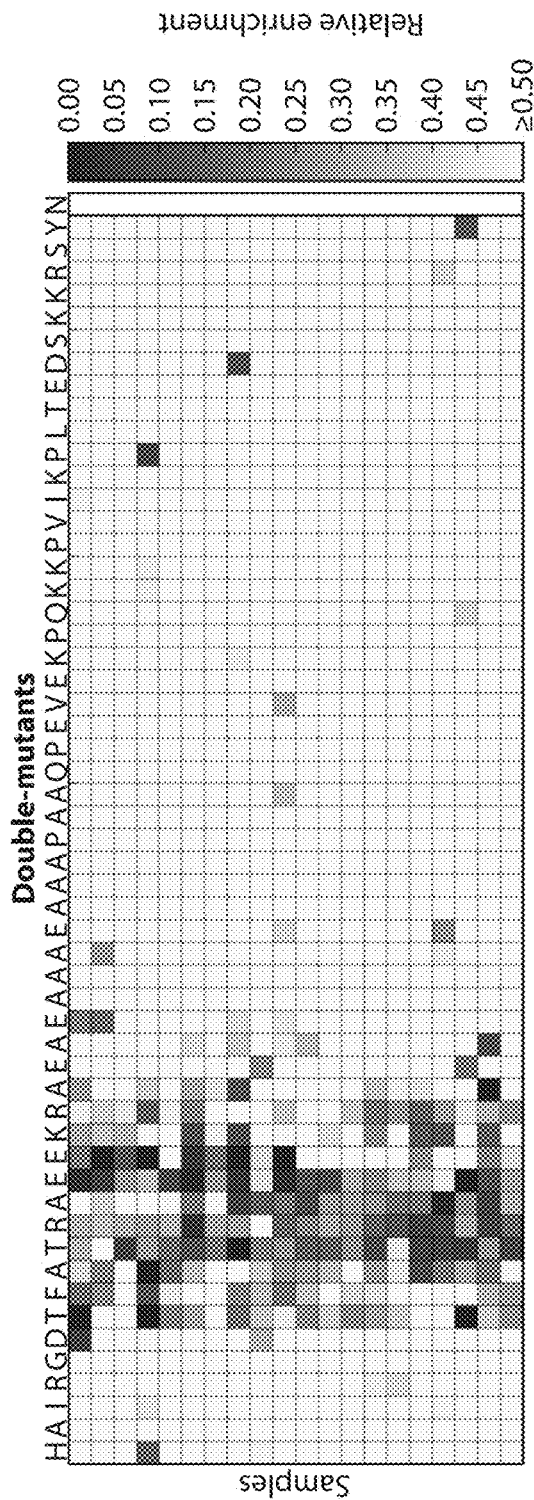
Figure 7C:
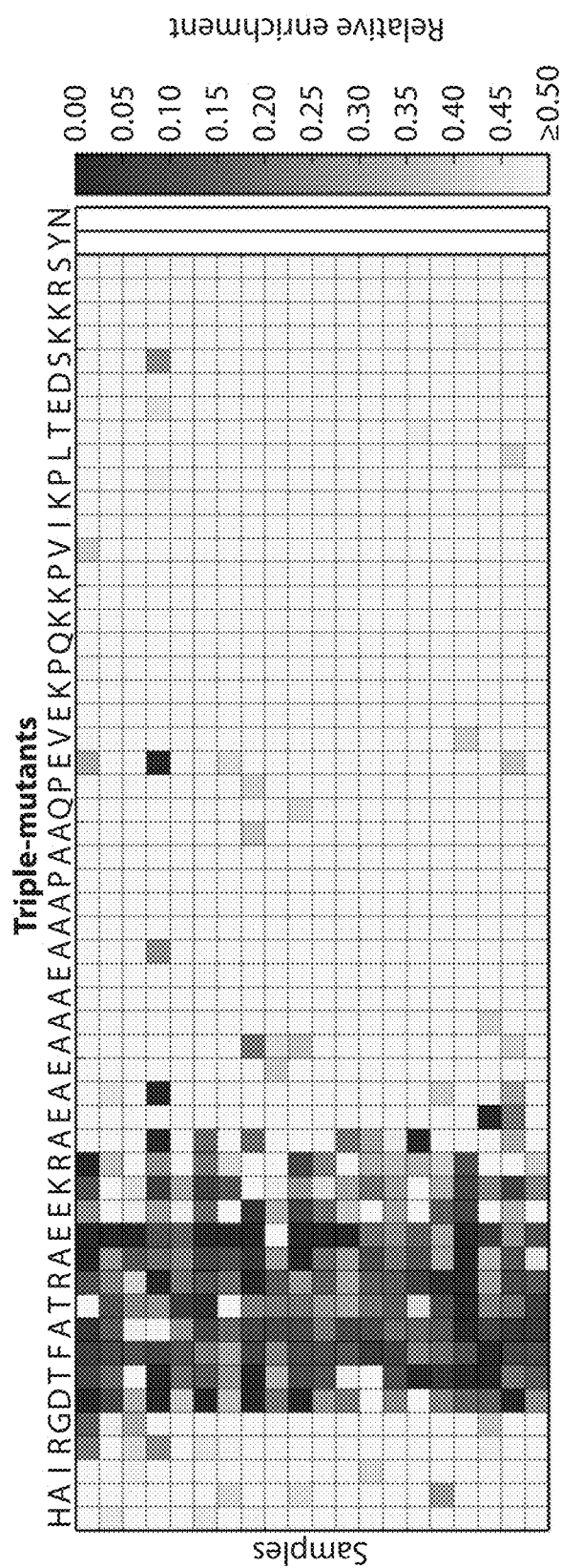

For other antigens, the inventors observed inter-population serological differences. For example, two overlapping peptides from position 309-364 and 337-392 of the penton base protein from Adenovirus C frequently elicited antibody responses (FIG. 6B). However, donors from the United States and South Africa had much stronger responses to peptide 309-364 ($p<10^{-6}$) relative to donors from Thailand and Peru. The inventors observed that for the EBNA1 protein from Epstein Barr virus, donors from all four countries frequently had strong responses to peptide 393-448 and occasionally to peptide 589-644. However, donors from Thailand and Peru had much stronger responses to peptide 57-112 ($p<10^{-6}$) (FIG. 6C). These differences may reflect variation in the strains endemic in each region. In addition, polymorphism of MHC class II alleles, immunoglobulin genes and other modifiers that shape immune responses in each population likely play a role in defining the relative immunodominance of antigenic peptides.

To determine whether the humoral responses that target an immunodominant peptide are actually targeting precisely the same epitope, the inventors constructed single-, double-, and triple-alanine scanning mutagenesis libraries for 8 commonly recognized peptides. These were introduced into the same T7 bacteriophage display vector and subjected to the same immunoprecipitation and sequencing protocol using samples from the United States. Mutants that disrupt the epitope diminish antibody binding affinity and thus peptide enrichment. It was found that for all 8 peptides tested, there was a single, largely contiguous subsequence in which mutations disrupted binding for the majority of samples. As expected, the triple-mutants abolished antibody binding to a greater extent, and the enrichment patterns were similar among single-, double- and triple-mutants of the same peptide (FIG. 7, FIGS. 12-18). For 4 of the 8 peptides, a 9 to 15 amino acid region was critical for antibody recognition in >90% of samples (FIG. 7, FIGS. 12-14). One other peptide had a region of similar size that was critical in about half of the samples (FIG. 15). In another peptide, a single region was important for antibody recognition in the majority of the samples, but the extents of the critical region varied slightly for different samples and occasionally there are donors that recognize a completely separate epitope (FIG. 16). The remaining two peptides contained a single triple mutant that abolished binding in the majority of samples, but the critical region also extended further to different extents depending on the sample (FIGS. 17-18). Surprisingly, in one of these peptides, in addition to the main region surrounding positions 13-14 that is critical for binding, a single G36A mutation disrupted binding in almost half of the samples whereas none of the double- or triple-alanine mutants that also included the adjacent positions (L35, G37) affected binding (FIG. 18). It is possible that G36 plays a role in helping the peptide adopt an antigenic conformation and multiple-mutants containing the adjacent Leu or Gly residues rescue this ability. The inventors occasionally saw other examples of mutations that resulted in patterns of disrupted binding with no simple explanation, illustrating the complexity of antibody-antigen interaction.

Described herein is “VirScan”, a technology for identifying viral exposure and B cell epitopes across the entire known human virome in a single, multiplex reaction using less than a drop of blood. VirScan uses DNA microarray synthesis and bacteriophage display to create a uniform, synthetic representation of peptide epitopes comprising the human virome. Immunoprecipitation and high-throughput DNA sequencing reveals the peptides recognized by antibodies in the sample. VirScan is easily automated in 96-well format to enable high throughput sample processing. Barcoding of samples during PCR enables pooled analysis which can dramatically reduce the per-sample cost. The VirScan approach has several advantages for studying the effect of viruses on the host immune system. By detecting antibody responses, it can identify infectious agents that have been cleared after an effective host response. Current serological methods of antiviral antibody detection typically employ the selection of a single optimized antigen in order to achieve high accuracy. In contrast, VirScan's unique approach does not require such optimization in order to obtain similar performance. VirScan achieves high sensitivity by assaying each virus's complete proteome to detect any antibodies directed to epitopes that can be captured in a 56-residue fragment and high specificity by computationally eliminating cross-reactive antibodies. This unbiased approach identifies exposure to less well-studied viruses for which optimal serological antigens are not known and can be rapidly extended to include new viruses as they are discovered (24).

While sensitive and selective, VirScan also has a few limitations. First, it cannot detect epitopes that require post-translational modifications. Secondly, it cannot detect epitopes that involve discontinuous sequences on protein fragments greater than 56 residues. In principle, the latter can be overcome by using longer peptides or by using alternative protein display technologies such as Parallel Analysis of Translated ORFs (PLATO) (25). Third, VirScan is likely to be less specific compared with certain nucleic acid tests that discern highly related virus strains. However, VirScan demonstrates excellent serological discrimination among similar virus species, such as HSV1 and HSV2 and can even distinguish the genotype of HCV 72% of the time. The inventors envision VirScan will become an important tool for first-pass unbiased serologic screening applications. Individual viruses or viral proteins uncovered in this way can subsequently be analyzed in further detail using more focused assays, as demonstrated for a panel of immunodominant epitopes.

The inventors have demonstrated that VirScan is a sensitive and specific assay for detecting exposure to viruses across the human virome. Because it can be performed in high-throughput and requires minimal sample and cost, VirScan enables rapid and cost-effective screening of large numbers of samples to identify population-level differences in virus exposure across the human virome. In this work, the inventors analyzed over 106 million antibody-viral peptide interactions, in the first comprehensive study of pan-virus serology in a large, diverse population. In doing so we 87 different viral species were detected in 2 or more individuals. This is likely to be an underestimate of the history of viral infection as temporally distant infections may have significantly lower levels of circulating antibodies that are more difficult to detect. In addition, within a species an individual can be infected by multiple distinct strains of that viral species. The inventors identified known and novel differences in virus exposure between groups differing in age, HIV status, and geographic location across four different continents. The results described herein are largely consistent with previous studies, validating the effectiveness of VirScan. For example, cytomegalovirus antibodies were found in significantly higher frequencies in Peru, Thailand, and South Africa whereas Kaposi's sarcoma-associated herpesvirus and HSV1 antibodies were detected more frequently in Peru and South Africa, but not Thailand (15, 26-30). The inventors also uncovered previously undocumented serological differences, such as an increased rate of antibodies against Adenovirus B and respiratory syncytial virus in HIV positive individuals compared to HIV negative individuals. These differences can provide insight into how HIV co-infection alters the balance between host immunity and resident viruses, as well as help to identify pathogens that can increase susceptibility to HIV and other heterologous infections. HIV infection can reduce the immune system's ability to control reactivation of normally dormant resident viruses or to prevent opportunistic infections from taking hold and triggering a strong adaptive immune response. Beyond the epidemiological applications demonstrated here, VirScan can also be applied to identify viral exposures that correlate with disease or other phenotypes in virome-wide association studies.

These result identify a large number of novel B cell epitopes, cumulatively nearly doubling the number of all previously identified viral epitopes. Knowledge of these epitopes and the extent of their recognition can have important implications beyond the identification of potential neutralizing antibody targets or improving B cell epitope prediction algorithms. For example, these epitopes can be used to improve vaccine design by piggybacking on existing immune responses. Fusing a previously detected and globally recognized B cell epitope to an antigen can increase a vaccine's efficacy among a broad population by improving antigen presentation and aiding affinity maturation. B cells recognizing the epitope can act as antigen presenting cells to re-present epitopes on MHC class I and II (31). Antibodies secreted by these B cells can also participate in immune complexes with the antigen, which are critical for follicular dendritic cells to prime class switching and affinity maturation of B cells recognizing other epitopes on the same antigen (32). The inventors have utilized these data to identify globally immunodominant and commonly recognized "public" epitopes that can be used for this purpose. For most species of viruses, a single peptide is recognized in over 70% to 97% of samples positive for that species (Table 3).

globulin heavy and light chain loci is also heavily biased (34). Highly similar or even identical complementarity determining region 3 (CDR3) sequences have been observed in dengue virus specific antibodies from different individuals (35). Without wishing to be bound by theory, slight differences in the antibody CDR3 sequence may subtly alter antibody-antigen interaction, leading to the slight variations observed in the extent of critical epitope regions. It is possible that, rather than being an exception for dengue

TABLE 3

Certain peptides are commonly targeted by the antibody response. The inventors determined the peptide from each species of virus that was most frequently targeted in donors that were exposed to that virus. In each row, the frequency is the percentage of samples positive for the species of virus that had antibodies targeting the peptide sequence shown. The parent protein of the peptide is also listed.

| Species | Protein | Peptide | SEQ ID NO: | % |
|---|---|---|---|---|
| Rhinovirus B | Genome polyprotein | QTDALTEGLSDELEEVIVEKTKQTLASVSSG PKHTQSVPALTANETGATLPTRPSD | 2 | 97.2% |
| Human herpesvirus 5 | Envelope glycoprotein M | TASGEEVAVLSHHDSLESRRLREEEDDDDD EDFEDA | 3 | 92.7% |
| Enterovirus B | Genome polyprotein | IEQKQLLQGDVEEAVNRAVARVADTLPTGP RNSESIPALTAAETGHTSQVVPGDTM | 4 | 94.1% |
| Human herpesvirus 1 | Envelope glycoprotein D | RRHTQKAPKRIRLPHIREDDQPSSHQPLFY | 5 | 88.9% |
| Human herpesvirus 4 | Epstein-Barr nuclear antigen 1 | SPPRRPPPGRRPFFHPVAEADYFEYHQEGG PDGEPDMPPGAIEQGPADDPGEGPST | 6 | 86.3% |
| Human respiratory syncytial virus | Attachment glycoprotein | NKPSTKPRPKNPPKKPKDDYHFEVFNFVPC SICGNNQLCKSICKTIPSNKPKKKPT | 7 | 84.9% |
| Human adenovirus C | Pre-histone-like nucleoprotein | MTQGRRGNVYWVRDSVSGLRVPVRTRPPRN | 8 | 80.1% |
| Enterovirus C | Genome polyprotein | QGALTLSLPKQQDSLPDTKASGPAHSKEVP ALTAVETGATNPLAPSDTVQTRHVVQ | 9 | 85.4% |
| Human herpesvirus 3 | Envelope glycoprotein C | PDPAVAPTSAASRKPDPAVAPTSAASRKPD PAVAPTSAATRKPDPAVAPTSAASRK | 10 | 76.9% |
| Norwalk virus | Non-structural polyprotein | LSSMAITFKRALGARPKQPPPREILQRPPRP PTPELVKKIPPPPPNGEDELVVSYS | 11 | 84.6% |
| Human immunodeficiency virus 1 | Envelope glycoprotein gp160 | ERYLKDQQLLGIWGCSGKLICTTAVPWNAS WSNKSLEQIWNNMTWMEWDREINNYT | 12 | 75.8% |
| Influenza A virus | Hemagglutinin | LGHHAVPNGTLVKTITNDQIEVTNATELVQ SSSTGRICDSPHRILDGKNCTLIDAL | 13 | 47.9% |

The inventors identified a set of two peptides that together are recognized by >95% of all screened samples and a set of five peptides that together are recognized in >99% of screened samples. They also found that the B cell response to viral epitopes is highly similar between individuals across many viral proteins. Without wishing to be bound by theory, one possible model for this striking similarity is that these regions possess properties favorable for antigenicity, such as accessibility. Another model is that the same or highly similar B cell receptor sequences that recognize these epitopes are commonly generated. Identical T cell receptor sequences ("public" clonotypes) have been found in multiple individuals and are thought to be the result of biases during the recombination process that favor certain amino acid sequences (33). V(D)J recombination of the immunospecific antibodies, this represents a general phenomenon: inherent biases in V(D)J recombination generate the same or similar antibodies in multiple individuals that recognize highly similar epitopes.

In conclusion, VirScan is a powerful new technology that enables human virome-wide exploration—at the epitope level—of immune responses in large numbers of individuals. The inventors have demonstrated its effectiveness for determining viral exposure and characterizing viral B cell epitopes in high throughput and at high resolution. These studies have revealed intriguing general properties of the human immune system, both at the individual and population scale. VirScan is an important tool in uncovering the effect of host-virome interactions on human health and disease and can easily be expanded to include other human pathogens such as bacteria, fungi and protozoa.

REFERENCES

1. K. M. Wylie, G. M. Weinstock, G. A. Storch, Emerging view of the human virome. *Transl. Res.* 160 (2012), pp. 283-290.
2. B. a Duerkop, L. V Hooper, Resident viruses and their interactions with the immune system. *Nat. Immunol.* 14, 654-9 (2013).
3. E. S. Barton et al., Herpesvirus latency confers symbiotic protection from bacterial infection. *Nature.* 447, 326-329 (2007).
4. E. F. Foxman, A. Iwasaki, Genome-virome interactions: examining the role of common viral infections in complex disease. *Nat. Rev. Microbiol.* 9, 254-264 (2011).
5. M. Lecuit, M. Eloit, The human virome: New tools and concepts. *Trends Microbiol.* 21 (2013), pp. 510-515.
6. I. De Vlaminck et al., XTemporal response of the human virome to immunosuppression and antiviral therapy. *Cell.* 155 (2013), doi:10.1016/j.cell.2013.10.034.
7. E. Hammarlund et al., Duration of antiviral immunity after smallpox vaccination. *Nat. Med.* 9, 1131-1137 (2003).
8. H. B. Larman et al., Autoantigen discovery with a synthetic human peptidome. *Nat. Biotechnol.* 29, 535-541 (2011).
9. The UniProt Consortium, Activities at the Universal Protein Resource (UniProt). *Nucleic Acids Res.* 42, D191-8 (2014).
10. H. B. Larman et al., PhIP-Seq characterization of autoantibodies from patients with multiple sclerosis, type 1 diabetes and rheumatoid arthritis. *J. Autoimmun.* 43, 1-9 (2013).
11. C. Bialecki, H. M. Feder, J. M. Grant-Kels, The six classic childhood exanthems: a review and update. *J. Am. Acad. Dermatol.* 21, 891-903 (1989).
12. J. H. Lee, W. K. Roth, S. Zeuzem, Evaluation and comparison of different hepatitis C virus genotyping and serotyping assays. *J. Hepatol.* 26, 1001-1009 (1997).
13. H. F. L. Wertheim et al., Key role for clumping factor B in *Staphylococcus aureus* nasal colonization of humans. *PLoS Med.* 5, 0104-0112 (2008).
14. R. A. Manz, A. E. Hauser, F. Hiepe, A. Radbruch, Maintenance of serum antibody levels. *Annu. Rev. Immunol.* 23, 367-386 (2005).
15. S. A. S. Staras et al., Seroprevalence of cytomegalovirus infection in the United States, 1988-1994. *Clin. Infect. Dis.* 43, 1143-1151 (2006).
16. M. A. Reynolds, D. Kruszon-Moran, A. Jumaan, D. S. Schmid, G. M. McQuillan, Varicella seroprevalence in the U.S.: data from the National Health and Nutrition Examination Survey, 1999-2004. *Public Health Rep.* 125, 860-9.
17. J. I. Cohen, Epstein-Barr virus infection. *N. Engl. J. Med.* 343, 481-492 (2000).
18. L. Dong et al., A combination of serological assays to detect human antibodies to the avian influenza a H7N9 virus. *PLoS One.* 9 (2014), doi:10.1371/journal.pone.0095612.
19. P. Patel et al., Prevalence and Risk Factors Associated With Herpes Simplex Virus-2 Infection in a Contemporary Cohort of HIV-Infected Persons in the United States. *Sex. Transm. Dis.* 39 (2012), pp. 154-160.
20. C. T. Stover et al., Prevalence of and risk factors for viral infections among human immunodeficiency virus (HIV)-infected and high-risk HIV-uninfected women. *J. Infect. Dis.* 187, 1388-96 (2003).
21. E. A. Engels et al., Risk factors for human herpesvirus 8 infection among adults in the United States and evidence for sexual transmission. *J. Infect. Dis.* 196, 199-207 (2007).
22. R. Vita et al., The Immune Epitope Database 2.0. *Nucleic Acids Res.* 38 (2009), doi:10.1093/nar/gkp1004.
23. H. Singh, H. R. Ansari, G. P. S. Raghava, Improved Method for Linear B-Cell Epitope Prediction Using Antigen's Primary Sequence. *PLoS One.* 8 (2013), doi: 10.1371/journal.pone.0062216.
24. J. L. Mokili, F. Rohwer, B. E. Dutilh, Metagenomics and future perspectives in virus discovery. *Curr. Opin. Virol.* 2 (2012), pp. 63-77.
25. J. Zhu et al., Protein interaction discovery using parallel analysis of translated ORFs (PLATO). *Nat. Biotechnol.* 31, 331-4 (2013).
26. Y. Urwijitaroon, S. Teawpatanataworn, A. Kitjareontarm, Prevalence of cytomegalovirus antibody in Thainortheastern blood donors. *Southeast Asian J. Trop. Med. Public Health.* 24 Suppl 1, 180-182 (1993).
27. M. J. Cannon, D. S. Schmid, T. B. Hyde, Review of cytomegalovirus seroprevalence and demographic characteristics associated with infection. *Rev. Med. Virol.* 20 (2010), pp. 202-213.
28. S. Mohanna et al., Human herpesvirus-8 in Peruvian blood donors: a population with hyperendemic disease? *Clin. Infect. Dis.* 44, 558-561 (2007).
29. D. Ablashi et al., Seroprevalence of human herpesvirus-8 (HHV-8) in countries of Southeast Asia compared to the USA, the Caribbean and Africa. *Br. J. Cancer.* 81, 893-7 (1999).
30. J. S. Smith, N. J. Robinson, Age-specific prevalence of infection with herpes simplex virus types 2 and 1: a global review. *J. Infect. Dis.* 186 Suppl, S3-S28 (2002).
31. A. Heit et al., CpG-DNA aided cross-priming by cross-presenting B cells. *J. Immunol.* 172, 1501-1507 (2004).
32. Y. Aydar, S. Sukumar, A. K. Szakal, J. G. Tew, The influence of immune complex-bearing follicular dendritic cells on the IgM response, Ig class switching, and production of high affinity IgG. *J. Immunol.* 174, 5358-66 (2005).
33. M. F. Quigley et al., Convergent recombination shapes the clonotypic landscape of the naive T-cell repertoire. *Proc. Natl. Acad. Sci. U.S.A.* 107, 19414-19419 (2010).
34. K. J. L. Jackson, M. J. Kidd, Y. Wang, A. M. Collins, The shape of the lymphocyte receptor repertoire: lessons from the B cell receptor. *Front. Immunol.* 4, 263 (2013).
35. P. Parameswaran et al., Convergent antibody signatures in human dengue. *Cell Host Microbe.* 13, 691-700 (2013).
36. M. Meyer, M. Kircher, Illumina sequencing library preparation for highly multiplexed target capture and sequencing. *Cold Spring Harb. Protoc.* 5 (2010), doi: 10.1101/pdb.prot5448.
37. B. Langmead, C. Trapnell, M. Pop, S. L. Salzberg, Ultrafast and memory-efficient alignment of short DNA sequences to the human genome. *Genome Biol,* 1-10 (2009).

Example 7: Exemplary Materials and Methods

Patient Samples:

Specimens originating from human donors were collected after informed written consent was obtained and under a protocol approved by the local governing human research protection committee. Secondary use of all samples for the purposes of this work was exempted by the Brigham and Women's Hospital Institutional Review Board (Protocol #: 2013P001337). Samples included donors residing in Thailand (n=48), donors residing in Peru (n=48), donors residing in South Africa (n=48), and the remaining donors residing in the Unites States including HIV+ donors (n=61) and HCV+ donors (n=26). All serum and plasma samples were stored in aliquots at −80° C. until use.

Design and Cloning of Viral Peptide and Scanning Mutagenesis Library Sequences:

For the virome peptide library, the inventors first downloaded all protein sequences in the UniProt database from viruses with human host and collapsed on 90% sequence identity. The clustering algorithm UniProt represents each group of protein sequences sharing at least 90% sequence similarity with a single representative sequence. Then, the inventors created 56 aa peptide sequences tiling through all the proteins with 28 aa overlap. The inventors reverse translated these peptide sequences into DNA codons optimized for expression in *E. coli*, making synonymous mutations when necessary to avoid restriction sites used in subsequent cloning steps (EcoRI and XhoI). Finally, the inventors added the adapter sequence "aGGAATTCCGCTGCGT" (SEQ ID NO 14) to the 5' end and "CAGGgaagagctcgaa" (SEQ ID NO: 15) to the 3' end to form the 200 nt oligonucleotide sequences.

For the scanning mutagenesis library, the inventors first took the sequences of the peptides to be mutagenized. For each peptide, they made all single-, double-, and triple-mutants sequences scanning through the whole peptide. Non-alanine amino acids were mutated to alanine and alanines were mutated to glycine. The inventors reverse translated these peptide sequences into DNA codons, making synonymous mutations when necessary to avoid restriction sites used in subsequent cloning steps (EcoRI and XhoI). The inventors also made synonymous mutations to ensure that the 50 nt at the 5' end of peptide sequence is unique to allow unambiguous mapping of the sequencing results. Finally, the inventors added the adapter sequence "aGGAATTCCGCTGCGT" (SEQ ID NO: 14) to the 5' end and "CAGGgaagagctcgaa" (SEQ ID NO: 15) to the 3' end to form the 200 nt oligonucleotide sequences.

The 200 nt oligonucleotide sequences were synthesized on a releasable DNA microarray. DNA was PCR amplified using the primers T7-PFA (aatgatacggcggGAATTCCGCTGCGT) (SEQ ID NO: 16) and T7-PRA (caagcagaagACTCGAGCTCTTCCCTG) (SEQ ID NO: 17), the product was digested with EcoRI and XhoI, and the fragment was cloned into the EcoRI/SalI site of the T7FNS2 vector (8). The resulting library was packaged into T7 bacteriophage using the T7 Select Packaging Kit (EMD Millipore) and amplified using the manufacturer suggested protocol.

Phage Immunoprecipitation and Sequencing:

The inventors performed phage immunoprecipitation and sequencing using a slightly modified version of previously published PhIP-Seq protocols (8, 10). First, the inventors blocked each well of a 96 deep-well plate with 1 mL of 3% BSA in TBST overnight on a rotator at 4° C. To each pre-blocked well, the inventors added sera or plasma containing approximately 2 µg of IgG (quantified using a Human IgG ELISA Quantitation Set (Bethyl Laboratories)) and 1 mL of the bacteriophage library diluted to approximately $2 \times 10^5$ fold representation ($2 \times 10^{10}$ pfu for a library of $10^5$ clones) in phage extraction buffer (20 mM Tris-HCl, pH 8.0, 100 mM NaCl, 6 mM MgSO$_4$). Two technical replicates were performed for each sample. The antibodies were permitted to bind the phage overnight on a rotator at 4° C. The next day, 20 µL each of magnetic Protein A and Protein G Dynabeads (INVITROGEN) was added to each well and immunoprecipitation was allowed to occur for 4 h on a rotator at 4° C. Using a 96-well magnetic stand, the beads were washed three times with 400 µL of PhIP-Seq wash buffer (50 mM Tris-HCl, pH 7.5, 150 mM NaCl, 0.1% NP-40). After the final wash, the beads were resuspended in 40 µL of water and the phage lysed at 95° C. for 10 min. We also lysed phage from the library before immunoprecipitation ("input") and after immunoprecipitation with beads alone.

The inventors prepared the DNA for multiplexed ILLUMINA™ sequencing using a slightly modified version of a previously published protocol (36). Two rounds of PCR amplification were performed on the lysed phage material using hot start Q5 polymerase according to the manufacturer suggested protocol (NEB). The first round of PCR used the primers IS7_HsORF5_2 (ACACTCTTTCCCTACACGACTCCAGTCAGGTGTGATGCTC) (SEQ ID NO: 18) and IS8_HsORF3_2 (GTGACTGGAGTTCAGACGTGTGCTCTTCCGATCCGAGCTTATCGTCGTCATCC) (SEQ ID NO: 19). The second round of PCR used 1 µL of the first round product and the primers IS4_HsORF5_2 (AATGATACGGCGACCACCGAGATCTACACTCTTTCCCTACACGACTCCAGT) (SEQ ID NO: 20) and a different unique indexing primer for each sample to be multiplexed for sequencing (CAAGCAGAAGACGGCATACGAGATxxxxxxxGTGACTGGAGTTCAGACGTGT (SEQ ID NO: 21), where "xxxxxxx" denotes a unique 7 nt indexing sequence). After the second round of PCR, the inventors determined the DNA concentration of each sample by qPCR and pooled equimolar amounts of all samples for gel extraction. Following gel extraction, the pooled DNA was sequenced by the Harvard Medical School Biopolymers Facility using a 50 bp read cycle on an Illumina HiSeq 2000 or 2500. The inventors pooled up to 192 samples for sequencing on each lane and generally obtained approximately 100-200 million reads per lane (500,000 to 1,000,000 reads per sample).

Informatics and Statistical Analysis:

The inventors performed the initial informatics and statistical analysis using a slightly modified version of the previously published technique (8, 10). They first mapped the sequencing reads to the original library sequences using Bowtie and counted the frequency of each clone in the "input" and each sample "output" (37). Since the majority of clones are not enriched the inventors use the observed distribution of output counts as a null distribution. It was found that a zero-inflated generalized poisson distribution fits the output counts well. The inventors used this null distribution to calculate a p-value for the likelihood of enrichment for each clone. The probability mass function for the zero-inflated generalized poisson distribution is $$P(Y = y) = \begin{cases} \pi + (1-\pi)(\theta(\theta + x\lambda)^{x-1}e^{-\theta-x\lambda}), & \text{if } y = 0 \\ (1-\pi)(\theta(\theta + x\lambda)^{x-1}e^{-\theta-x\lambda}), & \text{if } y > 0 \end{cases}$$

The inventors used maximum likelihood estimation to regress the parameters $\pi$, $\theta$, and $\lambda$ to fit the distribution of counts after immunoprecipitation for all clones present at a particular frequency count in the input. This procedure was repeated for all of the observed input counts and it was found that θ and λ are well fit by linear regression and π by an exponential regression as a function of input count (FIG. 19). Finally, for each clone the inventors used its input count and the regression results to determine the null distribution based on the zero-inflated generalized poisson model, which were used to calculate the $-\log_{10}$(p-value) of obtaining the observed count.

To call hits, the inventors determined the threshold for reproducibility between technical replicates based on a previously published method (10). Briefly, the inventors made scatter plots of the log 10 of the –log 10 (p-values) and used a sliding window of width 0.005 from 0 to 2 across the axis of one replicate. For all the clones that fell within each window, the inventors calculated the median and median absolute deviation of the log 10 of the –log 10 (p-values) in the other replicate and plotted it against the window location (FIG. 8). The inventors called the threshold for reproducibility the first window in which the median was greater than the median absolute deviation. It was found that the distribution of the threshold –log 10 (p-value) was centered around a mean of approximately 2.3 (FIG. 9). So the inventors called a peptide a "hit" if the –log 10 (p-value) was at least 2.3 in both replicates. The inventors eliminated the 593 hits that came up in at least three of the twenty-two immunoprecipitations with beads alone (negative control for non-specific binding). The inventors also filtered out any peptides that were not enriched in at least two of the samples.

To call virus exposures, the inventors grouped peptides according to the virus the peptide is derived from. All peptides were grouped from individual viral strains for which there were complete proteomes. The sample was counted as positive for a species if it was positive for any strain from that species. For viral strains which had partial proteomes, the inventors grouped them with other strains from the same species to form a complete set and bioinformatically eliminated homologous peptides. A threshold number of hits per virus was set based on the size of the virus. It was found that there is approximately a power-law relationship between size of the virus and the average number of hits per sample (FIG. 10). In comparing results from VirScan to samples with known infection, it was empirically determined that a threshold of 3 hits for herpes simplex virus 1 worked the best. This value and the slope of the best fit line was used to scale the threshold for other viruses. The inventors also set a minimum threshold of at least 2 hits in order to avoid false positives from single spurious hits.

To bioinformatically remove cross-reactive antibodies, the inventors first sorted the viruses by total number of hits in descending order. The inventors then iterated through each virus in this order. For each virus, the inventors iterated through each peptide hit. If the hit shared a subsequence of at least 7 aa with any hit previously observed in any of the viruses from that sample, that hit was considered to be from a cross-reactive antibody and would be ignored for that virus. Otherwise, the hit is considered to be specific and the score for that virus is incremented by one. In this way, the inventors summed only the peptide hits that do not share any linear epitopes. The inventors compared the final score for each virus to the threshold for that virus to determine whether the sample is positive for exposure to that virus To identify differences between populations, Fisher's exact test was first used to calculate a p-value for the significance of association of virus exposure with one population versus another. Then, the inventors constructed a null-distribution of Fisher's exact p-values by randomly permuting the sample labels 1000 times and re-calculating the Fisher's exact p-value for each virus. Using this null-distribution, the false discovery rate was calculated by dividing the number of permutation p-values more extreme than the one observed by the total number of permutations.

IEDB Epitope Overlap Analysis:

The inventors downloaded data for all continuous human B cell epitopes from IEDB and filtered out all non-viral epitopes (22). To avoid redundancy in these 4,549 viral epitopes, the inventors grouped together epitopes that share a 7 aa subsequence, yielding 1,877 non-redundant epitope groups. Of these groups, 1,715 contain a member epitope that is also a subsequence of a peptide in the VirScan library. This represents the total number of epitopes that could be detected by VirScan. To determine the number of epitopes detected, the inventors tallied the number of epitope groups with at least one member that is contained in a peptide that was enriched in one or two samples. Finally, to determine the number of non-redundant new epitopes detected, the inventors grouped non-IEDB epitopes containing peptides that share a 7 residues subsequence and counted the number of these non-redundant peptide groups.

Scanning Mutagenesis Data Analysis:

First, the inventors estimated the fractional abundance of each peptide by dividing the number of reads for that peptide by the total number of reads for the sample. Then, the inventors divided the fractional abundance of each peptide after immunoprecipitation by the fractional abundance before immunoprecipitation to get the enrichment. To calculate relative enrichment, the inventors divided enrichment of the mutated peptide by enrichment of the wild-type peptide. Since most of the single-mutant peptides had wild-type levels of enrichment, the inventors averaged enrichment of the wild-type peptide enrichment with enrichment of single-mutant peptides in the middle two quartiles to get a better estimate of the wild-type peptide enrichment.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are systems and methods incorporating a display system for identifying antibody generation, compositions arising from the described systems and methods, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A phage library displaying a plurality of viral peptides, from at least 3 unique viruses known to infect humans, wherein the phage display library is constructed using a synthetic programmable microarray from a starting library that is uniformly distributed.

2. The phage library of claim 1, wherein the phage library comprises a plurality of viral peptides from at least 10 viruses known to infect humans.

3. The phage library of claim 1, wherein the phage library comprises a plurality of viral peptides from at least 20 viruses known to infect humans.

4. The phage library of claim 1, wherein the phage library comprises at least 10 peptide sequences.

5. The phage library of claim 1, wherein the phage library comprises at least 20 peptide sequences.

6. The phage library of claim 1, wherein the plurality of peptides comprises peptides that are each less than 100, 200 or 300 amino acids long.

7. The phage library of claim 1, wherein the plurality of peptides comprises peptides that are each less than 75 amino acids long.

8. The phage library of claim 1, wherein each peptide of the plurality of peptides comprises a common adapter region appended to the end of a nucleic acid sequence encoding the peptide.

9. The phage library of claim 1, wherein the plurality of peptides comprises immunodominant epitopes.

* * * * *